United States Patent [19]
Broka et al.

[11] Patent Number: 5,998,412
[45] Date of Patent: Dec. 7, 1999

[54] SULFAMIDE-METALLOPROTEASE INHIBITORS

[75] Inventors: Chris Allen Broka, Foster City; Jeffrey Allen Campbell, Fremont, both of Calif.; Arlindo Lucas Castelhano, New City, N.Y.; Jian Jeffrey Chen, Santa Clara, Calif.; Robert Than Hendricks, Palo Alto, Calif.; Michael Joseph Melnick, San Diego, Calif.; Keith Adrian Murray Walker, Los Altos Hills, Calif.

[73] Assignees: Syntex (U.S.A.) Inc., Palo Alto; Agouron Pharmaceuticals, Inc., San Diego, both of Calif.

[21] Appl. No.: 09/009,951

[22] Filed: Jan. 21, 1998

Related U.S. Application Data

[60] Provisional application No. 60/036,714, Jan. 23, 1997, and provisional application No. 60/062,209, Oct. 16, 1997.

[51] Int. Cl.⁶ ............... A61K 31/435; A61K 31/495; C07D 491/048; C07D 495/04
[52] U.S. Cl. ............... 514/250; 514/255; 514/300; 514/301; 514/302; 514/318; 514/330; 514/331; 514/562; 544/350; 544/360; 544/380; 546/113; 546/114; 546/115; 546/193; 546/225; 546/235; 562/556
[58] Field of Search ............... 562/556; 514/562, 514/250, 300, 301, 302; 544/350; 546/113, 114, 115

[56] References Cited

U.S. PATENT DOCUMENTS

| | | |
|---|---|---|
| 5,036,053 | 7/1991 | Himmelsbach et al. ............... 514/19 |
| 5,089,616 | 2/1992 | Belmont et al. ............... 544/133 |
| 5,114,937 | 5/1992 | Hamby et al. ............... 514/238.2 |
| 5,142,056 | 8/1992 | Kempe et al. ............... 546/265 |
| 5,260,278 | 11/1993 | Himmelsbach et al. ............... 514/19 |
| 5,455,258 | 10/1995 | MacPherson et al. ............... 514/357 |
| 5,545,750 | 8/1996 | Kempf et al. ............... 564/360 |
| 5,643,878 | 7/1997 | Bold et al. ............... 514/19 |

FOREIGN PATENT DOCUMENTS

| | | |
|---|---|---|
| 97/19121 | 10/1997 | Australia . |
| 0 417 454 A2 | 3/1991 | European Pat. Off. . |
| 0 456 185 A2 | 11/1991 | European Pat. Off. . |
| 0 780 386 A1 | 6/1997 | European Pat. Off. . |
| WO93/06127 | 4/1993 | WIPO . |
| WO 93/06127 | 4/1993 | WIPO . |
| WO 93/24475 | 12/1993 | WIPO . |
| WO94/24140 | 10/1994 | WIPO . |
| WO95/06034 | 3/1995 | WIPO . |
| WO95/19956 | 7/1995 | WIPO . |
| WO95/19961 | 7/1995 | WIPO . |
| WO95/32944 | 12/1995 | WIPO . |
| WO95/35275 | 12/1995 | WIPO . |
| WO95/35276 | 12/1995 | WIPO . |
| WO96/00214 | 1/1996 | WIPO . |
| WO96/27583 | 9/1996 | WIPO . |
| WO97/05865 | 2/1997 | WIPO . |
| WO97/18194 | 5/1997 | WIPO . |
| WO 97/18194 | 5/1997 | WIPO . |
| WO97/19919 | 5/1997 | WIPO . |
| WO 98/08815 | 3/1998 | WIPO . |

OTHER PUBLICATIONS von Geldern, et al., Journal of Medicinal Chemistry, vol. 39:4, (1996), pp. 968–981, "Azole Endothelin Antagonists".
Chatterjee, et al., Bioorganic & Medicinal Chemistry Letters, vol. 6:11, 1996, pp. 1237–1240, "Potent Fluoromethyl Ketone Inhibitors of Recombinant Human Calpain 1+".
Patt, et al., J. Med. Chem., vol. 35:14, 1992, pp. 2562–2572, "Structure–Activity Relationships of a Series of 2–Amino–4–thiazole–Containing Renin Inhibitors".

Primary Examiner—Richard L. Raymond
Attorney, Agent, or Firm—Rohan Peries; Rekha Bansal

[57] ABSTRACT

This invention relates to sulfamides of formula (I)

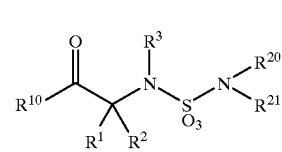

(I)

that are inhibitors of metalloproteases, pharmaceutical compositions containing them, methods for their use and methods for preparing these compounds.

15 Claims, No Drawings

SULFAMIDE-METALLOPROTEASE INHIBITORS

CROSS-REFERENCE TO RELATED APPLICATION

This application claims the benefit under 35 U.S.C. 119(e) of U.S. Provisional Application No. 60/036,714, filed Jan. 23, 1997 and U.S. Provisional Application No. 60/062,209, filed Oct. 16, 1997.

BACKGROUND OF THE INVENTION

1. Field of the Invention

The present invention relates to compounds that inhibit metalloproteases such as matrix metalloproteases, particularly interstitial collagenases, as well as TNF α-convertase and related sheddases and are therefore useful in the treatment of mammals having disease states alleviated by the inhibition of such metalloproteases.

2. Background Information and Related Disclosures

Matrix metalloproteases ("MMPs") are a family of proteases (enzymes) involved in the degradation and remodeling of connective tissues. Members of this family of endopeptidase enzymes are present in various cell types that reside in or are associated with connective tissue, such as fibroblasts, monocytes, macrophages, endothelial cells, and invasive or metastatic tumor cells. MMP expression is stimulated by growth factors and cytokines in the local tissue environment, where these enzymes act to specifically degrade protein components of the extracellular matrix, such as collagen, proteoglycans (protein core), fibronectin and laminin. These ubiquitous extracellular matrix components are present in the linings of joints, interstitial connective tissues, basement membranes, and cartilage. Excessive degradation of extracellular matrix by MMPs is implicated in the pathogenesis of many diseases, including rheumatoid arthritis, osteoarthritis, multiple sclerosis, bone resorptive diseases (such as osteoporosis), chronic obstructive pulmonary disease, restenosis, cerebral hemorrhaging associated with stroke, periodontal disease, aberrant angiogenesis, tumor invasion and metastasis, corneal and gastric ulceration, ulceration of skin, aneurysmal disease, and in complications of diabetes. MMP inhibition is, therefore, recognized as a good target for therapeutic intervention.

The MMPs share a number of properties, including zinc and calcium dependence, secretion as zymogens, and 40–50% amino acid sequence homology. The MMP family currently consists of at least fifteen enzymes, and includes collagenases, stromelysins, gelatinases, matrilysin, metalloelastase, and membrane-type MMP, as discussed in greater detail below.

Interstitial collagenases catalyze the initial and rate-limiting cleavage of native collagen types I, II, and III. Collagen, the major structural protein of mammals, is an essential component of the matrix of many tissues, for example, cartilage, bone, tendon and skin. Interstitial collagenases are very specific matrix metalloproteases which cleave these collagens to give two fragments which spontaneously denature at physiological temperatures and therefore become susceptible to cleavage by less specific enzymes. Cleavage by the collagenases results in the loss of structural integrity of the target tissue, essentially an irreversible process. There are currently three known human collagenases. The first is human fibroblast-type collagenase (HFC, MMP-1, or collagenase-1) that is produced by a wide variety of cells including fibroblasts and macrophages. The second is human neutrophil-type collagenase (HNC MMP-8, or collagenase-2) which has so far only been demonstrated to be produced by neutrophils. The most recently discovered member of this group of MMPs is human collagenase-3 (MMP-13) which was originally found in breast carcinomas, but has since shown to be produced by chondrocytes. The only collagenase known to exist in rodents is the homolog of human collagenase-3.

The gelatinases include two distinct, but highly related, enzymes: a 72-kD enzyme (gelatinase A, HFG, MMP-2) secreted by fibroblasts and a wide variety of other cell types, and a 92-kD enzyme (gelatinase B, HNG, MMP-9) released by mononuclear phagocytes, neutrophils, corneal epithelial cells, tumor cells, cytotrophoblasts and keratinocytes. These gelatinases have been shown to degrade gelatins (denatured collagens), collagen types IV (basement membrane) and V, fibronectin and insoluble elastin.

Stromelysins 1 and 2 have been shown to cleave a broad range of matrix substrates, including laminin, fibronectin, proteoglycans, and collagen types IV and IX in their non-helical domains.

Matrilysin (MMP-7, PUMP-1) has been shown to degrade a wide range of matrix substrates including proteoglycans, gelatins, fibronectin, elastin, and laminin. Its expression has been documented in mononuclear phagocytes, rat uterine explants and sporadically in tumors. Other less characterized MMPs include macrophage metalloelastase (MME, MMP-12), membrane type MMP (MMP-14), and stromelysin-3 (MMP-11).

Inhibitors of MMPs provide useful treatments for diseases associated with the excessive degradation of extracellular matrix, such as arthritic diseases (rheumatoid arthritis and osteoarthritis), multiple sclerosis, bone resorptive diseases (such as osteoporosis), the enhanced collagen destruction associated with diabetes, chronic obstructive pulmonary disease, cerebral hemorrhaging associated with stroke, periodontal disease, corneal or gastric ulceration, ulceration of the skin, tumor invasion and metastasis, aneurysmal disease such as abdominal aortic aneurysm disease, and aberrant angiogenesis. The involvement of individual collagenases in the degradation of tissue collagens probably depends markedly on the tissue. The tissue distribution of human collagenases suggests that collagenase-3 is the major participant in the degradation of the collagen matrix of cartilage, while collagenase-1 is more likely to be involved in tissue remodeling of skin and other soft tissues. Thus, inhibitors selective for collagenase-3 over collagenase-1 are preferred for treatment of diseases associated with cartilage erosion, such as arthritis, etc.

Some inhibitors of MMP also are known to substantially inhibit the release of tumor necrosis factor (TNF) from cells and therefore may be used in the treatment of conditions mediated by TNF. Such uses include, but are not limited to, the treatment of inflammation, fever, cardiovascular effects, hemorrhage, coagulation and acute phase response, cachexia and anorexia, acute infections, shock states, restenosis, graft versus host reactions and autoimmune disease. Compounds of this invention may inhibit TNF release without inhibiting the MMPs.

In addition to these effects on the release of TNF from cells, MMP inhibitors and related compounds have also been shown to inhibit the release of other biologically active molecules from cells, including soluble receptors (CD30 and receptors for TNF (p55 and p75), IL-6, IL-1 and TSH), adhesion molecules (e.g., L-selecting, ICAM-1, fibronectin) and other growth factors and cytokines, including Fas ligand, TGF-α, EGF, HB-EGF, SCF and M-CSF. The release of such molecules is facilitated by several proteolytic proteins known as sheddases. Inhibition of the release or shedding of such molecules by inhibiting the sheddases may be of benefit in a number of disease states, including rheumatoid arthritis, multiple sclerosis, vascular disease, Type II diabetes, HIV, cachexia, psoriasis, allergy, hepatitis, inflammatory bowel disease, and cancer. Since non-specific inhibition of the shedding enzymes (sheddases) may have opposite pharmacological effects, selectivity will be a particular advantage, e.g., the inhibition of TNF release without the concurrent inhibition of TNF receptor release.

The design and uses of MMP inhibitors is described, for example, in *J. Enzyme Inhibition*, 2, 1–22 (1987); *Drug News & Prospectives*, 3(8), 453–458 (1990); *Arthritis and Rheumatism*, 36(2), 181–189 (1993); *Arthritis and Rheumatism*, 34(9), 1073–1075 (1991); *Seminars in Arthritis and Rheumatism*, 19(4), Supplement 1 (February), 16–20 (1990); *Drugs of the Future*, 15(5), 495–508 (1990); *Annals N.Y. Acad. Sci.*, 157, (1996), and *J. Enzyme Inhibition*, 2, 1–22 (1987). MMP inhibitors are also the subject of various patents and patent applications, for example, U.S. Pat. Nos. 5,189,178 and 5,183,900, European Published Patent Applications 438 223, 606 426, and 276 436, and Patent Cooperation Treaty International Applications 92/21360, 92/06966, 92/09563, and 94/25434.

SUMMARY OF THE INVENTION

In a first aspect, this invention provides hydroxamic acids and their derivatives selected from the group of compounds represented by formula (I):

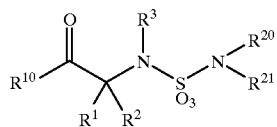

(I)

wherein:
$R^1$ and $R^2$ are independently selected from hydrogen, alkyl, alkenyl, haloalkyl, cycloalkyl, cycloalkylalkyl, aryl, aralkyl, heteroaryl, heteroaralkyl, heterocyclo, heterocycloalkyl, heteroalkyl, or -(alkylene)—C(O)—X where X is alkyl, haloalkyl, alkoxy, haloalkyloxy, amino, monosubstituted amino, disubstituted amino, aryl, aralkyl, aryloxy, heteroaryloxy, hydroxy, aralkyloxy, heteroaralkyloxy, or heteroaryl; or $R^1$ and $R^2$ together with the carbon atom to which they are attached form a carbocycle or a heterocycle;
$R^3$ is hydrogen, alkyl, alkenyl, haloalkyl, cycloalkyl, cycloalkylalkyl, aryl, aralkyl, aralkenyl, heteroaryl, heteroaralkyl, heteroaralkenyl, heterocycloalkyl, heteroalkyl, (diphenylmethyl)alkyl, or -(alkylene)—C(O)—X where X is alkyl, haloalkyl, alkoxy, haloalkyloxy, amino, monosubstituted amino, disubstituted amino, aryl, aralkyl, aryloxy, heteroaryloxy, hydroxy, aralkyloxy, heteroaralkyloxy, or heteroaryl; or $R^3$ together with either $R^1$ or $R^2$ and the atoms to which they are attached forms a heterocycloamino group;
$R^{10}$ is -$NR^{11}OR^{12}$ wherein:
$R^{11}$ and $R^{12}$ are independently selected from hydrogen, alkyl, or aralkyl;
$R^{20}$ and $R^{21}$ are independently selected from hydrogen, alkyl, heteroalkyl, cycloalkyl, cycloalkylalkyl, aryl, aralkyl, aralkenyl, heteroaralkyl, or heteroaralkenyl;

or $R^{20}$ and $R^{21}$ together with the nitrogen atom to which they are attached form a heterocycloamino group or an optionally substituted tetrahydropyridine or hexahydroazepine ring; or either of $R^{20}$ or $R^{21}$ together with $R^3$ forms an alkylene group; and
their pharmaceutically acceptable salts, prodrugs, individual isomers, and mixtures of isomers, provided that $R^{20}$ and $R^{21}$ together with the nitrogen atom to which they are attached do not form a morpholino ring either:
(i) when $R^1$ and $R^3$ are hydrogen and $R^2$ is aralkyl; or
(ii) when $R^1$ and $R^3$ together with the atoms to which they are attached form a tetrahydroisoquinoline ring and $R^2$ is hydrogen.

In a second aspect, this invention provides carboxylic acids selected from the group of compounds represented by formula (I):

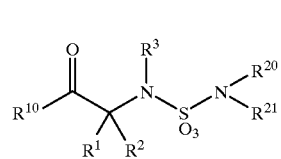

(I)

wherein:
$R^1$ and $R^2$ are independently selected from hydrogen, alkyl, alkenyl, haloalkyl, cycloalkyl, cycloalkylalkyl, aryl, aralkyl, heteroaryl, heteroaralkyl, heterocyclo, heterocycloalkyl, heteroalkyl, or -(alkylene)—C(O)—X where X is alkyl, haloalkyl, alkoxy, haloalkyloxy, amino, monosubstituted amino, disubstituted amino, aryl, aralkyl, aryloxy, heteroaryloxy, hydroxy, aralkyloxy, heteroaralkyloxy, or heteroaryl; or $R^1$ and $R^2$ together with the carbon atom to which they are attached form a carbocycle or a heterocycle;
$R^3$ is hydrogen, alkyl, alkenyl, haloalkyl, cycloalkyl, cycloalkylalkyl, aryl, aralkyl, aralkenyl, heteroaryl, heteroaralkyl, heteroaralkenyl, heterocycloalkyl, heteroalkyl, (diphenylmethyl)alkyl, or -(alkylene)—C(O)—X where X is alkyl, haloalkyl, alkoxy, haloalkyloxy, amino, monosubstituted amino, disubstituted amino, aryl, aralkyl, aryloxy, heteroaryloxy, hydroxy, aralkyloxy, heteroaralkyloxy, or heteroaryl; or $R^3$ together with either $R^1$ or $R^2$ and the atoms to which they are attached form a heterocycloamino group;
$R^{10}$ is —OH;
$R^{20}$ is hydrogen or alkyl; and
$R^{21}$ is cycloalkylalkyl, aryl, aralkyl, aralkenyl, heteroaralkyl or heteroaralkenyl; or
$R^{20}$ and $R^{21}$ together with the nitrogen atom to which they are attached form either:
(i) a heterocycloamino group substituted with at least one substituent selected from cycloalkyl, cycloalkylalkyl, aryl, aralkyl, heteroaryl, heteroaralkyl, cycloalkyl-Q-, aryl-Q-, or heteroaryl-Q- where Q is an alkylene chain in which a methylene group is optionally replaced by —C(O)—, —O—, —S(O)n— (where n is an integer from 0 to 2), —NR— (where R is hydrogen or alkyl), —$NR^aC(O)$—, —$C(O)NR^a$— (where $R^a$ is hydrogen or alkyl), —$NR^bSO_2$—, or —$SO_2NRb$- (where $R^b$ is hydrogen or alkyl);
(ii) a heterocycloamino group that is fused to a cycloalkyl, aryl or heteroaryl ring; or
(iii) an optionally substituted tetrahydropyridine or hexahydroazepine ring;

or either of $R^{20}$ or $R^{21}$ together with $R^3$ forms an alkylene group; and their pharmaceutically acceptable salts, prodrugs, individual isomers, and mixtures of isomers, provided that:

(i) $R^1$, $R^2$, and $R^3$ are not all hydrogen; and (ii) when $R^1$ and $R^3$ are hydrogen and $R^2$ is alkyl, then $R^{21}$ is not pyridylalkyl.

In a third aspect, this invention provides pharmaceutical compositions containing a therapeutically effective amount of a compound of formula (I) or its pharmaceutically acceptable salt and a pharmaceutically acceptable excipient.

In a fourth aspect, this invention provides a method of treatment of a disease in a mammal treatable by administration of a metalloproteinase inhibitor, comprising administration of a therapeutically effective amount of a compound of formula (I) or its pharmaceutically acceptable salt.

In a fifth aspect, this invention provides processes for preparing compounds of formula (I).

DETAILED DESCRIPTION OF THE INVENTION

Definitions

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkenylene" means a linear divalent hydrocarbon radical of two to six carbon atoms or a branched monovalent hydrocarbon radical of three to six carbon atoms, containing at least one double bond, e.g., ethenylene, 2-propenylene, and the like.

"Acyl" means a radical —C(O)R where R is hydrogen, alkyl, alkenyl, cycloalkyl, cycloalkylalkyl, haloalkyl, aryl, aralkyl, aralkenyl, heteroaryl, heteroaralkyl, heteroaralkenyl, or heterocyclo, e.g., acetyl, benzoyl, thenoyl, and the like.

"Acyloxy" means a radical —OC(O)R where R is hydrogen, alkyl, alkenyl, cycloalkyl, cycloalkylalkyl, or haloalkyl, e.g., acetoxy, 3,3,3-trifluoroacetoxy and the like.

"Acylamino" means a radical —NRC(O)R' where R is hydrogen or alkyl and R' is hydrogen, alkyl, alkenyl, cycloalkyl, cycloalkylalkyl, heteroalkyl, haloalkyl, aryl, aralkyl, aralkenyl, heteroaryl, heteroaralkenyl, or heteroaralkyl, e.g., acetylamino, trifluoroacetylamino, benzoylamino, methylacetylamino, and the like.

"Sulfonylamino" means a radical —NRSO$_2$R' where R is hydrogen or alkyl and R' is alkyl, alkenyl, cycloalkyl, cycloalkylalkyl, heteroalkyl, haloalkyl, amino, monosubstituted amino, disubstituted amino, aryl, aralkyl, aralkenyl, heteroaryl, heteroaralkenyl, or heteroaralkyl, e.g., methylsulfonylamino, benzylsulfonylamino, N-methylaminosulfonylamino, and the like.

"Halo" means fluoro, chloro, bromo, or iodo, preferably fluoro and chloro.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Cycloalkyl" means a saturated monovalent cyclic hydrocarbon radical of three to six ring carbons, e.g., cyclopropyl, cyclopentyl, cyclohexyl, and the like.

"Carbocycle" means a saturated, cyclic group of 3 to 8 ring atoms in which all the ring atoms are carbon, e.g., cyclopentyl, cyclohexyl, and the like.

"Monosubstituted amino" means a radical —NHR where R is alkyl, alkenyl, haloalkyl, cycloalkyl, cycloalkylalkyl, aryl, aralkyl, aralkenyl, heteroaryl, heteroaralkyl, or an amino protecting group, e.g., methylamino, (1-methylethyl) amino, phenylamino, and the like.

"Disubstituted amino" means a radical —NRR' where R and R' are independently alkyl, alkenyl, haloalkyl, cycloalkyl, cycloalkylalkyl, aryl, aralkyl, aralkenyl, heteroaryl, heteroaralkyl, or an amino protecting group. Representative examples include, but are not limited to dimethylamino, methylethylamino, di(1-methylethyl) amino, methylbenzylamino, and the like.

"Aryl" means a monovalent monocyclic or bicyclic aromatic hydrocarbon radical of 6 to 10 ring atoms and optionally substituted independently with one or more substituents, preferably one or two substituents selected from alkyl, haloalkyl, halo, nitro, acyloxy, cyano, cycloalkyl, cycloalkylalkyl, optionally substituted phenyl, optionally substituted phenylalkyl, heteroaryl, heteroaralkyl, —OR (where R is hydrogen, alkyl, haloalkyl, alkenyl, cycloalkyl, cycloalkylalkyl, optionally substituted phenyl, heteroaryl, optionally substituted phenylalkyl, or heteroaralkyl), —NRR' (where R and R' are independently hydrogen, alkyl, alkenyl, haloalkyl, cycloalkyl, cycloalkylalkyl, optionally substituted phenyl, optionally substituted phenylalkyl, optionally substituted phenylalkenyl, heteroaryl, or heteroaralkyl), —C(O)R (where R is hydrogen, alkyl, alkenyl, cycloalkyl, cycloalkylalkyl, haloalkyl, optionally substituted phenyl, optionally substituted phenylalkyl, optionally substituted phenylalkenyl, heteroaryl, heteroaralkyl, or heteroaralkenyl), —S(O)$_n$R (where n is an integer from 0 to 2 and R is hydrogen (provided that n is 0), alkyl, haloalkyl, alkenyl, cycloalkyl, cycloalkylalkyl, optionally substituted phenyl, heteroaryl, optionally substituted phenylalkyl, or heteroaralkyl), —SO$_2$NRR' (where R and R' are independently hydrogen, alkyl, alkenyl, haloalkyl, cycloalkyl, cycloalkylalkyl, optionally substituted phenyl, optionally substituted phenylalkyl, optionally substituted phenylalkenyl, heteroaryl or heteroaralkyl), —COOH, -(alkylene)—COOH, -(alkenylene)—COOH, —COOR$^a$, -(alkenylene)—COOR$^a$, -(alkylene)—COOR$^a$ (where R$^a$ is alkyl, optionally substituted phenylalkyl, or heteroaralkyl), —CONR'R", -(alkylene)—CONR'R", (where R' and R" are independently selected from hydrogen, alkyl, cycloalkyl, cycloalkylalkyl, optionally substituted phenyl, optionally substituted phenylalkyl, heteroaryl, and heteroaralkyl), —NRC(O)R' (where R is hydrogen or alkyl and R' is hydrogen, alkyl, alkenyl, cycloalkyl, cycloalkylalkyl, haloalkyl, optionally substituted phenyl, optionally substituted phenylalkyl, optionally substituted phenylalkenyl, heteroaryl, heteroaralkenyl, or heteroaralkyl), —NRSO$_2$R' (where R is hydrogen or alkyl and R' is alkyl, alkenyl, cycloalkyl, cycloalkylalkyl, haloalkyl, optionally substituted phenyl, optionally substituted phenylalkyl, optionally substituted phenylalkenyl, heteroaryl, heteroaralkenyl, or heteroaralkyl), or —NRSO$_2$NR'R" (where R is hydrogen or alkyl and R' and R" are independently hydrogen, alkyl, alkenyl, haloalkyl, cycloalkyl, cycloalkylalkyl, optionally substituted phenyl, optionally substituted phenylalkyl, or optionally substituted phenylalkenyl). More specifically the term aryl includes, but is not limited to, phenyl, 1-napthyl and 2-naphthyl, and the derivatives thereof.

"Heteroaryl" means a monovalent monocyclic or bicyclic aromatic radical of 5 to 10 ring atoms containing one, two, or three ring heteroatoms selected from N, O, or S, the remaining ring atoms being C. The heteroaryl ring is optionally substituted independently with one or more substituents, preferably one or two substituents, selected from alkyl, haloalkyl, halo, nitro, cyano, cycloalkyl, cycloalkylalkyl, optionally substituted phenyl, optionally substituted phenylalkyl, —OR (where R is hydrogen, alkyl, haloalkyl, alkenyl, cycloalkyl, cycloalkylalkyl, optionally substituted phenyl or optionally substituted phenylalkyl), —NRR' (where R and R' are independently hydrogen, alkyl, alkenyl, haloalkyl, cycloalkyl, cycloalkylalkyl, optionally substituted phenyl, optionally substituted phenylalkyl, or optionally substituted phenylalkenyl), —C(O)R (where R is hydrogen, alkyl, alkenyl, cycloalkyl, cycloalkylalkyl, haloalkyl, optionally substituted phenyl, optionally substituted phenylalkyl, or optionally substituted phenylalkenyl), —S(O)$_n$R (where n is an integer from 0 to 2 and R is hydrogen (provided that n is 0), alkyl, haloalkyl, alkenyl, cycloalkyl, cycloalkylalkyl, optionally substituted phenyl, or optionally substituted phenylalkyl), —SO$_2$NRR' (where R and R' are independently hydrogen, alkyl, alkenyl, haloalkyl, cycloalkyl, cycloalkylalkyl, optionally substituted phenyl, optionally substituted phenylalkyl, or optionally substituted phenylalkenyl)], —COOH, -(alkylene)—COOH,-(alkenylene)COOH, —COOR$^a$, -(alkenylene)—COOR$^a$, -(alkylene)—COOR$^a$ (where R$^a$ is alkyl, or optionally substituted phenylalkyl), —CONR'R", -(alkylene)—CONR'R", (where R' and R" are independently selected from hydrogen, alkyl, cycloalkyl, cycloalkylalkyl, optionally substituted phenyl, or optionally substituted phenylalkyl), —NRC(O)R' (where R is hydrogen or alkyl and R' is hydrogen, alkyl, alkenyl, cycloalkyl, cycloalkylalkyl, haloalkyl, optionally substituted phenyl, optionally substituted phenylalkyl, or optionally substituted phenylalkenyl), —NRSO$_2$R' (where R is hydrogen or alkyl and R' is alkyl, alkenyl, cycloalkyl, cycloalkylalkyl, haloalkyl, optionally substituted phenyl, optionally substituted phenylalkyl, or optionally substituted phenylalkenyl), —NRSO$_2$NR'R" (where R is hydrogen or alkyl and R' and R" are independently hydrogen, alkyl, alkenyl, haloalkyl, cycloalkyl, cycloalkylalkyl, optionally substituted phenyl, optionally substituted phenylalkyl, or optionally substituted phenylalkenyl), or an amino protecting group. More specifically the term heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl and benzodiazepin-2-one-5-yl, and the derivatives thereof.

"Optionally substituted phenyl" means phenyl ring which is optionally substituted with one or more substituents, preferably one or two substituents selected from alkyl, haloalkyl, halo, nitro, cyano, —NRR' (where R and R' are independently selected from hydrogen or alkyl), —OR (where R is hydrogen, alkyl or haloalkyl), —COOR$^a$ (where R$^a$ is hydrogen or alkyl) or —CONR'R" (where R' and R" are independently selected from hydrogen or alkyl). Representative examples include, but are not limited to, phenyl, 3-chlorophenyl, 4-(methylthio)phenyl, and the like.

"Heterocycloamino" means a saturated monovalent cyclic group of 4 to 8 ring atoms, wherein at least one ring atom is N and optionally contains one or two additional ring heteroatoms selected from the group consisting of N, O, or S(O)$_n$ (where n is an integer from 0 to 2), the remaining ring atoms being C, where one or two C atoms may optionally be replaced by a carbonyl group. The heterocycloamino ring may be fused to a cycloalkyl, aryl or heteroaryl ring, and it may be optionally substituted with one or more substituents, preferably one or two substituents, selected from alkyl, haloalkyl, heteroalkyl, cycloalkyl, cycloalkylalkyl, aryl, aralkyl, heteroaryl, heteroaralkyl, diphenylmethyl, (diphenylmethyl)alkyl, halo, cyano, acyl, amino, monosubstituted amino, disubstituted amino, acylamino, sulfonylamino, —OR (where R is hydrogen, alkyl, haloalkyl, alkenyl, cycloalkyl, cycloalkylalkyl, acyl, aryl, heteroaryl, aralkyl, or heteroaralkyl), —S(O)$_n$R [where n is an integer from 0 to 2 and R is hydrogen (provided that n is 0), alkyl, haloalkyl, alkenyl, cycloalkyl, cycloalkylalkyl, amino, monosubstituted amino, disubstituted amino, heterocyclo, aryl, heteroaryl, aralkyl, or heteroaralkyl], —P(O)(NR$^b$R$^c$)$_2$ (where R$^b$ and R$^c$ are independently selected from alkyl or aralkyl), —COOH, -(alkylene)—COOH, -(alkenylene)—COOH, —COOR$^a$, -(alkylene)—COOR$^a$, -(alkenylene)COOR$^a$ (where R$^a$ is alkyl, heteroalkyl, aralkyl, or heteroaralkyl), —CONR'R", -(alkylene)CONR'R", (where R' and R" are independently selected from hydrogen, alkyl, cycloalkyl, cycloalkylalkyl, aryl, aralkyl, heteroaryl, or heteroaralkyl), —COCH(R')NH$_2$ (where R' is a side chain of a natural or unnatural alpha amino acid in which any functional group present may be protected), an amino protecting group, or 1,3-dihydro-2H-1,4-benzodiazepin-2-one wherein the N-1 and C-3 positions may be optionally substituted, independently of each other, with a substituent selected from alkyl, cycloalkyl, cycloalkylalkyl, aryl, aralkyl, heteroaryl, acyl, and heteroaralkyl. More specifically the term heterocycloamino includes, but is not limited to, pyrrolidino, piperidino, morpholino, piperazino, indolino, thiomorpholino, thiomorpholino-1-oxide, thiomorpholino-1,1-dioxide, 1,2,3,4-tetrahydro-(α, β, or -γ, -carbolino, tetrahydroisoquinolyl, and 1,3-dihydro-2H-1,4-benzodiazepin-2-one-5-yl, and the derivatives thereof.

"Optionally substituted tetrahydropyridine or hexahydroazepine ring" means a tetrahydropyridine or a hexahydroazepine ring that is optionally substituted with one or two substituents selected from alkyl, haloalkyl, heteroalkyl, cycloalkyl, cycloalkylalkyl, aryl, aralkyl, heteroaryl, heteroaralkyl, diphenylmethyl, (diphenylmethyl)alkyl, acyl, hydroxy, —COOH, -(alkylene)—COOH, -(alkenylene)—COOH, —COOR$^a$, -(alkylene)—COOR$^a$, -(alkenylene)—COCR$^a$ (where R$^a$ is alkyl, heteroalkyl, aralkyl, or heteroaralkyl), —S(O)$_n$R [where n is an integer from 1 to 2 and R is hydrogen (provided that n is 0), alkyl, haloalkyl, alkenyl, cycloalkyl, cycloalkylalkyl, amino, monosubstituted amino, disubstituted amino, aryl, heteroaryl, aralkyl, or heteroaralkyl], —CONR'R", and -(alkylene)—CONR'R" (where R' and R" are independently selected from hydrogen, alkyl, cycloalkyl, cycloalkylalkyl, aryl, aralkyl, heteroaryl, or heteroaralkyl). Representative examples include, but are not limited to, 4-(4-fluorophenyl)-1,2,3,6-tetrahydropyridine, and the like.

"Heterocycle" or "Heterocyclo" means a saturated cyclic radical of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group. The heterocyclo ring may be optionally substituted independently with one, two, or three substituents selected from alkyl, haloalkyl, cycloalkyl, cycloalkylalkyl, arvl, aralkyl, heteroaryl, heteroaralkyl, halo, cyano, acylamino, amino, monosubstituted amino, disubstituted amino, —OR (where R is hydrogen, alkyl, haloalkyl, alkenyl, cycloalkyl, cycloalkylalkyl, aryl, heteroaryl, aralkyl, or heteroaralkyl), —C(O)R (where R is hydrogen, alkyl, alkenyl, cycloalkyl, cycloalkylalkyl, haloalkyl, aryl, aralkyl, aralkenyl, heteroaryl, heteroaralkyl, or heteroaralkenyl), —S(O)$_n$R [where n is an integer from 0 to 2 and R is hydrogen (provided that n is 0), alkyl, haloalkyl, alkenyl, cycloalkyl, cycloalkylalkyl, amino, monosubstituted amino, disubstituted amino, aryl, heteroaryl, aralkyl, or heteroaralkyl], —COOH, -(alkylene)—COOH, —COOR$^a$, -(alkylene)—COOR$^a$ (where R$^a$ is alkyl, heteroalkyl, aralkyl, or heteroaralkyl), —CONR'R", -(alkylene)—CONR'R" (where R' and R" are independently selected from hydrogen, alkyl, cycloalkyl, cycloalkylalkyl, aryl, aralkyl, heteroaryl, and heteroaralkyl) or an amino protecting group. More specifically the term heterocyclo includes, but is not limited to, tetrahydropyranyl, piperidino, piperazino, morpholino and thiomorpholino, thiomorpholino-1-oxide, thiomorpholino-1,1-dioxide, and the derivatives thereof.

"Heteroalkyl" means an alkyl, cycloalkyl, or cycloalkylalkyl radical as defined above, carrying a substituent selected from —NR$^a$R$^b$, —OR$^c$, —S(O)$_n$R$^d$, —P(O)(OR$^e$)(OR$^f$), —P(O)(OR$^e$)R$^g$, or —P(O)(NR$^h$R$^i$)$_2$, wherein n is an integer from 0 to 2, R$^a$ is hydrogen, alkyl, haloalkyl, cycloalkyl, cycloalkylalkyl, aryl, aralkyl, aralkenyl, heteroaryl, heteroaralkyl, heteroaralkenyl, or acyl; R$^b$ is hydrogen, alkyl, aryl, aralkyl, acyl, —SO$_2$R (where R is alkyl, haloalkyl, amino, monosubstituted amino or disubstituted amino), —COOR (where R is hydrogen, alkyl, aralkyl, or heteroaralkyl), —CONR'R", -(alkylene)CONR'R" (where R' and R" are independently selected from hydrogen, alkyl, cycloalkyl, cycloalkylalkyl, aryl, aralkyl, heteroaryl, and heteroaralkyl), —P(O)(OR)$_2$ (where each R is independently alkyl, aryl or aralkyl), —P(O)(NR'R")$_2$ (where R' and R" are independently selected from alkyl, alkenyl, haloalkyl, cycloalkyl, cycloalkylalkyl, aryl, aralkyl, heteroaryl, or heteroaralkyl), or —P(O)(OR)R' (where R is alkyl, aryl, or aralkyl and R' is alkyl, cycloalkyl, cycloalkylalkyl, aryl, aralkyl, heteroaryl, or heteroaralkyl); R$^c$ is hydrogen, alkyl, haloalkyl, cycloalkyl, cycloalkylalkyl, aryl, aralkyl, aralkenyl, heteroaryl, heteroaralkyl, heteroaralkenyl, acyl, —CONR'R" (where R' and R" are independently selected from hydrogen, alkyl, cycloalkyl, cycloalkylalkyl, aryl, aralkyl, heteroaryl, or heteroaralkyl), —P(O)(OR)$_2$ (where each R is independently alkyl, aryl or aralkyl), —P(O)(NR'R")$_2$ (where R' and R" are independently selected from alkyl, alkenyl, heteroalkyl, haloalkyl, cycloalkyl, cycloalkylalkyl, aryl, aralkyl, heteroaryl, or heteroaralkyl), or —P(O)(OR)R' (where R is alkyl, aryl, or aralkyl and R' is alkyl, cycloalkyl, cycloalkylalkyl, aryl, aralkyl, heteroaryl, or heteroaralkyl); R$^d$ is hydrogen (provided that n is 0), alkyl, cycloalkyl, cycloalkylalkyl, aryl, aralkyl, heteroaryl, heteroaralkyl, amino, monosubstituted amino, or disubstituted amino; R$^e$ and R$^f$ are independently selected from alkyl or aryl; R$^g$ is hydrogen, alkyl, cycloalkyl, cycloalkylalkyl, aryl, aralkyl, heteroaryl, or heteroaralkyl; R$^h$ and R$^i$ are independently selected from alkyl, alkenyl, heteroalkyl, haloalkyl, cycloalkyl, cycloalkylalkyl, aryl, aralkyl, heteroaryl, or heteroaralkyl. Representative examples include, but are not limited to 2-methoxyethyl, benzyloxymethyl, thiophen-2-ylthiomethyl, and the like;

"Cycloalkylalkyl" means a radical —R$^a$R$^b$ where R$^a$ is an alkylene group and R$^b$ is a cycloalkyl group as defined above e.g., cyclopropylmethyl, cyclohexylpropyl, 3-cyclohexyl-2-methylpropyl, and the like.

"Aralkyl" means a radical —R$^a$R$^b$ where R$^a$ is an alkylene group and R$^b$ is an aryl group as defined above e.g., benzyl, phenylethyl, 3-(3-chlorophenyl)-2-methylpentyl, and the like.

"Aralkenyl" means a radical —R$^a$R$^b$ where R$^a$ is an alkenyl group and R$^b$ is an aryl group as defined above e.g., 3-phenyl-2-propenyl, and the like.

"Heteroaralkyl" means a radical —R$^a$R$^b$ where R$^a$ is an alkylene group and R$^b$ is a heteroaryl group as defined above e.g., pyridin-3-ylmethyl, 3-(benzofuran-2-yl)propyl, and the like.

"Heteroaralkenyl" means a radical —R$^a$R$^b$ where R$^a$ is an alkenyl group and R$^b$ is a heteroaryl group as defined above e.g., 3-pyridin-3-ylpropen-2-yl, and the like.

"Heterocycloalkyl" means a radical —R$^a$R$^b$ where R$^a$ is an alkylene group and R$^b$ is a heterocyclo group as defined above e.g., tetrahydropyran-2-ylmethyl, 4-methylpiperazin-1-ylethyl, and the like.

"Alkoxy", "iryloxy", "heteroaryloxy", "aralkyloxy", or "heteroaralkyloxy" means a radical —OR where R is an alkyl, aryl, heteroaryl, aralkyl, or heteroaralkyl respectively, as defined above e.g., methoxy, phenoxy, pyridin-2-yloxy, benzyloxy, and the like.

"Optional" or "optionally" means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

"Amino protecting group" refers to those organic groups intended to protect nitrogen atoms against undesirable reactions during synthetic procedures e.g., benzyl, benzyloxycarbonyl (CBZ), tert-butoxycarbonyl (Boc), trifluoroacetyl, 2-trimethylsilylethanesulfonyl (SES), and the like.

Compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the $R^1$ and $R^2$ substituents in a compound of formula (I) are different, then the carbon to which they are attached is an asymmetric center and therefore the compound of formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethimesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]-oct-2-ene-1-carboxylic acid, glucoheptonic acid, 4,4'-methylenebis- (3-hydroxy-2-ene-1-carboxylic acid), 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Pro-drugs" means any compound which releases an active parent drug according to formula (I) in vivo when such prodrug is administered to a mammalian subject. Prodrugs of a compound of formula (I) are prepared by modifying functional groups present in the compound of formula (I) in such a way that the modifications may be cleaved in vivo to release the parent compound. Prodrugs include compounds of formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of formula (I), and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Nomenclature

The naming and numbering of the compounds of this invention is illustrated below.

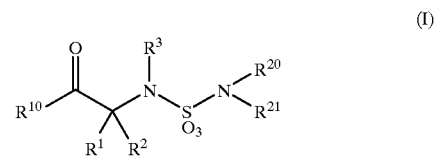

(I)

The nomenclature used in this application is generally based on the IUPAC recommendations, e.g., a compound of formula (I):

where $R^{10}$ is —NHOH, $R^1$ is 2-propyl, $R^2$ is hydrogen, $R^3$ is benzyl, the stereochemistry at the carbon to which $R^1$ and $R^2$ are attached is (RS), and $R^{20}$ and $R^{21}$ together with the nitrogen atom to which they are attached form a piperidino ring substituted at the 4-position with phenoxy, is named N-hydroxy-2-(RS)-{[benzyl-4-(phenoxy)piperidine-1-sulfonyl]amino}-3-methylbutyramide where $R^{10}$ is —OH, $R^1$ is Me, $R^2$ and $R^3$ are hydrogen, the stereochemistry at the carbon to which $R^1$ and $R^2$ are attached is (RS), and $R^{20}$ and $R^{21}$ together with the nitrogen atom to which they are attached form a piperazino ring substituted at the 4-position with 4-chlorophenyl, is named 2-(RS)-{[4-(4-chlorophenyl)piperazine-1-sulfonyl]amino }propionic acid;

where $R^{10}$ is —NHOH, $R^1$ and $R^2$ form a cyclopentane ring, $R^3$ is hydrogen, the stereochemistry at the carbon to which $R^1$ and $R^2$ are attached is (RS), and $R^{20}$ and $R^{21}$ together with the nitrogen atom to which they are attached form a piperazino ring substituted at the 4-position with 4-chlorophenyl, is named N-hydroxy-1-{[4-(4-chlorophenyl)piperazine-1-sulfonyl]amino}cyclopentane-1-(RS)-carboxamide;

where $R^{10}$ is —NHOH, $R^1$ and $R^3$ form a piperidine ring, $R^2$ is hydrogen, the stereochemistry at the carbon to which $R^1$ and $R^2$ are attached is (R), and $R^{20}$ and $R^{21}$ together with the nitrogen atom to which they are attached form a piperazino ring substituted at the 4-position with phenoxy, is named N-hydroxy-1-[4-(phenoxy)piperazine-1-sulfonyl]piperidine-2-(R)-carboxamide. and where $R^{10}$ is —NHOH, $R^2$ is hydrogen, $R^1$ and $R^3$ together with the nitrogen atom to which they are attached form a piperazino ring substituted at the 4-position with N,N-dimethylaminocarbonyl and $R^{20}$ and $R^{21}$ together with the nitrogen atom to which they are attached form a 1,2,3,6-tetrahydropyridine substituted at the 4-position with 4-fluorophenyl, is named N-hydroxy-4-(N,N-dimethylaminocarbonyl)-1-[4-(4-fluorophenyl)-1,2,3,6-tetrahydropyridine-1-sulfonyl] piperazine-2-(R)-carboxamide.

Representative compounds of this invention are as follows:
I. Compounds of formula (I) where $R^2$ = hydrogen, $R^{10}$ = -$NR^{11}OR^{12}$ where $R^{11}$ and $R^{12}$ are hydrogen, and other groups are as defined below are:

| CPD # | Stereo-chem | $R^1$ | $R^3$ | -$NR^{20}R^{21}$ = heterocycloamino group | M.Pt. °C. | Mass Spec. |
|---|---|---|---|---|---|---|
| 1 | 2(R) | 2-propyl | benzyl | piperidino | 80.6–85.7 | 370 M + H |
| 2 | | H | benzyl | morpholino | | 329 M+ |
| 3 | | H | benzyl | 4-methoxypiperidino | | 357 M+ |
| 4 | | H | benzyl | 4-(4-chlorophenyl)piperazino | 75.6–76.9 | 439 M + H |
| 5 | | H | benzyl | 4-chloropiperidino | | 362 M + H |
| 6 | | H | benzyl | 4-phenoxypiperidino | | 420 M + H |
| 7 | | H | pyridin-3-ylmethyl | 4-(4-chlorophenyl)piperazino. TFA salt | 159.2–159.5 | 440 M + H |
| 8 | | H | H | 4-(4-chlorophenyl)piperazino | 151.3–152.1 | 348 M+ |
| 9 | | H | benzyl | 4-(4-trifluoromethylphenyl)piperazino | 49.7–51.4 | 472 M+ |
| 10 | | H | benzyl | 4-phenylpiperazino. TFA salt | 45.1–72.9 | 405 M + H |
| 11 | | H | benzyl | 4-(4-methoxyphenyl)piperazino. TFA salt | 46.4–67.5 | 435 M + H |
| 12 | | H | benzyl | 4-(4-fluorophenyl)piperazino. TFA salt | 126.7–127.3 | 422 M+ |
| 13 | | H | benzyl | 4-(pyridin-4-yl)piperazino | 87.5–122.5 | 405 M+ |
| 14 | 2(R) | methyl | benzyl | 4-(4-chlorophenyl)piperazino | 76.7–79.8 | 453 M + H |
| 15 | | H | methyl | 4-(4-chlorophenyl)piperazino. TFA salt | 141.2–143.2 | 363 M + H |
| 16 | | H | 2-methoxyethyl | 4-(4-chlorophenyl)piperazino. TFA salt | 54.1–57.7 | 406 M+ |
| 17 | | H | benzyl | 4-(4-methylphenyl)piperazino. TFA salt | 130.2–131.1 | 419 M + H |
| 18 | | H | benzyl | 4-cyclopentylpiperazino. TFA salt | 156.2–156.8 | 397 M + H |
| 19 | | H | benzyl | 4-(4-chlorophenoxy)piperidino | 39–47.7 | 454 M + H |
| 20 | 2(R) | methyl | H | 4-(4-chlorophenyl)piperazino | 143 | 362 M+ |
| 21 | 2(R) | methyl | H | 4-(4-chlorophenyl)piperazino. TFA salt | 99–101 | 363 M + H |
| 22 | 2(S) | methyl | H | 4-(4-chlorophenyl)piperazino | | 363.1 M + H |
| 23 | 2(RS) | methyl | H | 4-(4-chlorophenyl)piperazino | 75 efferves. | 363.2 M + H |
| 24 | | H | pyridin-3-ylmethyl | 4-phenoxypiperidino. TFA salt | 127.5–128.9 | 421 M + H |
| 25 | | H | H | 4-(4-fluorophenyl)piperazino. TFA salt | 51–54 | 333 M + H |
| 26 | | H | H | 4-phenylpiperazino. TFA salt | 123.1–126.1 | 315 M + H |
| 27 | | H | H | 4-(4-methoxyphenyl)piperazino. TFA salt | 119.4–120.9 | 343 M – H |
| 28 | | H | H | 4-(4-methylphenyl)piperazino. TFA salt | 62–76 | 329 M + H |
| 29 | | H | H | 4-(4-trifluoromethylphenyl)piperazino | 144–145 | 383 M + H |
| 30 | | H | H | 4-phenoxypiperidino | 110–114 | 330 M + H |
| 31 | | H | H | 4-(4-ethoxyphenyl)piperazino. TFA salt | 56–61.5 | 359 M + H |
| 32 | | H | H | 4-(2-chlorophenyl)piperazino | 165–165.5 | 347 M – H |
| 33 | | H | H | 4-(3-chlorophenyl)piperazino | 138.1–138.6 | 348 M+ |
| 34 | | H | H | 4-(4-nitrophenyl)piperazino | | 358 M – H |
| 35 | | H | H | 4-(4-benzyloxyphenyl)piperazino | 162 efferves. | 419 M – H |
| 36 | | H | H | 4-(4-phenoxyphenyl)piperazino | 131 efferves. | 407 M + H |
| 37 | | H | H | 4-(4-cyanophenyl)piperazino | 155–155.5 | 340 M + H |
| 38 | | H | H | 4-(4-biphenyl)piperazino | | 391.2 M + H |
| 39 | | H | H | 4-(3-methoxyphenyl)piperazino | 134.1–134.9 | 345 M + H |
| 40 | | H | H | 4-(3-trifluoromethylphenyl)piperazino | 110.9 efferves. | 382 M+ |
| 41 | 2(RS) | ethyl | H | 4-(4-chlorophenyl)piperazino | | 376 M+ |
| 42 | | H | H | 4-(pyridin-2-yl)piperazino | 75.1 efferves. | 316 M + H |
| 43 | | H | H | 4-[4-(1,1,2,2-tetrafluoroethoxyphenyl)-piperazino | 115–117.1 | 429 M – H |
| 44 | 2(RS) | n-butyl | H | 4-(4-chlorophenyl)piperazino | 156–156.4 | 404 M+ |
| 45 | | H | H | 4-(3-phenoxyphenyl)piperazino | 126.5 efferves. | 405 M – H |
| 46 | | H | H | 4-(3-benzyloxyphenyl)piperazino | 129–130 | 421 M + H |
| 47 | | H | H | 4-(pyrimidin-2-yl)piperazino | 144–145 | 316 M+ |
| 48 | 2(R) | methyl | H | 4-(5-chloropyridin-2-yl)piperazino | 102 efferves. | 363 M+ |
| 49 | 2(R) | methyl | H | 4-phenoxypiperidino | 55–62 | 344.1 M + H |
| 50 | 2(R) | 2-propyl | H | 4-(5-chloropyridin-2-yl)piperazino | 146.7–147 | 392.1 M + H |
| 51 | 2(R) | 2-propyl | H | 4-(4-chlorophenyl)piperazino | 154.1–154.8 | 391.1 M + H |
| 52 | 2(R) | tert-butyl | H | 4-(4-chlorophenyl)piperazino | 185–186 | 405.1 M + H |
| 53 | | H | H | 4-(pyridin-3-yl)piperazino | 179.3–179.6 | 316 M + H |
| 54 | | H | H | 4-(5-trifluoromethylpyridin-2-yl)-piperazino | 145.2–145.5 | 384 M + H |
| 55 | 2(R) | methyl | H | 4-(4-benzyloxy)piperidino | 68–71 | 358.1 M + H |
| 56 | 2(R) | methyl | H | 4-(3-phenylpropyloxy)piperidino | 89–93.5 | 386.1 M + H |
| 57 | 2(R) | methyl | H | 4-(4-chlorophenoxy)piperidino | 93–94 | 378.1 M + H |
| 58 | 2(R) | methyl | H | 4-(5-trifluoromethylpyridin-2-yl)-piperazino | 121.3–121.7 | 398 M + H |
| 59 | 2(R) | 2-propyl | H | 4-(4-chlorophenoxy)piperidino | 139.2–139.6 | 406.1 M + H |
| 60 | 2(R) | 2-propyl | H | 4-(5-trifluoromethylpyridin-2-yl)-piperazino | 158.3–158.8 | 426.1 M + H |
| 61 | 2(R) | tert-butyl | H | 4-(5-chloropyridin-2-yl)piperazino | 218.4–218.6 | 405 M + H |
| 62 | 2(R) | (1-methyl-1-methylthio)ethyl | H | 4-(4-chlorophenyl)piperazino | 158.5–159.6 | |
| 63 | | H | 3-phenylpropyl | 4-(pyridin-2-yl)piperazino | 58–59.5 | 434.1 M + H |
| 64 | | H | 3-phenylpropyl | 4-(pyridin-3-yl)piperazino | 64–65 | 434.1 M + H |
| 65 | 2(R) | methyl | H | 4-(benzylaminocarbonyl)piperidino | 85.9–87.9 | 385.1 M + H |
| 66 | 2(R) | methyl | H | 4-[(4-chlorobenzylaminocarbonyl)methyl]piperidino | 86.6–88.3 | 433.2 M + H |

-continued

Representative compounds of this invention are as follows:
I. Compounds of formula (I) where $R^2$ = hydrogen, $R^{10}$ = -$NR^{11}OR^{12}$ where $R^{11}$ and $R^{12}$ are hydrogen, and other groups are as defined below are:

| CPD # | Stereo-chem | $R^1$ | $R^3$ | -$NR^{20}R^{21}$ = heterocycloamino group | M.Pt. °C. | Mass Spec. |
|---|---|---|---|---|---|---|
| 67 | 2(R) | methyl | H | 4-(4-chlorobenzoyl)piperidino | 77.4–79.7 | 390 M + H |
| 68 | 2(R) | methyl | H | 4-(4-chlorobenzylcarbonyl)piperazino | 81.5–82.4 | 405.1 M + H |
| 69 | 2(R) | methyl | H | 4-(4-chlorobenzoyl)piperazino | 107.9 decomp. | 391.1 M + H |
| 70 | | H | H | 4-(phenylamino)piperidino. TFA salt | 55.8–57.2 | 329 M + H |
| 71 | 2(R) | methyl | H | 4-(benzyl)piperidino | 73 efferves. | 342.2 M + H |
| 73 | 2(R) | methyl | H | 4-(3-chlorophenoxy)piperidino | 90 efferves. | 378.1 M + H |
| 74 | 2(R) | 2-propyl | H | 4-(4-benzyloxyphenyl)piperazino | 149–156 | 463 M + H |
| 75 | 2(R) | 2-propyl | H | 4-(4-biphenyl)piperazino | 150.5 efferves. | 433.2 M + H |
| 76 | 2(R) | (1-methyl-1-methylthio)ethyl | H | 4-(4-chlorophenoxy)piperidino | 116.5–117.2 | |
| 77 | 2(R) | methyl | H | 4-(4-chlorophenylthio)piperidino | 114 efferves. | 392 M − H |
| 78 | 2(R) | 2-propyl | pyridin-3-ylmethyl | 4-(phenoxy)piperidino | 128.9 efferves. | 463.1 M + H |
| 79 | 2(R) | 2-propyl | H | 4-(phenoxy)piperidino | 65.8 efferves. | 372.2 M + H |
| 80 | 2(R) | H | 2-phenoxyethyl | 4-(pyridin-4-yl)piperazino | | 436.1 M + H |
| 81 | 2(RS) | benzyloxymethyl | H | 4-(5-chloropyridin-2-yl)piperazino | 82–89.7 | 470.1 M + H |
| 82 | 2(RS) | phenylethyl | methyl | 4-(5-chloropyridin-2-yl)piperazino | 145.9–146.8 | 468.1 M + H |
| 83 | 2(R) | 2-propyl | pyridin-3-ylmethyl | 4-(5-bromopyridin-2-yl)piperazino | | 527.1 M + H |
| 84 | 2(R) | 2-propyl | H | (4-benzyl-4-hydroxy)piperidino | 136.1–139 | 386 M + H |
| 85 | 2(R) | benzyl | H | 4-(4-chlorophenyl)piperazino | 167–168 | 439 M + H |
| 86 | 2(R) | 2-propyl | H | 4-[4-(pyridin-3-ylmethyloxy)phenyl]-piperazino | 177.5–177.8 | 464.1 M + H |
| 87 | 2(R) | methyl | H | 4-[1-(phenyl)hydroxymethyl]piperidino | 91.9–94.4 | 358 M + H |
| 88 | | H | H | 4-(4-nitrophenylamino)piperidino | | 374 M + H |
| 89 | | H | 2-phenoxyethyl | 4-(pyridin-2-yl)piperazino | 134–134.6 | 436.1 M + H |
| 90 | 2(RS) | benzyloxymethyl | methyl | 4-(5-chloropyridin-2-yl)piperazino | | 484.1 M + H |
| 91 | 2(RS) | 2-phenylethyl | H | 4-(5-chloropyridin-2-yl)piperazino | 125.5–128.1 | 454 M + H |
| 92 | 2(R) | 2-propyl | H | 4-(2-methylpyridin-5-yloxy)piperidino | 95 efferves. | 386 M+ |
| 93 | 2(R) | phenylthiomethyl | H | 4-(4-chlorobenzoyl)piperidino | | 498 M + H |
| 94 | 2(R) | methyl | ethyl | 4-(4-chlorobenzoyl)piperidino | | 418 M + H |
| 95 | | H | H | 4-phenylpiperidino | 147.3–147.6 | 314 M + H |
| 96 | 2(R) | 2-propyl | H | 4-{4-[(pyridin-4-ylmethyloxy)phenyl]}-piperazino | 171.8–172.1 | 464.1 M + H |
| 97 | 2(R) | methyl | H | 4-benzoylpiperidino | 94.2–102.9 | 356 M + H |
| 98 | 2(R) | 2-propyl | H | 4-benzoylpiperidino | 187.2–187.6 | 383 M+ |
| 99 | 2(R) | methyl | pyridin-3-ylmethyl | 4-(4-chlorobenzoyl)piperidino | | 481 M + H |
| 100 | 2(R) | 2-propyl | H | 4-(5-chloropyridin-2-yloxy)piperidino | 97–98.4 | 407 M + H |
| 101 | 2(R) | phenylthiomethyl | H | 4-(4-bromophenoxy)piperidino | | 530 M + H |
| 102 | 2(R) | benzylthiomethyl | H | 4-(5-chloropyridin-2-yl)piperazino | 86–86.7 | 486.1 M + H |
| 103 | 2(R) | 4-hydroxybenzyl | H | 4-(5-chloropyridin-2-yl)piperazino | 142 | 456.1 M + H |
| 104 | 2(R) | 2-propyl | pyridin-3-ylmethyl | 4-(4-bromophenoxy)piperidino | 143–146 | 541 M + H |
| 105 | 2(R) | 2-propyl | 3-(pyridin-3-yl)propyl | 4-(4-bromophenoxy)piperidino | | 569 M + H |
| 106 | 2(R) | phenylthiomethyl | H | 4-(5-chloropyridin-2-yl)piperazino | | 472 M + H |
| 107 | 2(R) | methyl | H | 4-(4-fluorobenzoyl)piperidino | 148.1–148.4 | 374 M + H |
| 108 | 2(RS) | 2-propenyl | H | 4-(5-chloropyridin-2-yl)piperazino | 59.8 | 390.1 M + H |
| 109 | 2(R) | 2-propyl | H | 4-(4-bromophenoxy)piperidino | | 450.06 M + H |
| 110 | 2(R) | phenylthiomethyl | methyl | 4-(4-chlorobenzoyl)piperidino | | 512.1 M + H |
| 111 | 2(R) | 2-propyl | H | 4-{4-[(pyridin-2-yl)methyloxy]phenyl}-piperazino | 124.2–128.5 | 464 M+ |
| 112 | 2(R) | methyl | H | 4-(4-methylbenzoyl)piperidino | 172.4 efferves. | 370 M + H |
| 113 | 2(R) | 2-propyl | H | 4-[4-(pyridin-3-yl)phenoxy]piperidino | 108.1–131 | 449 M + H |
| 114 | 2(R) | pyridin-2-ylthio-methyl | H | 4-(5-chloropyridin-2-yl)piperazino | 97.8 efferves. | 473.08 M + H |
| 115 | 2(R) | methyl | 3-phenylpropyl | 4-(4-chlorobenzoyl)piperidino | | 508 M + H |
| 116 | 2(R) | methyl | H | 4-(4-methoxybenzoyl)piperidino | 184.5 | 386 M + H |
| 117 | 2(R) | thiophen-2-ylthio-methyl | H | 4-(5-chloropyridin-2-yl)piperazino | 92.5–94.5 | 478 M + H |
| 118 | 2(R) | methyl | 2-N,N-dimethylamino-ethyl | 4-(4-chlorobenzoyl)piperidino | | 461 M + H |
| 119 | 2(R) | methyl | H | 4-(4-chlorophenylsulfonyl)piperazino | 180.5–180.9 | 427 M + H |
| 120 | 2(R) | 2-propyl | H | 4-(benzthiazol-2-yl)piperazino | 146–148 | 414.1 M + H |
| 121 | 2(R) | benzylthiomethyl | methyl | 4-(4-chlorobenzoyl)piperidino | | 526 M + H |
| 122 | 2(R) | 2-propyl | methyl | 4-(4-chlorobenzoyl)piperidino | 68.9 decomp. | |
| 123 | 2(R) | 2-propyl | methyl | 4-(benzoxazol-2-yl)piperazino | 78.5–80 | 411 M + H |
| 124 | 2(R) | 2-propyl | H | 4-(benzoxazol-2-yl)piperazino | 175.2–176.3 | 398 M + H |
| 125 | 2(S) | methyl | H | 4-(4-chlorobenzoyl)piperidino | 201.2–201.8 | |
| 126 | 2(R) | 2-propyl | H | 4-[4-(imidazol-1-yl)phenoxy]piperidino | 89.2 efferves. | 438.1 M + H |
| 127 | 2(R) | methyl | H | 4-(4-chlorophenyl)-4-hydroxy-piperidino | 75–77.5 | 378 M + H |
| 128 | 2(R) | 2-propyl | H | 4-(quinolin-6-yloxy)piperidino | 112–142 | 423.1 M + H |
| 129 | 2(R) | 2-propyl | H | 4-phenylpiperidino | 154.9–155.1 | 356.1 M + H |
| 130 | 2(R) | methyl | H | 4-(benzoxazol-2-yl)piperidino | 136 efferves. | 369.1 M + H |
| 131 | 2(R) | 2-propyl | H | 4-(benzimidazol-2-yl)piperidino | 143.7 efferves. | 396.1 M + H |
| 132 | 2(R) | methyl | H | 4-(4-fluorophenylaminocarbonyl) | 104.4–110.4 | 389.1 M + H |

-continued

Representative compounds of this invention are as follows:
I. Compounds of formula (I) where $R^2$ = hydrogen, $R^{10}$ = -$NR^{11}OR^{12}$ where $R^{11}$ and $R^{12}$ are hydrogen, and other groups are as defined below are:

| CPD # | Stereo-chem | $R^1$ | $R^3$ | -$NR^{20}R^{21}$ = heterocycloamino group | M.Pt. °C. | Mass Spec. |
|---|---|---|---|---|---|---|
| 133 | 2(R) | 2-propyl | H | 4-[4-phenylimidazol-2-yl]piperidino | 141–142.3 | 422 M + H |
| 134 | 2(R) | 2-propyl | H | 4-(4-chlorobenzoyl)piperidino | 181–182.5 | 418 M + H |
| 135 | 2(R) | methyl | H | 4-phenylpiperidino | 147.9–148.3 | 328 M + H |
| 136 | 2(R) | 2-propyl | H | 4-[5-phenylthiazol-2-yl]piperidino | 120–122.1 | 439 M + H |
| 137 | 2(R) | tert-butyl | H | 4-(5-chloropyridin-2-yloxy)piperidino | 235–235.2 | 405 M + H |
| 138 | 2(R) | 2-propyl | H | 4-(benzoxazol-2-yl)piperidino | 107–109.5 | 397.2 M + H |
| 139 | 2(R) | methyl | H | 4-(2,3,4,5,6-pentamethylbenzoyl)-piperidino | 128–132 | 426.2 M + H |
| 140 | 2(R) | benzylthiomethyl | H | 4-(4-chlorobenzoyl)piperidino | | 512 M + H |
| 141 | 2(R) | methyl | H | 4-(5-fluoroindol-3-yl)piperidino | | 384 M + H |
| 142 | 2(R) | methyl | H | 4-(6-fluorobenzisoxazol-3-yl)piperidino | | 387 M + H |
| 143 | 2(R) | methyl | H | 4-(4-chlorobenzoyloxime)piperidino | 109.3–131.3 | 405 M + H |
| 144 | 2(R) | methyl | H | 4-(1-benzimidazol-2-one)piperidino | | 384 M + H |
| 145 | 2(R) | methyl | H | 4-(2,4-difluorobenzoyl)piperidino | | 392.1 M + H |
| 146 | 2(R) | methyl | H | 4-(4-chlorophenylsulfonyl)piperidino | 158–158.3 | |
| 147 | 2(R) | methyl | H | 4-{[2-(4-chlorophenyl)-1,3-dioxolan-2-yl]}piperidino | 154.9–155.4 | 434 M + H |
| 148 | 2(R) | methyl | H | 4-[4-(phenoxy)benzoyl]piperidino | 202–205 | 448 M + H |
| 149 | 2(R) | methyl | H | 4-(3-chlorobenzoyl)piperidino | | 390.4 M + H |
| 150 | 2(R) | methyl | H | 4-(4-fluoro-3-methylbenzoyl)piperidino | | 388.2 M + H |
| 151 | 2(R) | methyl | H | 4-(4-trifluoromethylbenzoyl)piperidino | | 424.2 M + H |
| 152 | 2(R) | methyl | H | 4-(3-methylbenzoyl)piperidino | 115–116 | 370 M + H |
| 153 | 2(RS) | 3-phenylpropyl | H | 4-(5-chloropyridin-2-yl)piperazino | 123.3–124 | 468 M + H |
| 154 | 2(R) | methyl | H | 4-(benzimidazol-2-yl)piperazino | 108 | 369 M + H |
| 155 | 2(R) | methyl | H | 4-[1-(4-chlorophenyl)hydroxymethyl]-piperidino | 101.3–103.6 | 392 M + H |
| 156 | 2(R) | methyl | H | 4-(thiophen-2-ylcarbonyl)piperidino | 107.1–107.9 | 362 M + H |
| 157 | 2(R) | methyl | H | 4-(benzothiophen-2-ylcarbonyl)-piperidino | 100.1–111.1 | 412 M + H |
| 158 | 2(R) | methyl | H | 4-[(4-chloro-3-trifluoromethylbenzoyl)-piperidino | 95.5–98 | 458.1 M + H |
| 159 | 2(R) | methyl | H | 4-{[methyl-(4-chlorophenyl)]amino-carbonyl}piperazino | 79.1–90.2 | 420.2 M + H |
| 160 | 2(R) | methyl | H | 4-(4-tert-butylbenzoyl)piperidino | 79–84 | 412 M + H |
| 161 | 2(R) | methyl | H | 4-(2-methylbenzoyl)piperidino | 75–79 | 370 M + H |
| 162 | 2(R) | methyl | H | 4-(4-phenylbenzoyl)piperidino | 100 efferves. | 432 M + H |
| 163 | 2(R) | methyl | H | 4-(benzothiophen-3-yl)piperidino | | 384 M + H |
| 164 | 2(R) | methyl | H | 4-(morpholin-4-ylcarbonyl)piperidino | 88.5–93.5 | 365 M + H |
| 165 | 2(R) | methyl | H | 4-(6-chloroindol-3-yl)piperidino | 95 efferves. 115 liquid | 401 M + H |
| 166 | 2(R) | methyl | H | 4-(5-methylindol-3-yl)piperidino | 105 efferves. 150 liquid | 381 M + H |
| 167 | 2(R) | methyl | H | 4-(6-methylindol-3-yl)piperidino | 115–124 | 381.1 M + H |
| 168 | 2(R) | methyl | H | 4-(5-fluoro-1-methylindol-3-yl)-piperidino | | 399 M + H |
| 169 | 2(R) | methyl | H | 4-(4-methylsulfonylbenzoyl)piperidino | 88 efferves. | 434 M + H |
| 170 | 2(R) | 2-propyl | H | 4-(2-phenylbenzoxazol-5-yl)piperazino | 165.7–166 | 474 M + H |
| 171 | 2(R) | methyl | H | 4-(4-chloromethylthiobenzoyl)-piperidino | 95 efferves. | 436 M + H |
| 172 | 2(R) | methyl | H | 4-(4-methylthiobenzoyl)piperidino | | 402 M + H |
| 173 | 2(R) | methyl | H | 4-(benzylcarbonyl)piperidino | 61–65 | 370.1 M + H |
| 174 | 2(R) | methyl | H | 4-(pyridin-2-ylcarbonyl)piperidino. HCl salt | 155 efferves. | 357 M + H |
| 175 | 2(R) | methyl | H | 4-(pyridin-3-ylcarbonyl)piperidino. HCl salt | 137–147 | 357.12 M + H |
| 176 | 2(R) | methyl | H | 4-(indol-3-yl)piperidino | 163.3–164.1 | 367.2 M + H |
| 177 | 2(R) | methyl | H | 4-(4-chlorophenylaminocarbonyl)-piperazino | | 406.09 M + H |
| 178 | 2(R) | tert-butyl | H | 4-(5-bromopyridin-2-yl)piperazino | 144–146.5 | 452 M + H |
| 179 | 2(R) | 2-propyl | H | 4-(4-fluorophenoxy)piperidino | 74.3–75.3 | 390 M + H |
| 180 | 2(R) | methyl | H | 3-(4-chlorobenzoyl)piperidino | 89–93.5 | 390 M + H |
| 181 | 2(R) | methyl | H | 4-(pyridin-4-ylcarbonyl)piperidino. HCl salt | 153 efferves. | 357.12 M + H |
| 182 | | H | H | 4-phenylpiperidino | 160–162 | 378.1 M + H |
| 183 | 2(R) | 2-propyl | H | 4-(6-chloropyridin-2-yloxy)piperidino | 81–96 | 407.1 M + H |
| 184 | 2(R) | methyl | H | 4-(naphth-2-yl)piperidino | 160–162 | 378.1 M + H |
| 185 | 2(R) | 2-propyl | H | 4-(4-chlorophenyl)piperidino | 154.3–154.8 | 389 M+ |
| 186 | 2(R) | tert-butyl | H | 4-[5-(thiophen-2-yl)pyridin-2-yl]-piperazino | 151.5–152.5 | 454 M + H |
| 187 | 2(R) | 2-propyl | H | 4-(6-methylpyridin-2-yloxy)piperidino | 147.4–148.9 | 387 M + H |
| 188 | | H | H | 4-(4-chlorobenzoyl)piperidino | | 376 M + H |

-continued

Representative compounds of this invention are as follows:
I. Compounds of formula (I) where $R^2$ = hydrogen, $R^{10}$ = $-NR^{11}OR^{12}$ where $R^{11}$ and $R^{12}$ are hydrogen, and other groups are as defined below are:

| CPD # | Stereo-chem | $R^1$ | $R^3$ | $-NR^{20}R^{21}$ = heterocycloamino group | M.Pt. °C. | Mass Spec. |
|---|---|---|---|---|---|---|
| 189 | 2(R) | tert-butyl | H | 4-(4-chlorobenzoyl)piperidino | 171.6–172.1 | 432 M + H |
| 190 | 2(R) | 2-propyl | H | 4-(4-chlorophenylthio)piperidino | 117.9–119.8 | 421 M+ |
| 191 | 2(R) | 2-propyl | H | 4-(6-chloroindol-3-yl)piperidino | 112.1–115.4 | 429 M + H |
| 192 |  | H | 3-methylbutyl | 4-phenylpiperidino |  | 383 M + H |
| 193 | 2(RS) | H | 2-phenoxyethyl | 4-phenylpiperidino |  | 433 M + H |
| 194 | 2(RS) | H | methyl | 4-phenylpiperidino |  | 327 M + H |
| 195 | 2(RS) | H | 2-methoxyethyl | 4-phenylpiperidino |  | 371 M + H |
| 196 | 2(RS) | H | 2-N,N-dimethyl-aminoethyl | 4-phenylpiperidino |  |  |
| 197 | 2(R) | 1-(R)-methylpropyl | H | 4-(5-chloropyridin-2-yloxy)piperidino | 132.3–133.1 | 421 M + H |
| 198 | 2(R) | 1-(S)-(tert-butoxy)-ethyl | H | 4-(5-chloropyridin-2-yloxy)piperidino | 149.6–153.3 | 465.2 M + H |
| 199 | 2(R) | 2-methylpropyl | H | 4-(5-chloropyridin-2-yloxy)piperidino | 198.2–200 | 405.1 M + H |
| 200 | 2(R) | 1-(S)-hydroxyethyl | H | 4-(5-chloropyridin-2-yloxy)piperidino | 86.5–89 | 409 M + H |
| 201 | 2(R) | 1-(S)-methylpropyl | H | 4-(5-chloropyridin-2-yloxy)piperidino | 66.2–73.2 | 421.1 M + H |
| 202 | 2(R) | 2,2-dimethylpropyl | H | 4-(5-chloropyridin-2-yloxy)piperidino | 117.2–117.7 | 435.1 M + H |
| 203 | 2(R) | methyl | H | 4-(benzothiophen-2-yl)piperidino |  | 384 M + H |
| 204 | 2(S) | methyl | H | 4-(4-chlorobenzoyl)piperidino | 201.2–201.8 |  |
| 205 | 2(R) | methyl | H | 4-(quinolin-3-yl-N-oxide)piperidino |  | 395 M + H |
| 206 | 2(R) | methyl | H | 4-(4-chlorobenzoyl)-4-hydroxypiperidino |  | 406 M + H |
| 207 | 2(R) | cyclohexyl | H | 4-(5-chloropyridin-2-yloxy)piperidino | 171.1–171.4 | 447 M + H |
| 208 | 2(R) | 2-propyl | H | 4-(5-nitropyridin-2-yl)piperazino | 92.8 efferves. | 403 M + H |
| 209 | 2(R) | tert-butoxymethyl | H | 4-(5-chloropyridin-2-yloxy)piperidino | 162.5–163 | 451 M + H |
| 210 | 2(R) | methyl | H | 4-(4-fluorobenzylaminocarbonyl)-piperazino | 110–123 | 404 M + H |
| 211 | 2(R) | 2-propyl | pyridin-3-ylmethyl | 4-(5-chloropyridin-2-yloxy)piperidino | 152.2–152.7 | 498 M + H |
| 212 | 2(R) | 2-propyl | pyridin-3-ylmethyl | 4-(4-chlorophenoxy)piperidino | 140.9–142.1 | 497 M + H |
| 213 | 2(R) | methyl | H | 4-[4-(phenoxy)phenylaminocarbonyl]-piperazino | 119–122 | 464 M + H |
| 214 | 2(R) | methyl | H | 4-(4-biphenylaminocarbonyl)piperazino | 110–135 | 448 M + H |
| 215 | 2(R) | methyl | H | 4-[4-(benzyloxy)phenylaminocarbonyl]-piperazino |  | 478.1 M + H |
| 216 | 2(R) | methyl | H | 4-(naphth-1-yl)piperidino | 164.2–165 | 378 M + H |
| 217 | 2(R) | 2-methylpropyl | H | 4-(5-chloropyridin-2-yl)piperazino | 83–88 | 406.2 M + H |
| 218 | 2(R) | tert-butoxymethyl | H | 4-(5-chloropyridin-2-yl)piperazino | 74–77.5 | 436.2 M + H |
| 219 | 2(R) | propyl | H | 4-(4-chlorophenyl)piperazino | 142.4–142.9 | 391.2 M + H |
| 220 | 2(R) | benzyl | H | 4-(5-chloropyridin-2-yloxy)piperidino | 76.2–79.5 | 455.1 M + H |
| 221 | 2(R) | 2-propyl | H | 4-(4-chlorophenylaminocarbonyl)-piperazino | 115–128 | 434.1 M + H |
| 222 | 2(R) | 2-propyl | pyridin-3-ylmethyl | 4-(4-chlorobenzoyl)piperidino | 151.6–152.6 | 509.1 M + H |
| 223 | 2(R) | 2-propyl | H | 4-(cyanophenyl)piperazino | 76.5–80 efferves. | 382 M + H |
| 224 | 2(R) | n-propyl | H | 4-(5-chloropyridin-2-yl)piperazino |  | 392.2 M + H |
| 225 | 2(RS) | phenyl | H | 4-(5-chloropyridin-2-yloxy)piperidino | 85.1–89.4 | 441.2 M + H |
| 226 | 2(R) | 2-propyl | H | 4-(4-fluorobenzoyl)piperidino | 171.5–172.4 | 402 M + H |
| 227 | 2(R) | methyl | H | 8-chloro-1,2,3,4-tetrahydro-γ-carbolino | 97.4–108 | 373 M + H |
| 228 | 2(R) | methyl | (diphenylmethyl)ethyl | 4-(chlorobenzoyl)piperidino |  | 584.1 M + H |
| 229 | 2(RS) | H | phenyl | 4-(5-chloropyridin-2-yloxy)piperidino | 61–64 | 441 M + H |
| 230 | (R) | 4-fluorophenyl | H | 4-(4-fluorophenyl)piperidino | 90–92 | 426 M + H |
| 231 | (R) | 4-(benzyloxycarbo-nylamino)butyl | H | 4-(4-chlorophenyl)piperazino | 65–69 | 554.2 M + H | and are named as:
1. N-hydroxy-2-(R)-[benzyl-(piperidine-1-sulfonyl)amino]-3-methylbutyramide.
5. N-hydroxy-2-[benzyl-(4-chloropiperidine-1-sulfonyl)amino]acetamide.
15. N-hydroxy-2-(RS)-{methyl-[4-(4-chlorophenyl)piperazine-1-sulfonyl]amino}acetamide trifluoroacetate salt.
23. N-hydroxy-2-{[4-(4-chlorophenyl)piperazine-1-sulfonyl]amino}propionamide.
33. N-hydroxy-2-{[4-(3-chlorophenyl)piperazine-1-sulfonyl]amino}acetamide.
41. N-hydroxy-2-(RS)-{[4-(4-chlorophenyl)piperazine-1-sulfonyl]amino}butyramide.
50. N-hydroxy-2-(R)-{[4-(5-chloropyridin-2-yl)piperazine-1-sulfonyl]amino}-3-methylbutyramide.
51. N-hydroxy-2-(R)-{[4-(4-chlorophenyl)piperazine-1-sulfonyl]amino}-3-methylbutyramide.
54. N-hydroxy-2-[4-(5-trifluoromethylpyridin-2-yl)piperazine-1-sulfonyl]amino]acetamide.
57. N-hydroxy-2-(R)-{[4-(4-chlorophenoxy)piperidine-1-sulfonyl]amino}propionamide.
59. N-hydroxy-2-(R)-{[4-(4-chlorophenoxy)piperidine-1-sulfonyl]amino}-3-methylbutyramide.
62. N-hydroxy-2-(R)-{[4-(4-chlorophenyl)piperazine-1-sulfonyl]amino}-3-methyl-3-methylthiobutyramide.
66. N-hydroxy-2-(R)-{[4-(4-chlorobenzylcarbamoyl)methyl]piperidine-1-sulfonyl]amino}propionamide.
74. N-hydroxy-2-(R)-{[4-(4-benzyloxyphenyl)piperazine-1-sulfonyl]amino}-3-methylbutyramide.
78. N-hydroxy-2-(R)-{pyridin-3-ylmethyl-[4-(phenoxy)piperidine-1-sulfonyl]amino}-3-methylbutyramide.
84. N-hydroxy-2-(R)-{[(4-benzyl-4-hydroxy)piperidine-1-sulfonyl]amino}-3-methylbutyramide.
90. N-hydroxy-2-(RS)-{methyl-[4-(5-chloropyridin-2-yl)piperazine-1-sulfonyl]amino}-3-benzyloxypropionamide.
93. N-hydroxy-2-(R)-{[4-(4-chlorobenzoyl)piperidine-1-sulfonyl]amino}-3-phenylthiopropionamide.
96. N-hydroxy-2-(R)-{[4-[4-(pyridin-4-ylmethyloxy)phenyl]piperazine-1-sulfonyl]amino}-3-methylbutyramide.
100. N-hydroxy-2-(R)-{[4-(5-chloropyridin-2-yloxy)piperidine-1-sulfonyl]amino}-3-methylbutyramide.
103. N-hydroxy-2-(R)-{[4-(5-chloropyridin-2-yl)piperazine-1-sulfonyl]amino}-3-(4-hydroxyphenyl)propionamide.

-continued

Representative compounds of this invention are as follows:
I. Compounds of formula (I) where $R^2$ = hydrogen, $R^{10}$ = -$NR^{11}OR^{12}$ where $R^{11}$ and $R^{12}$ are hydrogen, and other groups are as defined below are:

| CPD # | Stereo-chem | $R^1$ | $R^3$ | -$NR^{20}R^{21}$ = heterocycloamino group | M.Pt. °C. | Mass Spec. |
|---|---|---|---|---|---|---|

114. N-hydroxy-2-(R)-{[4-(5-chloropyridin-2-yl)piperazine-1-sulfonyl]amino}-3-(pyridin-2-ylthio)propionamide.
125. N-hydroxy-2-(S)-{[4-(4-chlorobenzoyl)piperidine-1-sulfonyl]amino}propionamide.
136. N-hydroxy-2-(R)-{[4-(5-phenylthiazol-2-yl)piperidine-1-sulfonyl]amino}-3-methybutyramide.
148. N-hydroxy-2-(R)-{[4-(4-phenoxybenzoyl)piperidine-1-sulfonyl]amino}propionamide.
159. N-hydroxy-2-(R)-{[4-(methyl-4-chlorobenzoylaminocarbonyl)piperazine-1-sulfonyl]amino}propionamide
170. N-hydroxy-2-(R)-{[4-(2-phenylbenzoxazol-5-yl)piperazine-1-sulfonyl]amino}-3-methybutyramide.
183. N-hydroxy-2-(R)-{[4-(6-chloropyridin-2-yloxy)piperidine-1-sulfonyl]amino}-3-methybutyramide.
196. N-hydroxy-2-(RS)-{2-N,N-dimethylaminoethyl-[4-(phenyl)piperidine-1-sulfonyl]amino}acetamide.
207. N-hydroxy-2-(R)-{[4-(5-chloropyridin-2-yloxy)piperidine-1-sulfonyl]amino}-2-cyclohexylacetamide.
213. N-hydroxy-2-(R)-{[4-(4-phenoxyphenylaminocarbonyl)piperazine-1-sulfonyl]amino}propionamide.
224. N-hydroxy-2-(R)-{[4-(5-chloropyridin-2-yl)piperazine-1-sulfonyl]amino}valeramide.
230 N-hydroxy-2-(R)-{[4-(4-fluorophenyl)piperidine-1-sulfonyl]amino}-2-(4-fluorophenyl)acetamide.

II. Compounds of formula (I) where $R^2$ = hydrogen, $R^{10}$ = —$NR^{11}OR^{12}$ where $R^{11}$ and $R^{12}$ are hydrogen, and other groups are as defined below are:

| CPD # | Stereo-chem | $R^1CNR^3$ | —$NR^{20}R^{21}$ = heterocycloamino group | M.Pt °C. | Mass Spec. |
|---|---|---|---|---|---|
| 232 | 2(R) | piperidino | pyrrolidino | 142–144 | |
| 233 | 2(RS) | piperidino | piperidino | 123–125 | |
| 234 | 2(RS) | piperidino | 4-(4-chlorophenyl)piperazino | | 403 M + H |
| 235 | 2(R) | piperidino | 4-(4-fluorophenyl)piperazino | 105–107 | |
| 236 | 2(RS) | piperidino | 4-benzylpiperazino | 138–141 | |
| 237 | 2(RS) | piperidino | 4-(pyridin-2-yl)piperazino | | 370 M + H |
| 238 | 2(RS) | piperidino | 4-phenoxypiperidino | 106–108 | |
| 239 | 2(RS) | piperidino | 4-phenylthiopiperidino | | 400.13 |
| 240 | 2(RS) | piperidino | 4-(pyridin-4-ylthio)piperidino | | 401.13 |
| 241 | 2(RS) | piperidino | 4-(pyridin-2-ylthio)piperidino | | |
| 242 | 2(R) | piperidino | 4-(4-chlorobenzoyl)piperidino | 84.4–86.4 | 430 M + H |
| 243 | 2(R) | pyrrolidino | 4-(4-chlorobenzoyl)piperidino | | 416 M + H |
| 244 | 2(S) | 2,2-dimethylthiomorpholino | 4-(4-chlorobenzoyl)piperidino | | 476.1 M + H |
| 245 | 2(R) | piperidino | 4-(pyridin-4-ylthio)piperidino | | 401.1 M+ |
| 246 | 2(RS) | piperidino | 4-(phenylthio)piperidino | | 400.1 M+ |
| 247 | 2(R) | 3-(S)-(methoxycarbonyl)piperidino | 4-(4-chlorobenzoyl)piperidino | | 488 M + H |
| 248 | 2(S) | 2,2-dimethylthiomorpholino | 4-(5-chloropyridin-2-yl)piperazino | 126–131 | 450.1 M + H |
| 249 | 2(RS) | 1,2,3,4-tetrahydroisoquinolino | 4-(4-chlorophenyl)piperazino | 166.6–167.4 | 452.1 M + H |
| 250 | 2(RS) | piperazino | 4-(4-chlorobenzoyl)piperidino. TFA salt | | 431 M + H |
| 251 | 2(RS) | 4-(cyclopropylmethyl)piperazino | 4-(4-chlorobenzoyl)piperidino | | 485 M + H |
| 252 | 2(R) | 3-azabicycl[3.1.0]-cyclohexyl | 4-(4-chlorobenzoyl)piperidino | | 428 M + H |
| 253 | 2(RS) | 4-(2-N,N-dimethylaminoethyl)-piperazino | 4-(4-chlorobenzoyl)piperidino | | 502.2 M + H |
| 254 | 2(RS) | piperidino | 4-(5-fluoroindol-3-yl)piperidino | | 425 M + H |
| 255 | 2(RS) | 4-acetylpiperazino | 4-(4-chlorobenzoyl)piperidino | | 473 M + H |
| 256 | 2(RS) | piperidino | 4-(6-chloroindol-3-yl)piperidino | 143–151 | 441 M + H |
| 257 | 2(R) | piperidino | 4-(4-bromobenzoyl)piperidino | | 474 M + H |
| 258 | 2(RS) | 4-(pyridin-2-ylcarbonyl)piperazino | 4-(4-chlorobenzoyl)piperidino | | 536.2 M + H |
| 259 | 2(RS) | 4-(thiophen-2-ylcarbonyl)piperazino | 4-(4-chlorobenzoyl)piperidino | | 541 M + H |
| 260 | 2(RS) | 4-(benzylaminocarbonyl)piperazino | 4-(4-chlorobenzoyl)piperidino | | 564.2 M + H |
| 261 | 2(RS) | 4-cyclohexanoylpiperazino | 4-(4-chlorobenzoyl)piperidino | | 541.1 M + H |
| 262 | 2(RS) | 4-formylpiperazino | 4-(4-chlorobenzoyl)piperidino | | 459 M + H |
| 263 | 2(RS) | 4-(pyrrolidin-2-one-5-carbonyl)-piperazino | 4-(4-chlorobenzoyl)piperidino | | 542 M + H |
| 264 | 2(RS) | 4-[2-(S)-amino-3-methylbutanoyl]-piperazino | 4-(4-chlorobenzoyl)piperidino TFA salt | | 530 M + H |
| 265 | 2(RS) | 4-(N-methylaminocarbonyl)piperazino | 4-(4-chlorobenzoyl)piperidino | | 488 M + H |
| 266 | 2(RS) | 4-propanoylpiperazino | 4-(4-chlorobenzoyl)piperidino | | 487.1 M + H |
| 267 | 2(R) | morpholino | 4-(4-chlorobenzoyl)piperidino | 119–123.9 | 432.1 M + H |
| 268 | 2(R) | 1,2,3,4-tetrahydroisoquinolino | 4-(4-chlorobenzoyl)piperidino | | 478 M + H |
| 269 | 2(RS) | 4-(phenylaminocarbonyl)piperazino | 4-(4-chlorobenzoyl)piperidino | | 550 M + H |
| 270 | 2(RS) | piperidino | isoindolin-2-yl | 118–121 | |
| 271 | 2(R) | piperidino | 8-fluoro-1,2,3,4-tetrahydro-β-carbolino | | |
| 272 | 2(RS) | piperidino | 4-(5-chlorobenzimidazol-1-yl)piperidino | | 442 M + H |
| 273 | 2(RS) | piperidino | 4-(5-chloroindol-3-yl)piperidino | 117.8–143.9 | 441 M + H |
| 274 | 2(RS) | piperidino | 4-(5-chlorobenzotriazol-1-yl)piperidino | | 443 M + H |
| 275 | 2(RS) | 4-(benzyloxycarbonyl)piperazino | 4-(5-fluoroindol-3-yl)piperidino | 85.7–89.7 | 560 M + H |
| 276 | 2(RS) | 4-(benzyloxycarbonyl)piperazino | 4-(6-chloroindol-3-yl)piperidino | 98.2–102.2 | 576 M + H |
| 277 | 2(RS) | 4-acetylpiperazino | 4-(6-methylindol-3-yl)piperidino | | 464 M + H |
| 278 | 2(RS) | 4-(methoxycarbonylmethyl)piperazino | 4-(4-chlorobenzoyl)piperidino | | 503 M + H |
| 279 | 2(RS) | piperidino | 4-(5-fluoroindol-3-ylcarbonyl)piperidino | | |

-continued

II. Compounds of formula (I) where $R^2$ = hydrogen,
$R^{10}$ = —$NR^{11}OR^{12}$ where $R^{11}$ and $R^{12}$ are hydrogen,
and other groups are as defined below are:

| CPD # | Stereo-chem | $R^1CNR^3$ | —$NR^{20}R^{21}$ = heterocycloamino group | M.Pt ° C. | Mass Spec. |
|---|---|---|---|---|---|
| 280 | 2(RS) | piperidino | 4-(6-chloropyridin-2-yloxy)piperidino | 129.2–129.4 | 419 M + H |
| 281 | 2(RS) | piperidino | 4-(5-chloropyridin-2-yloxy)piperidino | 141.1–141.8 | 419 M + H |
| 282 | 2(RS) | piperidino | 4-(5-chloropyridin-2-yl)piperazino | 127.2–131.6 | 404 M + H |
| 283 | 2(RS) | 4-(aminomethylcarbonyl)piperazino | 4-(4-chlorobenzoyl)piperidino TFA salt | | 488 M + H |
| 284 | 2(RS) | 4-(methoxycarbonyl)piperazino | 4-(4-chlorobenzoyl)piperidino | | 489 M + H |
| 285 | 2(RS) | piperidino | 4-(4-chloroindol-3-yl)piperidino | 143–147 | 441 M + H |
| 286 | 2(RS) | piperidino | 4-(6-fluorobenzisoxazol-3-yl)piperidino | 145.8–146.9 | 427.1 M + H |
| 287 | 2(R) | piperidino | 4-(6-fluoroindol-3-yl)piperidino | 110–144.2 | 425 M + H |
| 288 | 2(RS) | piperidino | 4-(5-methoxyindol-3yl)piperidino | | 437 M + H |
| 289 | 2(RS) | piperidino | 4-(4-chloro-2-methyl)piperazino | 156–158.5 | 416 M+ |
| 290 | 2(RS) | 4-formylpiperazino | 4-(4-methylbenzoyl)piperidino | | 439.2 M + H |
| 291 | 2(RS) | piperidino | 4-(2,3-dimethylphenyl)piperazino | 128–129.5 | 397 M + H |
| 292 | 2(RS) | piperidino | 4-(5-hydroxyindol-3-yl)piperidino | | 423 M + H |
| 293 | 2(RS) | piperidino | 4-(4-chloro-3-trifluoromethylphenyl)-piperidino | 135.4–136 | 470 M + H |
| 294 | 2(R) | piperidino | 4-(5-cyanoindol-3-yl)piperidino | | 432 M + H |
| 295 | (RS) | piperidino | 4-[(6-fluoroisothiazol-3-yl)piperidino | 170.8–172 | 443 M + H |
| 296 | (RS) | piperidino | 4-(5-chloroindol-1-yl)piperidino | | 441 M + H |
| 297 | (RS) | piperidino | 4-(6-chlorobenz-1,2,3-triazol-1-yl)-piperidino | 165–167 | 443 M + H |
| 298 | (R) | 4-(N,N-dimethylaminocarbonyl)-piperazino | 4-(4-chlorobenzoyl)piperidino | | 502 M + H |
| 299 | (R) | piperidino | 4-(4,5,6,7-tetrafluoroindol-3-yl)piperidino | | 479.13 M + H |
| 300 | (RS) | piperidino | 4-(diphenylmethyl)piperidino | 103.7–145 | 458.21 M + H |
| 301 | (RS) | piperidino | 4-(6-chlorobenzimidazol-1-yl)piperidino | 128.8–132.4 | 442 M + H |
| 302 | (RS) | 4-(tert-butylaminocarbonyl)piperazino | 4-(5-fluoroindol-3-yl)piperidino | | 525.22 M + H |
| 303 | (RS) | 4-(benzyloxycarbonyl)piperazino | 4-(1-trimethylsilylethylsulfonyl-4,5,6,7-tetrafluoroindol-3-yl)piperidino | 124.8–130.4 | 778.2 M + H |
| 304 | (RS) | 4-(benzyloxycarbonyl)piperazino | 4-(4,5,6,7-tetrafluoroindol-3-yl)piperidino | 151.5–157.7 | 614.16 M + H |
| 305 | (RS) | 4-methoxycarbonylpiperazino | 4-(5-fluoroindol-3-yl)piperidino | 141.2–148.7 | 484.16 M + H |
| 306 | (RS) | 4-(tetrahydropyran-4-ylcarbonyl)-piperazino | 4-(5-fluoroindol-3-yl)piperidino | 141–200 | 538.21 M + H |
| 307 | (R) | piperidino | 4-(5-acetylaminoindol-3-yl)piperidino | 142–145 | 464 M + H |
| 308 | (RS) | 4-[2(S)-amino-3-methylbutyryl]-piperazino | 4-(6-fluoroindol-3-yl)piperidino | | 525 M + H |
| 309 | (R) | 4-(N,N-dimethylaminocarbonyl)-piperazino | 4-(4,5,6,7-tetrafluoroindol-3-yl)piperidino | 181–184 | 551.17 M + H |
| 310 | (R) | 4-(cyclopropylmethyl)piperazino | 4-(6-fluoroindol-3-yl)piperidino | | 480.20 M + H |
| 311 | (RS) | 4-(N,N-dimethylaminosulfonyl)-piperazino | 4-(5-fluoroindol-3-yl)piperidino | 111.5–113.7 | 533 M + H |
| 312 | (RS) | 4-[bis(N,N-dimethylamino)-phosphoryl]piperazino | 4-(6-fluoroindol-3-yl)piperidino | | 560.22 M + H |
| 313 | (R) | 4-(N,N-dimethylaminocarbonyl)-piperazino | 4-(4-fluorophenyl)piperidino | 89.8–112.5 | 458 M + H |
| 314 | (R) | piperidino | 1,2,3,4-tetrahydro-β-carbolino | 92.2–141.7 | 379 M + H |
| 315 | (R) | 4-(N,N-dimethylaminosulfonyl)-piperazino | 4-(4-chlorobenzoyl)piperidino | | 538.11 M + H |
| 316 | (R) | 4-(morpholin-4-ylcarbonyl)piperazino | 4-(4-chlorobenzoyl)piperidino | | 544.16 M + H |
| 317 | (R) | 4-(N-tert-butylaminocarbonyl)-piperazino | 4-(5-cyanoindol-3-yl)piperidino | 142–200 decomp. | 352.23 M + H |
| 318 | (R) | piperidino | 4-[5-(4-chlorophenyl)pyrrol-2-yl]piperidino | 91.4–122.4 | 467 M + H |
| 319 | (R) | 4-(1,4-pyrazin-2-ylcarbonyl)piperazino | 4-(4-chlorobenzoyl)piperidino | | 538.13 M + H |
| 320 | (R) | 4-(pyridin-3-ylmethyl)piperazino | 4-(4-chlorobenzoyl)piperidino | | 522.15 M + H |
| 321 | (R) | 4-(morpholin-4-ylcarbonyl)piperazino | 4-(5-cyanoindol-3-yl)piperidino | 144–200 | 546.21 M + H |
| 322 | (RS) | 4-(2,2,2-trifluoroethyl)piperazino | 4-(4-fluorophenyl)piperidino | 142.1–143.4 | 469 M + H |
| 323 | (R) | 4-(aminocarbonylmethyl)piperazino | 4-(4-chlorobenzoyl)piperidino | | 488.13 M + H |
| 324 | (R) | piperidino | 4-(5-cyano-1-methylsulfonylindol-3-yl)-piperidino | 143.3–143.9 | 510.1 M + H |
| 325 | (R) | 2,2,-dimethylthiomorpholino | 4-(5-cyanoindol-3-yl)piperidino | | 478 M + H |
| 326 | (R) | piperidino | 3-(4-chlorophenoxy)azetidino | | 397.13 M + H |
| 327 | (R) | piperidino | 4-(5-fluoro-2-hydroxylaminobenzoyl)-piperidino | | 457.15 M + H |
| 328 | (RS) | piperidino | 4-(2-amino-5-fluorobenzoyl)piperidino | | 429.16 M + H |
| 329 | (R) | piperidino | 4-[1-(4-fluorophenyl)pyrrol-3-yl]piperidino | | 451 M + H |
| 330 | (R) | 4-(1,4-pyrazin-2-ylcarbonyl)piperazino | 4-(5-cyanoindol-3-yl)piperidino | | 537 M − H |
| 331 | (R) | 4-(S)-hydroxypiperidino | 4-(4-chlorobenzoyl)piperidino | | 446 M + H |
| 332 | 2(RS) | 4-benzyloxycarbonylpiperazino | 4-(6-chloroindol-3-yl)piperidino | 98.2–102.2 | |
| 333 | 2(RS) | 4-benzyloxycarbonylpiperazino | 4-(1-trimethylsilylethylsulfonyl-6-chloroindol-3-yl)piperidino | 104.2–108.2 | |
| 334 | 2(RS) | 4-benzyloxycarbonylpiperazino | 4-(1-trimethylsilylethylsulfonyl-6-fluoroindol-3-yl)piperidino | 98.4–103.7 | |

-continued

II. Compounds of formula (I) where $R^2$ = hydrogen,
$R^{10}$ = —$NR^{11}OR^{12}$ where $R^{11}$ and $R^{12}$ are hydrogen,
and other groups are as defined below are:

| CPD # | Stereo-chem | $R^1CNR^3$ | —$NR^{20}R^{21}$ = heterocycloamino group | M.Pt ° C. | Mass Spec. |
|---|---|---|---|---|---|
| 335 | 2(RS) | 4-benzyloxycarbonylpiperazino | 4-(5-fluoroindol-3-yl)piperidino | 85.7–89.7 | |
| 336 | 2(RS) | 4-acetylpiperazino | 4-(6-methylindol-3-yl)piperidino | | | and are named as:
232. N-hydroxy-1-(pyrrolidine-1-sulfonyl)piperidine-2-(R)-carboxamide.
234. N-hydroxy-1-[4-(4-chlorophenyl)piperazine-1-sulfonyl]piperidine-2-(RS)-carboxamide.
237. N-hydroxy-1-[4-(pyridin-2-yl)piperazine-1-sulfonyl]piperidine-2-(RS)-carboxamide.
238. N-hydroxy-1-[4-(4-phenoxy)piperidine-1-sulfonyl]piperidine-2-(RS)-carboxamide.
239. N-hydroxy-1-[4-(4-phenylthio)piperidine-1-sulfonyl]piperidine-2-(RS)-carboxamide.
240. N-hydroxy-1-[4-(pyridin-4-ylthio)piperidine-1-sulfonyl]piperidine-2-(RS)-carboxamide.
249. N-hydroxy-1-[4-(4-chlorophenyl)piperazine-1-sulfonyl]-1,2,3,4-tetrahydroisoquinoline-2-(RS)-carboxamide.
258. N-hydroxy-1-[4-(4-chlorophenyl)piperidine-1-sulfonyl]-4-(pyridin-2-ylcarbonyl)piperazine-2-(RS)-carboxamide.
267. N-hydroxy-1-[4-(4-chlorobenzoyl)piperidine-1-sulfonyl]morpholine-2-(R)-carboxamide.
277. N-hydroxy-4-acetyl-1-[4-(6-methylindol-3-yl)piperidine-1-sulfonyl]piperazine-2-(RS)-carboxamide.
289. N-hydroxy-1-[4-(4-chloro-2-methyl)piperazine-1-sulfonyl]piperidine-2-(RS)-carboxamide.
299. N-hydroxy-1-[4-(4,5,6,7-tetrafluoroindol-3-yl)piperidine-1-sulfonyl]piperidine-2-(R)-carboxamide.
310. N-hydroxy-4-cyclopropylmethyl-1-[4-(6-fluoroindol-3-yl)piperidine-1-sulfonyl]piperazine-2-(R)-carboxamide.
321. N-hydroxy-4-(morpholin-4-ylcarbonyl)-1-[4-(5-cyanoindol-3-yl)piperidine-1-sulfonyl]piperazine-2-(R)-carboxamide.
331. N-hydroxy-1-[4-(4-chlorobanzoyl)piperidine-1-sulfonyl]-4-(S)-hydroxypiperidine-2-(R)-carboxamide.

III. Compounds of formula (I) where $R^3$ = hydrogen,
$R^{10}$ = —$NR^{11}OR^{12}$ where $R^{11}$ and $R^{12}$ are hydrogen,
and other groups are as defined below are:

| CPD # | $R^1$ | $R^2$ | $R^1CR^2$ | —$NR^{20}R^{21}$ = heterocycloamino group | M.Pt. ° C. | Mass Spec. |
|---|---|---|---|---|---|---|
| 337 | | | cyclopentyl | 4-phenoxypiperidino | 124.5–125.5 | 384 M + H |
| 338 | | | cyclopentyl | 4-(4-chlorophenyl)piperazino | 135.3 efferves. | 403.12 M + H |
| 339 | | | tetrahydropyran-4-yl | 4-(4-chlorophenyl)piperazino | 192.5–192.7 | 419 M + H |
| 340 | | | cyclopropyl | 4-(5-chloropyridin-2-yl)piperazino | 152.6 efferves. | 376.08 M + H |
| 341 | | | cyclopropyl | 4-(4-chlorophenyl)piperazino | 169.9 efferves. | 375.09 M + H |
| 342 | | | cyclohexyl | 4-(5-chloropyridin-2-yl)piperazino | 116.1 efferves. | 418.13 M + H |
| 343 | | | tetrahydropyran-4-yl | 4-(5-trifluoromethylpyridin-2-yl)-piperazino | 192.5–192.8 | 454 M + H |
| 344 | | | tetrahydropyran-4-yl | 4-(5-chloropyridin-2-yl)piperazino | 186.9 | 420 M + H |
| 345 | | | cyclohexyl | 4-(4-chlorophenyl)piperazino | 146.1–146.6 | 417.1 M + H |
| 346 | | | tetrahydropyran-4-yl | 4-[4-(benzyloxy)phenyl]piperazino | 186 efferves. | 491.1 M + H |
| 347 | | | tetrahydropyran-4-yl | 4-phenoxypiperidino | 128 efferves. | 400.15 M + H |
| 348 | | | cyclohexyl | 4-(5-trifluoromethylpyridin-2-yl)-piperazino | 126.5–148 decomp. | 452.1 M + H |
| 349 | | | piperidin-4-yl | 4-(4-chlorobenzoyl)piperidino.HCl salt | 169.6–170.6 | |
| 350 | | | 1-methylsulfonyl-piperidin-4-yl | 4-(4-chlorobenzoyl)piperidino | | 523 M + H |
| 351 | methyl | methyl | | 4-(4-chlorobenzoyl)piperidino | 185.7–186.7 | |
| 352 | methyl | methyl | | 4-(5-chloropyridin-2-yl)piperazino | 167.2–167.5 | 378.1 M + H |
| 353 | | | tetrahydropyran-4-yl | 4-(5-chloropyridin-2-yloxy)piperidino | | 435.1 M + H |
| 354 | methyl | methyl | | 4-[4-(benzyloxy)phenyl]piperazino | 153.7–155.3 | 449.18 M + H | and are named as follows:
337. N-hydroxy-1-{[(4-phenoxy)piperidine-1-sulfonyl]amino}cyclopentane-1-carboxamide.
339. N-hydroxy-4-{[4-(4-chlorophenyl)piperazine-1-sulfonyl]amino}tetrahydropyran-4-carboxamide.
347. N-hydroxy-4-{[4-(4-phenoxy)piperidine-1-sulfonyl]amino}tetrahydropyran-4-carboxamide.
351. N-hydroxy-2-{[4-(4-chlorobenzoyl)piperidine-1-sulfonyl]amino}-2-methylpropanamide.

IV. Compounds of formula (I) where $R^2$ = hydrogen, $R^{10}$ = —$NR^{11}OR^{12}$ where $R^{11}$ and $R^{12}$ are hydrogen, and other groups are as defined below are:

| CPD # | Stereo chem | $R^1$ | $R^1CNR^3$ | $R^3$ | $R^{20}$ | $R^{21}$ | M.Pt. °C. | Mass Spec. |
|---|---|---|---|---|---|---|---|---|
| 355 | | H | | benzyl | methyl | benzyl | | 363 M+ |
| 356 | 2(RS) | 2-propyl | | benzyl | methyl | 3-phenylpropyl | | 434 M + H |
| 357 | 2(RS) | 2-propyl | | benzyl | methyl | (4-biphenyl)methyl | 136.5–138.5 | 482 M + H |
| 358 | 2(RS) | 2-propyl | | benzyl | methyl | benzyl | 128.2–129 | 406 M + H |
| 359 | 2(RS) | 2-propyl | | benzyl | H | benzyl | | 391 M+ |
| 360 | 2(RS) | 2-propyl | | benzyl | H | methyl | | 316 M + H |
| 361 | 2(RS) | 2-propyl | | benzyl | methyl | 3-(4-biphenyl)propyl | 68–71 | 509 M+ |
| 362 | 2(RS) | 2-propyl | | benzyl | methyl | 2-phenylethyl | | 419 M+ |
| 363 | 2(R) | | piperidino | | methyl | benzyl | | 328 M + H |
| 364 | 2(R) | methyl | | H | H | 3-(5-fluoroindol-1-yl)propyl | 157–158 | | and are named as:
358. N-hydroxy-2-(RS)-{[benzyl-(methyl-benzyl-aminosulfonyl)amino}-3-methylbutyramide.
360. N-hydroxy-2-(RS)-{[benzyl-(methyl-aminosulfonyl)amino}-3-methylbutyramide.
363. N-hydroxy-1-[(methyl-benzyl-aminosulfonyl)amino]piperidine-2-(R)-carboxamide.

V. Compounds of formula (I) where $R^2$ = H, $R^{10}$ = —$NR^{11}OR^{12}$ and other groups are as defined below are:

| CPD # | Stereo-chem | $R^1CNR^3$ | —$NR^{20}R^{21}$ = heterocycloamino group | $R^{11}$ | $R^{12}$ | Mass Spec. |
|---|---|---|---|---|---|---|
| 365 | (RS) | 4-formylpiperazino | 4-(5-fluoroindol-3-yl)piperidino | H | benzyl | 544 M + H |
| 366 | (R) | piperidino | 4-(4,5,6,7-tetrafluoroindol-3-yl)-piperidino | H | benzyl | 569 M + H |
| 367 | (RS) | 4-(methoxycarbonyl)piperazino | 4-(5-fluoroindol-3-yl)piperidino | H | benzyl | 574.21 M + H |
| 368 | (RS) | 4-(tetrahydropyran-4-yl-carbonyl)piperazino | 4-(5-fluoroindol-3-yl)piperidino | H | benzyl | 628.26 M + H |
| 369 | (R) | 4-(tert-butylaminocarbonyl)-piperazino | 4-(4,5,6,7-tetrafluoroindol-3-yl)-piperidino | H | benzyl | 669.24 M + H |
| 370 | (R) | 4-(N,N-dimethylamino-carbonyl)piperazino | 4-(4,5,6,7-tetrafluoroindol-3-yl)-piperidino | H | benzyl | 641.21 M + H |
| 371 | (R) | piperidino | 4-(4,5,6,7-tetrafluoroindol-3-yl)-piperidino | morpholin-4-yl-methyl | H | 578.20 M + H |
| 372 | (R) | piperidino | 4-(5-fluoroindol-3-yl)piperidino | methyl | H | 425 M + H |
| 373 | (R) | 4-(N,N-dimethylamino-carbonyl)piperazino | 4-(5-cyanoindol-3-yl)piperidino | H | benzyl | 594.24 M + H |
| 374 | (R) | piperidino | 4-(5-cyanoindol-3-yl)piperidino | methyl | methyl | 460 M + H | and are named as:
365. N-benzyloxy-4-formyl-1-[4-(5-fluoroindol-3-yl)piperidine-1-sulfonyl]piperazine-2-(RS)-carboxamide.
372. N-hydroxy-N-methyl-1-[4-(5-fluoroindol-3-yl)piperidine-1-sulfonyl]piperidine-2-(R)-carboxamide.

VI. Compounds of formula (I) where $R^2$ = H, $R^{10}$ = —$NR^{11}OR^{12}$ where $R^{11}$ and $R^{12}$ are hydrogen and other groups are as defined below are:

| CPD # | Stereo-chem | $R^1CNR^3$ | —$NR^{20}R^{21}$ = substituted tetrahydropyridine ring | M.Pt. °C. | Mass Spec. |
|---|---|---|---|---|---|
| 375 | (RS) | piperidino | 4-(4-chlorophenyl)-1,2,3,6-tetrahydropyridine | 137.8–138.1 | |
| 376 | (RS) | piperidino | 4-(4-chloro-3-trifluoromethylphenyl)-1,2,3,6-tetrahydropyridine | 136.3–137.4 | |
| 377 | (RS) | piperidino | 4-(4-methoxyphenyl)-1,2,3,6-tetrahydropyridine | 107.6–108.1 | |
| 378 | (RS) | piperidino | 4-(3-chloro-4-fluorophenyl)-1,2,3,6-tetrahydropyridine | 59.8–105.2 | 418 M + H |
| 379 | (RS) | piperidino | 4-(5-chloroindol-3-yl)-1,2,3,6-tetrahydropyridine | 113.2–157.6 | 439 M + H |
| 380 | (RS) | piperidino | 4-(5-fluoroindol-3-yl)-1,2,3,6-tetrahydropyridine | 100–102 | 423 M + H |
| 381 | (RS) | 4-benzyloxycarbonyl-piperazino | 4-(4-fluoro-3-methylphenyl)-1,2,3,6-tetrahydropyridine | 67–70 | 533 M + H |
| 382 | (RS) | 4-acetylpiperazino | 4-(4-fluoro-3-methylphenyl)-1,2,3,6-tetrahydropyridine | 94–98 | 441 M + H |
| 383 | (RS) | 4-(N,N-dimethylamino-carbonyl)piperazino | 4-(4-fluoro-3-methylphenyl)-1,2,3,6-tetrahydropyridine | | 470 M + H |
| 384 | (RS) | 4-tert-butoxycarbonyl-piperazino | 4-(4-fluoro-3-methylphenyl)-1,2,3,6-tetrahydropyridine | 122–126 | 499 M + H |
| 385 | (RS) | piperidino | 4-(4-bromophenyl)-1,2,3,6-tetrahydropyridine | 145.5–147 | 444 M + H |
| 386 | (RS) | piperidino | 4-(4-fluorophenyl)-1,2,3,6-tetrahydropyridine | 159–161 | 384 M + H |
| 387 | (R) | piperidino | 4-(4-fluorophenyl)-1,2,3,6-tetrahydropyridine | 148.2–149 | 384 M + H |
| 388 | (RS) | piperidino | 4-phenyl-1,2,3,6-tetrahydropyridine | 144.5–145 | 366 M + H |

VI. Compounds of formula (I) where $R^2$ = H, $R^{10}$ = —$NR^{11}OR^{12}$ where $R^{11}$ and $R^{12}$ are hydrogen and other groups are as defined below are:

| CPD # | Stereo-chem | $R^1CNR^3$ | —$NR^{20}R^{21}$ = substituted tetrahydropyridine ring | M.Pt. °C. | Mass Spec. |
|---|---|---|---|---|---|
| 389 | (RS) | 4-(N,N-dimethylamino-carbonyl)piperazino | 4-(4-fluorophenyl)-1,2,3,6-tetrahydropyridine | 87.5–91 | 456 M + H |
| 390 | (R) | 4-(N,N-dimethylamino-carbonyl)piperazino | 4-(4-fluorophenyl)-1,2,3,6-tetrahydropyridine | 90.5–95 | 456 M + H |
| 391 | (RS) | piperidino | 4-(4-methylphenyl)-1,2,3,6-tetrahydropyridine | 123.2–125.8 | 380 M + H |
| 392 | (RS) | 4-(N,N-dimethylamino-carbonyl)piperazino | 4-(4-chlorophenyl)-1,2,3,6-tetrahydropyridine | 84–116.8 | 472 M + H |
| 393 | (R) | 2,2-dimethylthio-morpholino | 4-(4-fluorophenyl)-1,2,3,6-tetrahydropyridine | 176.7–177.5 | 430 (M + H) |
| 394 | (RS) | 4-(2,4-difluorophenyl-aminocarbonyl)piperazino | 4-(4-fluorophenyl)-1,2,3,6-tetrahydropyridine |  | 590 M + H |
| 395 | (R) | piperidino | 4-(3,4-difluorophenyl)-1,2,3,6-tetrahydropyridine | 57–61.5 | 402 M + H |
| 396 | (RS) | 4-(N,N-dimethylamino-sulfonyl)piperazino | 4-(4-fluorophenyl)-1,2,3,6-tetrahydropyridine | 120.3–121 | 492 M + H |
| 397 | (RS) | 4-(morpholin-4-yl-carbonyl)piperazino | 4-(4-fluorophenyl)-1,2,3,6-tetrahydropyridine | 102–105 | 498 M + H |
| 398 | (RS) | 4-(2,2,2-trifluoroethyl)-piperazino | 4-(4-fluorophenyl)-1,2,3,6-tetrahydropyridine | 54.3–62.6 | 467 M + H |
| 399 | (RS) | 4-[bis(N,N-dimethylamino-phosphoryl)]piperazino | 4-(4-fluorophenyl)-1,2,3,6-tetrahydropyridine | 98–102 | 519 M + H |
| 400 | (R) | 4-(N,N-dimethylamino-carbonyl)piperazino | 4-(4-fluorophenyl)-1,2,3,6-tetrahydropyridine | 90.4–93.1 | 470 M + H | and are named as:
375. N-hydroxy-1-[4-(4-chlorophenyl)-1,2,3,6-tetrahydropyridine-1-sulfonyl]piperidine-2-(RS)-carboxamide.
381. N-hydroxy-4-benzyloxycarbonyl-1-[4-(4-fluoro-3-methylphenyl)-1,2,3,6-tetrahydropyridine-1-sulfonyl]piperazine-2-(RS)-carboxamide.
393. N-hydroxy-4-[4-(4-fluorophenyl)-1,2,3,6-tetrahydropyridine-1-sulfonyl]-2,2-dimethylthiomorpholine-3-(R)-carboxamide.
399. N-hydroxy-4-[bis(N,N-dimethylaminophosphoryl)]-1-[4-(4-fluorophenyl)-1,2,3,6-tetrahydropyridine-1-sulfonyl]piperazine-2-(RS)-carboxamide.

VII. Compounds of formula (I) where $R^2$ = H, $R^{10}$ = —$NR^{11}OR^{12}$ where $R^{11}$ and $R^{12}$ are hydrogen and other groups are as defined below are:

| CPD # | Stereo-chem | $R^1$ | —$NR^{20}R^{21}$ = substituted tetrahydropyridine ring | M.Pt. °C. | Mass Spec. |
|---|---|---|---|---|---|
| 401 | (R) | methyl | 4-(4-chlorophenyl)-1,2,3,6-tetrahydropyridine | 90.7–93 | 360 M + H |
| 402 | (R) | 2-propyl | 4-(4-chloro-3-methylphenyl)-1,2,3,6-tetrahydropyridine | 65.2–82.2 | 386 M + H |
| 403 | (R) | 4-(benzyloxycarbon-yl)aminobutyl | 4-(4-chlorophenyl)-1,2,3,6-tetrahydropyridine | 72–79 | 551.2 M + H |
| 404 | (R) | phenyl | 4-(4-fluorophenyl)-1,2,3,6-tetrahydropyridine | 79–82.5 | 406 M + H |
| 405 | (R) | 4-(benzyloxycarbon-ylamino)butyl | 4-(4-fluorophenyl)-1,2,3,6-tetrahydropyridine | 61.9–65.6 | 535 M + H |
| 406 | (R) | 2-propyl | 4-(4-fluorophenyl)-1,2,3,6-tetrahydropyridine | 144–144.5 | 372 M + H |
| 407 | (R) | tert-butyl | 4-(4-fluorophenyl)-1,2,3,6-tetrahydropyridine | 110–114.8 | 386 M + H |
| 408 | (R) | 4-fluorophenyl | 4-(4-fluorophenyl)-1,2,3,6-tetrahydropyridine | 89.2–110 | 424 M + H |
| 409 | (R) | 4-fluorophenyl | 4-(4-chlorophenyl)-1,2,3,6-tetrahydropyridine | 76.5–79 | 440 M + H | and are named as:
401. N-hydroxy-2-(R)-1-[4-(4-chlorophenyl)-1,2,3,6-tetrahydropyridine-1-sulfonyl]propionamide.
406. N-hydroxy-2-(R)-1-[4-(4-fluorophenyl)-1,2,3,6-tetrahydropyridine-1-sulfonyl]-3-methylbutyramide.

VIII. Compounds of formula (I) where $R^2$ = H, $R^{10}$ = —OH and other groups are as defined below are:

| CPD # | Stereo-chem | $R^1$ | $R^3$ | $R^1CNR^3$ | —$NR^{20}R^{21}$ | Mass Spec. |
|---|---|---|---|---|---|---|
| 410 | (RS) |  |  | piperidino | 4-(4-fluoro-3-methylphenyl)-1,2,3,6-tetra-hydropyridine | 383 M + H |
| 411 | (RS) |  |  | piperidino | 4-(3-chloro-4-fluorophenyl)-1,2,3,6-tetrahydropyridine | 403 M + H |
| 412 | (R) | 4-(benzyloxycarbo-nylamino)butyl | H |  | 4-(4-chlorophenyl)piperazino | 539 M + H |
| 413 | (R) | 2-propyl | H |  | 4-[4-(pyridin-4-ylmethyloxy)-phenyl]piperazino | 462 M + H |
| 414 | (R) | methyl | H |  | 4-(4-chlorophenyl)piperazino | 347 M+ |

-continued

VIII. Compounds of formula (I) where $R^2$ = H,
$R^{10}$ = —OH and other groups are as defined below are:

| CPD # | Stereo-chem | $R^1$ | $R^3$ | $R^1CNR^3$ | —$NR^{20}R^{21}$ | Mass Spec. |
|---|---|---|---|---|---|---|
| 415 | (R) | methyl | H | | 4-(4-chlorophenyl)piperidino | 346 M + H |
| 416 | (R) | 2-propyl | H | | 4-(5-chloropyridin-2-yloxy)piperidino | 392 M + H |
| 417 | (RS) | | | piperidino | 4-(6-fluorothiazol-3-yl)piperidino | 348 M+ |
| 418 | (R) | | | piperidino | 4-(6-chloroindol-3-yl)piperidino | 426 M + H |
| 419 | | H | H | | 4-(4-fluorophenyl)piperazino | 432 M + H |
| 420 | | H | H | | 4-(4-chlorophenyl)piperazino | 333 M+ |
| 421 | (RS) | | | piperidino | 4-(5-chloroindol-1-yl)piperidino | 426 M + H |
| 422 | (RS) | | | piperidino | 4-(5-chloroindol-3-yl)piperidino | 426 M + H |
| 423 | | H | benzyl | | 4-(4-chlorophenyl)piperazino | 424 M + H |
| 424 | | H | benzyl | | 4-methoxypiperidino | 342 M+ |
| 425 | (RS) | | | piperidino | 4-(5-methylindol-3-yl)piperidino | 406 M + H |
| 426 | (R) | 2-propyl | H | | 4-[4-(pyridin-3-ylmethyloxy)phenyl]-piperazino | 449 M + H |
| 427 | (RS) | | | piperidino | 4-(1,2,3,4-tetrahydro-β-carbolino)piperidino | |
| 428 | (R) | n-propyl | H | | 4-(5-chloropyridin-2-yl)piperazino | 377.1 M + H | and are named as:
410. 1-[4-(4-fluoro-3-methylphenyl)-1,2,3,6-tetrahydropyridine-1-sulfonyl]piperidine-2-(RS)-carboxylic acid.
413. 2-(R)-{[4-(pyridin-4-ylmethyloxyphenyl)piperazine-1-sulfonyl]amino}-3-methylbutyric acid.
427. 1-[4-(1,2,3,4-tetrahydro-β-carbolino)piperidine-1-sulfonyl]piperidine-2-(RS)-carboxylic acid.

IX. Compounds of formula (I) where $R^{10}$ = —OH and other groups are as defined below are:

| CPD # | Stereo-chem | $R^1$ | $R^2$ | $R^3$ | $R^{20}$ | $R^{21}$ | Mass Spec. |
|---|---|---|---|---|---|---|---|
| 429 | (RS) | 2-propyl | H | benzyl | methyl | 4-biphenylmethyl | 466 M+ |
| 430 | (RS) | H | H | benzyl | methyl | benzyl | 348 M+ |
| 431 | (R) | methyl | H | benzyl | H | benzyl | |
| 432 | (RS) | 2-propyl | H | benzyl | methyl | 3-(4-biphenyl)propyl | 494 M+ |
| 433 | (R) | methyl | H | 2-phenylethyl | H | 2-phenylethyl | |
| 434 | (RS) | 2-propyl | H | benzyl | methyl | benzyl | 391 M + H |
| 435 | (RS) | 2-propyl | H | benzyl | methyl | 2-phenylethyl | 405 M + H | and are named as:
429. 2-(RS)-{benzyl-[methyl-(4-biphenylmethyl)aminosulfonyl]amino}-3-methylbutyric acid.
433. 2-(R)-[2-phenylethyl-(2-phenylethylaminosulfonyl)amino]propionic acid.

Miscellaneous compounds

436. A compound of formula (I) where $R^{10}$=—NHOH, $R^1$ and $R^2$=hydrogen, $R^3$ and $R^{20}$ together=—$(CH_2)_2$— and $R^{21}$=4-biphenylmethyl is named as N-hydroxy-5-(biphenyl-4-ylmethyl)-1,1-dioxo-1,2,5-thiadiazolidine-2-acetamide. (361 M+).

436. A compound of formula (I) where $R^{10}$=—NHOH, $R^1$ and $R^2$=hydrogen, $R^3$ and $R^{20}$ together=—$(CH_2)_2$— and $R^{21}$=4-phenoxybenzoyl is named as N-hydroxy-5-(4-phenoxybenzoyl)-1,1-dioxo-1,2,5-thiadiazolidine-2-acetamide. (361 M+).

PREFERRED EMBODIMENTS

While the broadest definition of this invention is set forth in the Summary of the Invention, certain compounds of formula (I) are preferred.
(I) Hydroxamic Acids and their derivatives: Compounds of formula (I) where $R^{10}$ is —$NR^{11}OR^{12}$.
Within this group a preferred group of compounds is that wherein $R^{10}$ is —NHOH.
Within this preferred group, a more preferred group of compounds is that wherein:

$R^1$ is hydrogen, alkyl, cycloalkyl, aryl, aralkyl, or heteroalkyl, more preferably 2-propyl, tert-butyl, 1-hydroxyethyl, tert-butoxymethyl, 2,2-dimethylpropyl, 2-methylpropyl, 1-methylpropyl, n-propyl, benzyl, phenyl, 4-fluorophenyl, cyclohexyl, (1-methyl-1-methylthio)ethyl, phenythiomethyl, benzylthiomethyl, thiophen-2-ylthiomethyl, pyridin-2-ylthiomethyl, 4-(benzyloxycarbonylamino)butyl, or benzyloxymethyl, most preferably 2-propyl, 1-methylpropyl, 2-methylpropyl, 2,2-dimethylpropyl, n-propyl, or 4-fluorophenyl;

$R^2$ is hydrogen; and $R^3$ is hydrogen, alkyl, aralkyl, heteroaralkyl, or heteroalkyl, preferably hydrogen, methyl, N,N-dimethylaminoethyl, pyridin-3-ylmethyl, benzyl, or 2-phenoxyethyl, most preferably hydrogen, N,N-dimethylaminoethyl, or pyridin-3-ylmethyl.

Within this group, particularly preferred compounds are those where the spatial arrangement of the groups at the carbon atom to which $R^1$ and $R^2$ are attached is as shown in FIG. 1 below.

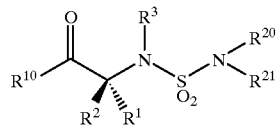

fig. 1

Another more preferred group of compounds is that wherein $R^1$ and $R^2$ together with the carbon atoms to which they are attached form a carbocycle or heterocycle, preferably a carbocycle with a ring size between 3 to 6 carbon atoms, more preferably 5 or 6 carbon atoms, or a heterocycle of 6 ring atoms containing a single N, O, or S atom with the carbon to which $R^1$ and $R^2$ are attached being in the 4-position of the heterocycle, most preferably cyclopentyl, cyclohexyl, or piperidino where the nitrogen in the piperidino ring is optionally substituted with acyl, —$SO_2R$ (where R is alkyl, amino, monosubstituted amino or disubstituted amino), or —CONR'R" (where R' and R" are independently selected from hydrogen, alkyl, cycloalkyl, cycloalkylalkyl, aryl, aralkyl, heteroaryl, and heteroaralkyl); and $R^3$ is as described above.

Yet another more preferred group of compounds is that wherein $R^3$ and $R^1$ together with the atoms to which they are attached form a heterocycloamino group, preferably a heterocycloamino group with a ring size of 6 ring atoms and optionally containing a second heteroatom selected from the group consisting of N, O, or $S(O)_n$ (where n is an integer from 0–2), preferably at the 4-position with the nitrogen atom to which $R^3$ is attached being in the 1-position of the heterocycloamino group. Representative heterocycloamino groups formed by $R^3$ and $R^1$ include, but are not limited to, piperidino, morpholino, thiomorpholino, thiomorpholino-1-oxide, thiomorpholino-1,1,-dioxide, 2,2-dimethylthiomorpholino, or piperazino wherein the nitrogen at the 4-position of the piperazino ring is optionally substituted with alkyl, haloalkyl, cycloalkylalkyl, aralkyl, heteroaralkyl, acyl, —$COOR^a$, -(alkylene)—$COOR^a$ (where $R^a$ is alkyl), —$SO_2R$ (where R is alkyl, amino, monosubstituted amino or disubstituted amino), —CONR'R", or -(alkylene)—CONR'R" (where R' and R" are independently selected from hydrogen, alkyl, cycloalkyl, cycloalkylalkyl, aryl, aralkyl, heteroaryl, and heteroaralkyl), preferably acyl, haloalkyl, —$SO_2R$ (where R is alkyl, amino, monosubstituted amino or disubstituted amino), or —CONR'R" (where R' and R" are independently selected from hydrogen, alkyl, cycloalkyl, cycloalkylalkyl, aryl, aralkyl, heteroaryl, and heteroaralkyl), more preferably acetyl, formyl, 2,2,2-trifluoroethyl, aminocarbonyl, tert-butylaminocarbonyl, N,N-dimethylaminocarbonyl, 2,4-difluorophenylaminocarbonyl, N,N-dimethylaminosulfonyl, bis(N,N-dimethylaminophosphoryl), morpholin-4-ylcarbonyl, morpholin-4-ylsulfonyl or 1,4-pyrazin-2-ylcarbonyl.

Within this group, particularly preferred compounds are those where the spatial arrangement of the groups at the carbon atom to which $R^1$ and $R^2$ are attached has (R) stereochemistry.

Within the above preferred and more preferred groups, an even more preferred group of compounds is where either:
  (i) $R^{20}$ and $R^{21}$ are independently hydrogen, alkyl, acyl, aralkyl, aralkenyl or heteroalkenyl;
  (ii) $R^{20}$ and $R^{21}$ together with the nitrogen atom to which they are attached form a heterocycloamino group, more preferably where $R^{20}$ and $R^{21}$ together with the nitrogen atom to which they are attached form a piperidino or piperazino ring where:
    the piperidino ring is optionally substituted at the 4-position by aryl, heteroaryl, acyl, —CONR'R" (where R' and R" are independently selected from hydrogen, alkyl, cycloalkyl, cycloalkylalkyl, aryl, aralkyl, heteroaryl, and heteroaralkyl), —OR (where R is aryl or heteroaryl), or —$S(O)_nR$ (where n is an integer from 0–2 and R is aryl or heteroaryl), more preferably phenyl, phenoxy, 4-(imidazol-1-yl) phenoxy, 5-chloropyridin-2-yloxy, 4-chlorophenoxy, 4-fluorophenoxy, 4-chlorobenzoyl, 4-cyanobenzoyl, 4-methylbenzoyl, 4-chlorophenylsulfonyl, phenylthio, pyridin-4-ylthio, pyridin-2-ylthio, benzoxazol-2-yl, benzothiazol-2-ylthio, 5-phenylthiazol-2-yl, 5-fluoroindol-3-yl, 6-chloroindol-3-yl, 5-phenylimidazol-2-yl, benzimidazol-2-yl, 4-methylphenylthio, 4-chlorophenylthio, 4-cyanophenyl, 4-fluorophenyl, 4-fluorobenzoyl, 4-fluorophenylaminocarbonyl, 5-chloroindol-3-yl, 5-chlorobenzotriazol-1-yl, 6-methylindol-3-yl, 5-fluoroindol-3-ylcarbonyl, 6-fluoroindol-3-yl, 4,5,6,7-tetrafluoroindol-3-yl, 4-chloroindol-3-yl, 7-methylindol-3-yl, 5-cyanoindol-3-yl, 6-cyanoindol-3-yl, benzothiophen-2-yl, benzothiophen-3-yl, quinolin-3-yl, 5-chlorobenzimidazol-1-yl, pyridin-2yloxy, 6-chloropyridin-2-yloxy, naphth-1-yl, naphth-2-yl, 1,2,3,4-tetrahydro-β-carboline, 7-chloro-1,3-dihydro-2H-1,4-benzodiazepin-2-one-5-yl, 8-chloro-1,3-dihydro-2H-1,4-benzodiazepin-2-one-5-yl, 7-fluoro-1,3-dihydro-2H-1,4-benzodiazepin-2-one-5-yl or 8-fluoro-1,3-dihydro-2H-1,4-benzodiazepin-2-one-5-yl, most preferably 4-chlorophenoxy, 4-fluorophenoxy, 4-fluorophenyl, 5-chloropyridin-2-yloxy, 6-chloropyridin-2-yloxy, pyridin-2-yloxy, phenoxy, phenylthio, pyridin-4-ylthio, 4-chlorobenzoyl, 5-fluoroindol-3-yl, 4,5,6,7-tetrafluoroindol-3-yl, 6-methylindol-3-yl, 5-chloroindol-3-yl, 5-cyanoindol-3-yl, 5-chlorobenzotriazol-1-yl, 1,2,3,4-tetrahydro-β-carboline, or 6-chloroindol-3-yl; and
    the piperazino ring is optionally substituted at the 4-position by aryl, heteroaryl, —CONR'R" (where R' and R" are independently selected from hydrogen, alkyl, cycloalkyl, cycloalkylalkyl, aryl, aralkyl, heteroaryl, and heteroaralkyl), or —$SO_2$aryl, more preferably 4-chlorophenyl, 5-chloropyridin-2-yl, 4-benzyloxyphenyl, 4-(pyridin-4-yl) methyloxyphenyl, 2-phenylbenzoxazol-5-yl, pyridin-4-yl, 5-trifluoromethyl-pyridin-2-yl, 4-cyanophenyl, 5-nitropyridin-2-yl, 5-bromopyridin-2-yl, 4-biphenylaminocarbonyl, 4-phenoxyphenyl-aminocarbonyl, 4-benzyloxyphenylaminocarbonyl, or 4-chlorophenylaminocarbonyl, most preferably 4-chlorophenyl, 4-benzyloxyphenyl, 5-chloropyridin-2-yl, 4-cyanophenyl, 4-chlorophenylaminocarbonyl, or 2-phenylbenzoxazol-5-yl; or
  (iii) $R^{20}$ and $R^{21}$ together with the nitrogen atom to which they are attached form 1,2,3,6-tetrahydropyridine ring which is substituted at the 4-position by an aryl or heteroaryl ring, preferably phenyl, 4-chlorophenyl, 4-bromophenyl, 4-fluorophenyl, 4-methylphenyl, 4-fluoro-3-methylphenyl, 4-chloro-3-trifluoromethylphenyl, 4-methoxyphenyl, 3-chloro-4-fluorophenyl, 5-chloroindol-3-yl, 5-fluoroindol-3-yl or 3,4-difluorophenyl, most preferably 4-chlorophenyl, 4-fluorophenyl, 4-fluoro-3-methylphenyl, or 3-chloro-4-fluorophenyl.

(II) Carboxylic Acids: Compounds of formula (I) where $R^{10}$ is —OH.

Within this group of compounds a preferred group is that wherein:
  $R^1$ is hydrogen, alkyl, aryl, aralkyl, or heteroalkyl, preferably alkyl, aryl, or heteroalkyl, more preferably hydrogen, 2-propyl, tert-butyl, 1-hydroxyethyl, tert-butoxymethyl, 2,2-dimethylpropyl, 2-methylpropyl, 1-methylpropyl, propyl, benzyl, phenyl, 4-fluorophenyl, cyclohexyl, (1-methyl-1-methylthio)ethyl, phenythiomethyl, benzylthiomethyl, thiophen-2-ylthiomethyl, pyridin-2-ylthiomethyl, 4-(benzyloxycarbonylamino)butyl, or benzyloxymethyl, most preferably hydrogen, methyl, or 2-propyl;

$R^2$ is hydrogen; and $R^3$ is hydrogen, alkyl, aralkyl, heteroaralkyl, or heteroalkyl, preferably hydrogen, benzyl, N,N-dimethylaminoethyl, or pyridin-3-ylmethyl, most preferably hydrogen, benzyl or pyridin-3-ylmethyl, provided that $R^1$, $R^2$ and $R^3$ are not all hydrogen.

Within this group, particularly preferred compounds are those where the spatial arrangement of the groups at the carbon atom to which $R^1$ and $R^2$ are attached is as shown in FIG. 1 below.

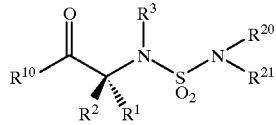

fig. 1

Another preferred group of compounds is that wherein $R^1$ and $R^2$ together with the carbon atoms to which they are attached form a carbocycle or heterocycle, preferably a carbocycle with a ring size between 3 to 6 carbon atoms, more preferably 5 or 6 carbon atoms, or a heterocycle of 6 ring atoms containing a single N, O, or S atom with the carbon to which $R^1$ and $R^2$ are attached being in the 4-position of the heterocycle, most preferably cyclopentyl, cyclohexyl, or piperidino ring where the nitrogen in the piperidino ring is optionally substituted with acyl, —$SO_2R$ (where R is alkyl, amino, monosubstituted amino or disubstituted amino), or —CONR'R" (where R' and R" are independently selected from hydrogen, alkyl, cycloalkyl, cycloalkylalkyl, aryl, aralkyl, heteroaryl, and heteroaralkyl); and $R^3$ is as described above.

Yet another preferred group of compounds is that wherein $R^3$ and $R^1$ together with the atoms to which they are attached form a heterocycloamino group, preferably a heterocycloamino group with a ring size of 6 ring atoms and optionally containing a second heteroatom selected from the group consisting of N, O, or $S(O)_n$ (where n is an integer from 0–2), preferably at the 4-position with the nitrogen atom to which $R^3$ is attached being in the 1-position of the heterocycloamino group. Representative heterocycloamino groups formed by $R^3$ and $R^1$ include, but are not limited to, piperidino, morpholino, thiomorpholino, thiomorpholino-1-oxide, thiomorpholino-1,1-dioxide, 2,2-dimethylthiomorpholino, or piperazino wherein the nitrogen at the 4-position of the piperazino ring is optionally substituted with alkyl, haloalkyl, cycloalkylalkyl, acyl, -(alkylene)—$COOR^a$ (where $R^a$ is alkyl), —$SO_2R$ (where R is alkyl, amino, monosubstituted amino or disubstituted amino), —CONR'R", or -(alkylene)—CONR'R" (where R' and R" are independently selected from hydrogen, alkyl, cycloalkyl, cycloalkylalkyl, aryl, aralkyl, heteroaryl, and heteroaralkyl), preferably acyl, haloalkyl, —$SO_2R$ (where R is alkyl, amino, monosubstituted amino or disubstituted amino), or —CONR'R" (where R' and R" are independently selected from hydrogen, alkyl, cycloalkyl, cycloalkylalkyl, aryl, aralkyl, heteroaryl, and heteroaralkyl), more preferably acetyl, formyl, 2,2,2-trifluoroethyl, aminocarbonyl, N,N-dimethylaminocarbonyl, 2,4-difluorophenylaminocarbonyl, N,N-dimethylaminosulfonyl, bis(N,N-dimethylaminophosphoryl), morpholin-4-ylcarbonyl, morpholin-4-ylsulfonyl, or 1,4-pyrazin-2-ylcarbonyl.

Within this group, particularly preferred compounds are those where the spatial arrangement of the groups at the carbon atom to which $R^1$ and $R^2$ are attached has (R) stereochemistry.

Within the above preferred groups, a more preferred group of compounds is where either:

(i) $R^{20}$ is hydrogen or alkyl, preferably hydrogen or methyl; most preferably methyl; and $R^{21}$ is aryl, aralkyl, or heteroaralkyl, preferably benzyl, 4-biphenylmethyl, 3-(4-biphenyl)propyl or 2-phenylethyl, most preferably benzyl or 4-biphenylmethyl;

(ii) $R^{20}$ and $R^{21}$ together with the nitrogen atom to which they are attached form a heterocycloamino group substituted with an aryl or heteroaryl ring, more preferably where $R^{20}$ and $R^{21}$ together with the nitrogen atom to which they are attached form a piperidino or piperazino ring substituted at the 4-position by aryl or heteroaryl, most preferably where:

the piperidino ring is substituted by 4-chlorophenyl, 4-bromophenyl, 4-fluorophenyl, 4-methylphenyl, 4-fluoro-3-methylphenyl, 4-chloro-3-trifluoromethylphenyl, 4-methoxyphenyl, 3-chloro-4-fluorophenyl, 3,4-difluorophenyl, 4-(pyridin-4-ylmethyloxy)phenyl, 4-(pyridin-3-ylmethyloxy)phenyl 5-chloropyridin-2-yl, 5-chloropyridin-2-yloxy, 6-fluorobenzisothiazol-3-yl, 6-chloroindol-3-yl, 5-chloroindol-1-yl, 5-fluoroindol-3-yl, 4,5,6,7-tetrafluoroindol-3-yl, or 6-fluoroindol-3-yl, most preferably 4-chlorophenyl, 4-fluorophenyl, 5-chloropyridin-2-yloxy, 6-fluorobenzisothiazol-3-yl, 4-(pyridin-4-ylmethyloxy)phenyl, or 6-fluorobenzisothiazol-3-yl; and the piperazino is substituted by 4-chlorophenyl, 4-bromophenyl, 4-fluorophenyl, 4-methylphenyl, 4-fluoro-3-methylphenyl, 4-chloro-3-trifluoromethylphenyl, 4-methoxyphenyl, 3-chloro-4-fluorophenyl, 3,4-difluorophenyl, 4-(pyridin-4-ylmethyloxy)phenyl, 4-(pyridin-3-ylmethyloxy)phenyl 5-chloropyridin-2-yl, 6-fluorobenzisothiazol-3-yl, 6-chloroindol-3-yl, 5-chloroindol-1-yl, 5-fluoroindol-3-yl, 4,5,6,7-tetrafluoroindol-3-yl, or 6-fluoroindol-3-yl, most preferably 4-chlorophenyl, 4-fluorophenyl, 6-fluorobenzisothiazol-3-yl, 4-(pyridin-4-yl-methyloxy)phenyl, or 6-fluorobenzisothiazol-3-yl;

(iii) $R^{20}$ and $R^{21}$ together with the nitrogen atom to which they are attached form a 1,2,3,6-tetrahydropyridine ring which is substituted at the 4-position by aryl or heteroaryl, more preferably 4-chloirophenyl, 4-bromophenyl, 4-fluorophenyl, 4-methylphenyl, 4-fluoro-3-methylphenyl, 4-chloro-3-trifluoromethylphenyl, 4-methoxyphenyl, 3-chloro-4-fluorophenyl, 3,4-difluorophenyl, 4-(pyridin-4-ylmethyloxy)phenyl, 4-(pyridin-3-ylmethyloxy)phenyl, 5-chloropyridin-2-yl, 6-fluorobenzisothiazol-3-yl, 6-chloroindol-3-yl, 5-chloroindol-1-yl, or 6-fluoroindol-3-yl, most preferably 4-chlorophenyl, 4-fluorophenyl, or 4-fluoro-3-methylphenyl; or (iv) $R^{20}$ and $R^{21}$ together with the nitrogen atom to which they are attached form a heterocycloamino group that is fused to a cycloalkyl, aryl or heteroaryl ring.

Exemplary particularly preferred compounds are:

N-hydroxy-2-(R)-{[4-(4-chlorophenoxy)piperidine-1-sulfonyl]amino}-3-methylbutyramide.

N-hydroxy-2-(R)-{[4-(5-chloropyridin-2-yloxy)piperidine-1-sulfonyl]amino}-3-methylbutyramide.

N-hydroxy-2-(R)-{[4-(4-fluorophenoxy)piperidine-1-sulfonyl]amino}-3-methylbutyramide.

N-hydroxy-2-(R)-{[4-(4-chlorophenyl)piperazine-1-sulfonyl]amino}-3-methylbutyramide.

N-hydroxy-2-(R)-{[4-(4-benzyloxyphenyl)piperazine-1-sulfonyl]amino}-3-methylbutyramide.

N-hydroxy-2-(R)-{[4-(5-chloropyridin-2-yl)piperazine-1-sulfonyl]amino}-3-methylbutyramide.

N-hydroxy-2-(R)-{[4-(2-phenylbenzoxazol-5-yl)piperazine-1-sulfonyl]amino}-3-methylbutyramide.

N-hydroxy-1-[4-(phenoxy)piperidine-1-sulfonyl]piperidine-2-(RS)-carboxamide.

N-hydroxy-1-[4-(phenylthio)piperidine-1-sulfonyl]piperidine-2-(RS)-carboxamide.

N-hydroxy-1-[4-(pyridin-4-ylthio)piperidine-1-sulfonyl]piperidine-2-(R)-carboxamide.

N-hydroxy-1-[4-(4-chlorophenyl)piperazine-1-sulfonyl]piperidine-2-(RS)-carboxamide.

N-hydroxy-1-[4-(4-chlorobenzoyl)piperidine-1-sulfonyl]piperidine-2-(R)-carboxamide.

N-hydroxy-1-[4-(6-chloroindol-3-yl)piperidine-1-sulfonyl]piperidine-2-(RS)-carboxamide.

N-hydroxy-1-[4-(5-fluoroindol-3-yl)piperidine-1-sulfonyl]piperidine-2-(RS)-carboxamide.

N-hydroxy-4-acetyl-1-[4-(4-chlorobenzoyl)piperidine-1-sulfonyl]piperazine-2-(RS)-carboxamide.

N-hydroxy-2-(R)-3-(R)-{[4-(5-chloropyridin-2-yloxy)piperidine-1-sulfonyl]amino}-3-methylvaleramide.

N-hydroxy-2-(R)-{[4-(5-chloropyridin-2-yloxy)piperidine-1-sulfonyl]amino}-4-methylvaleramide.

N-hydroxy-2-(R)-3-(S)-{[4-(6-chloropyridin-2-yloxy)piperidine-1-sulfonyl]amino}-3-methylvaleramide.

N-hydroxy-2-(R)-{[4-(6-chloropyridin-2-yloxy)piperidine-1-sulfonyl]amino}-4,4-dimethylvaleramide.

N-hydroxy-1-[4-(5-chloropyridin-2-yloxy)piperidine-1-sulfonyl]piperidine-2-(RS)-carboxamide.

N-hydroxy-1-[4-(5-chloroindol-3-yl)piperidine-1-sulfonyl]piperidine-2-(RS)-carboxamide.

N-hydroxy-1-[4-(5-chlorobenzotriazol-1-yl)piperidine-1-sulfonyl]piperidine-2-(RS)-carboxamide.

N-hydroxy-4-acetyl-1-[4-(6-methylindol-3-yl)piperidine-1-sulfonyl]piperazine-2-(RS)-carboxamide.

N-hydroxy-1-[4-(4-chlorobenzoyl)piperidine-1-sulfonyl]-4-formylpiperazine-2-(RS)-carboxamide.

N-hydroxy-2-(R)-{[4-(5-chloropyridin-2-yl)piperazine-1-sulfonyl]amino}valeramide.

N-hydroxy-2-(R)-{[4-(5-chloropyridin-2-yl)piperazine-1-sulfonyl]amino}-4-methylvaleramide.

N-hydroxy-2-(R)-{[4-(4-cyanophenyl)piperazine-1-sulfonyl]amino}-3-methylbutyramide.

N-hydroxy-2-(R)-{[4-(4-chlorophenylaminocarbonyl)piperazine-1-sulfonyl]amino}-3methylbutyramide.

N-hydroxy-2-(R)-{[4-(4-chlorophenyl)piperazine-1-sulfonyl]amino}valeramide.

N-hydroxy-1-[4-(5-chloropyridin-2-yl)piperazine-1-sulfonyl]piperidine-2-(RS)-carboxamide.

N-hydroxy-1-[4-(4-chlorobenzoyl)piperidine-1-sulfonyl]-4-(N,N-dimethylaminocarbonyl)piperazine-2-(R)-carboxamide.

N-hydroxy-4-(N,N-dimethylaminocarbonyl)-1-[4-(4,5,6,7-tetrafluoroindol-3-yl)piperidine-1-sulfonyl]piperazine-2-(R)-carboxamide.

N-hydroxy-4-(N,N-dimethylaminosulfonyl)-1-[4-(4,5,6,7-tetrafluoroindol-3-yl)piperidine-1-sulfonyl]piperazine-2-(R)-carboxamide.

N-hydroxy-1-[4-(4-chlorobenzoyl)piperidine-1-sulfonyl]-4-(N,N-dimethylaminosulfonyl)piperazine-2-(R)-carboxamide.

N-hydroxy-1-[4-(4-chlorobenzoyl)piperidine-1-sulfonyl]-4-(1,4-pyrazin-2-ylcarbonyl)piperazine-2-(R)-carboxamide.

N-hydroxy-1-[4-(5-cyanoindol-3-yl)piperidine-1-sulfonyl]-4-(morpholin-4-yl-carbonyl)piperazine-2-(R)-carboxamide.

N-hydroxy-1-[4-(5-cyanoindol-3-yl)piperidine-1-sulfonyl]piperidine-2-(R)-carboxamide.

N-hydroxy-1-[4-(4,5,6,7-tetrafluoroindol-3-yl)piperidine-1-sulfonyl]piperidine-2-(R)-carboxamide.

N-hydroxy-2-(R)-(4-fluorophenyl)-2-{[4-(4-fluorophenyl)-1,2,3,6-tetrahydropyridine-1-sulfonyl]amino}acetaide.

N-hydroxy-1-[4-(4-fluorophenyl)-1,2,3,6-tetrahydropyridine-1-sulfonyl]piperidine-2-(R)-carboxamide.

N-hydroxy-1-[4-(4-fluorophenyl)piperidine-1-sulfonyl]piperidine-2-(R)-carboxamide.

N-hydroxy-1-[4-(4-fluorophenyl)-1,2,3,6-tetrahydropyridine-1-sulfonyl]-4-(2,2,2-trifluoroethyl)piperizine-2-(R)-carboxamide.

N-hydroxy-1-[4-(4-fluorophenyl)piperidine-1-sulfonyl]-4-(2,2,2-trifluoroethyl)piperazine-2-(R)-carboxamide.

N-hydroxy-1-[4-(4-fluorophenyl)piperidine-1-sulfonyl]-4-(morpholin-4-ylcarbonyl)piperazine-2-(R)-carboxamide.

N-hydroxy-1-[4-(4-fluorophenyl)piperidine-1-sulfonyl]-4-(morpholin-4-ylsulfonyl)piperazine-2-(R)-carboxamide.

N-hydroxy-1-[4-(4-fluorophenyl)-1,2,3,6-tetrahydropyridine-1-sulfonyl]-4-(morpholin-4-ylsulfonyl)piperazine-2-(R)-carboxamide.

N-hydroxy-4-(N,N-dimethylaminosulfonyl)-1-[4-(4-fluorophenyl)piperidine-1-sulfonyl]piperazine-2-(R)-carboxamide.

N-hydroxy-4-(N,N-dimethylaminosulfonyl)-1-[4-(4-fluorophenyl)-1,2,3,6-tetrahydropyridine-1-sulfonyl]-piperazine-2-(R)-carboxamide.

N-hydroxy-4-[bis(N,N-dimethylaminophosphoryl)]-1-[4-(4-fluorophenyl)-1,2,3,6-tetrahydropyridine-1-sulfonyl]piperazine-2-(R)-carboxamide.

N-hydroxy-4-[bis(N,N-dimethylaminophosphoryl)]-1-[4-(4-fluorophenyl)-piperidine-1-sulfonyl]piperazine-2-(R)-carboxamide.

N-hydroxy-4-(N,N-dimethylaminocarbonyl)-1-[4-(4-fluorophenyl)-1,2,3,6-tetrahydropyridine-1-sulfonyl]piperazine-2-(R)-carboxamide.

N-hydroxy-4-(2,4-difluorophenylaminocarbonyl)-1-[4-(4-fluorophenyl)-1,2,3,6-tetrahydropiperidine-1-sulfonyl]piperazine-2-(R)-carboxamide.

N-hydroxy-4-(N,N-dimethylaminocarbonyl)-1-[4-(4-fluorophenyl)piperidine-1-sulfonyl]piperazine-2-(R)-carboxamide.

N-hydroxy-4-(N,N-dimethylaminocarbonyl)-1-[4-(4-fluorophenyl)-3-oxo-piperazine-1-sulfonyl]piperazine-2-(R)-carboxamide.

N-hydroxy-4-(N,N-dimethylaminocarbonyl)-1-[4-(4-fluorophenyl)-3-oxo-piperidine-1-sulfonyl]piperazine-2-(R)-carboxamide.

N-hydroxy-4-(N,N-dimethylaminocarbonyl)-1-[4-(4-fluorophenyl)-5-hydroxy-1,2,3,6-tetrahydropiperidin-1-sulfonyl]piperazine-2-(R)-carboxamide.

N-hydroxy-2-(R)-{[4-(4-fluorophenyl)-1,2,3,6-tetrahydropyridine-1-sulfonyl]amino}-3-methylbutyramide.

N-hydroxy-2-(R)-{[4-(4-fluorophenyl)-1,2,3,6-tetrahydropyridine-1-sulfonyl]amino}3,3-dimethylbutyramide.

N-hydroxy-1-[1,2,3,4-tetrahydro-beta-carboline-2-sulfonyl]piperidine-2-(R)-carboxamide.

N-hydroxy-4-(N,N-dimethylaminocarbonyl)-1-[7-fluoro-1,2,3,4-tetrahydro-beta-carboline-2-sulfonyl]piperazine-2-(R)-carboxamide N-hydroxy-4-aminocarbonyl-1-[4-(4-chlorobenzoyl)piperidine-1-sulfonyl]piperazine-2-(R)-carboxamide.

N-hydroxy-1-[4-(5-fluoroindol-3-yl)piperidine-1-sulfonyl]-4-formylpiperazine-2-(R)-carboxamide.

N-hydroxy-4-acetyl-1-[4-(5-fluoroindol-3-yl)piperidine-1-sulfonyl]piperazine-2-(R)-carboxamide.

N-hydroxy-4-(N,N-dimethylaminocarbonyl)-1-[4-(5-fluoroindol-3-yl)piperidine-1-sulfonyl]piperazine-2-(R)-carboxamide.

N-hydroxy-4-tert-butylaminocarbonyl-1-[4-(5-fluoroindol-3-yl)piperidine-1-sulfonyl]piperazine-2-(R)-carboxamide.

N-hydroxy-1-[4-(4-fluoro-3-methylphenyl)-1,2,3,6-tetrahydropyridine-1-sulfonyl]piperidine-2-(R)-carboxamide.

N-hydroxy-1-[4-(4-chlorophenyl)-1,2,3,6-tetrahydropyridine-1-sulfonyl]-4-(N,N-dimethylaminocarbonyl)piperazine-2-(R)-carboxamide.

N-hydroxy-N-methyl-4-(N,N-dimethylaminocarbonyl)-1-[4-(4-fluorophenyl)-1,2,3,6-tetrahydropyridine-1-sulfonyl]piperazine-2-(R)-carboxamide.

N-hydroxy-1-[4-(5-cyanoindol-3-yl)piperidine-1-sulfonyl]-4-(2,2,2-trifluoroethyl)-piperazine-2-(R)-carboxamide.

N-hydroxy-1-[4-(4-fluorophenyl)-1,2,3,6-tetrahydropyridine-1-sulfonyl]-4-(morpholin-4-ylcarbonyl)piperazine-2-(R)-carboxamide.

N-hydroxy-1-[4-(4-fluorophenyl)-1,2,3,6-tetrahydropyridine-1-sulfonyl]-4-(tert-butoxycarbonyl)piperazine-2-(R)-carboxamide.

N-hydroxy-2-(R)-{[4-(4-fluorophenyl)-1,2,3,6-tetrahydropyridine-1-sulfonyl]amino}-2-cyclohexylacetamide.

N-hydroxy-2-(R)-{(pyridin-3-ylmethyl)-[4-(4-fluorophenyl)-1,2,3,6-tetrahydropyridine-1-sulfonyl]amino}-2-(4-fluorophenyl)acetamide.

N-hydroxy-2-(R)-{[4-(4-fluorophenyl)-1,2,3,6-tetrahydropyridine-1-sulfonyl]amino}-3-(S)-hydroxybutyramide.

N-hydroxy-1-[4-(4-fluorophenyl)-1,2,3,6-tetrahydropyridine-1-sulfonyl]-4-(S)-hydroxypiperidine-2-(R)-carboxamide.

N-hydroxy-2-(R)-{[4-(4-fluorophenyl)-1,2,3,6-tetrahydropyridine-1-sulfonyl]amino}-2(4-hydroxyphenyl)acetamide.

N-hydroxy-2-(R)-{[4-(4-fluorophenyl)piperidine-1-sulfonyl]amino}-2-(4-hydroxyphenyl)acetamide.

N-hydroxy-2-(R)-{[4-(4-fluorophenyl)-1,2,3,6-tetrahydropyridine-1-sulfonyl]amino}-4-methylvaleramide.

N-hydroxy-2-(R)-{[4-(4-fluorophenyl)-1,2,3,6-tetrahydropyridine-1-sulfonyl]amino}-3-phenylpropionamide.

N-hydroxy-2-(R)-{[4-(4-fluorophenyl)-1,2,3,6-tetrahydropyridine-1-sulfonyl]amino}-3-(4-hydroxyphenyl)propionamide.

N-hydroxy-2-(R)-{[4-(4-fluorophenyl)-1,2,3,6-tetrahydropyridine-1-sulfonyl]amino}-3-(S)-methylvaleramide.

N-hydroxy-1-[4-(4-fluorophenyl)-1,2,3,6-tetrahydropyridine-1-sulfonyl]-4-(N-methylaminocarbonyl)piperazine-2-(R)-carboxamide.

N-hydroxy-2-(R)-{[4-(4-fluorophenyl)-1,2,3,6-tetrahydropyridine-1-sulfonyl]amino}-valeramide.

N-hydroxy-2-(R)-{[4-(4-fluorophenyl)-1,2,3,6-tetrahydropyridine-1-sulfonyl]amino}-4-pentenamide.

N-hydroxy-2-(R)-{[4-(4-fluorophenyl)-1,2,3,6-tetrahydropyridine-1-sulfonyl]amino}-3-(thien-2-yl-propionamide.

N-hydroxy-2-(R)-{[4-(4-fluorophenyl)-1,2,3,6-tetrahydropyridine-1-sulfonyl]amino}-4-methylthiobutyramide.

N-hydroxy-2-(R)-{[4-(4-fluorophenyl)-1,2,3,6-tetrahydropyridine-1-sulfonyl]amino}-3-tert-butoxypropionamide.

N-hydroxy-2-(R)-{[4-(4-fluorophenyl)-1,2,3,6-tetrahydropyridine-1-sulfonyl]amino}-3-benzyloxypropionamide.

N-hydroxy-2-(R)-{[4-(4-fluorophenyl)-1,2,3,6-tetrahydropyridine-1-sulfonyl]amino}-3-(R)-methylvaleramide.

2-[benzyl-(benzylmethylaminosulfonyl)amino]acetic acid.

2-(R)-{benzyl-[(4-biphenylmethyl)methylamninosulfonyl)]amino}-3-methylbutyric acid.

2-(R)-{[4-(4-chlorophenyl)piperidine-1-sulfonyl]amino}propionic acid.

2-(R)-{[4-(5-chloropyridin-2-yloxy)piperidine-1-sulfonyl]amino}-3-methylbutyric acid.

1-[4-(6-fluorobenzisothiazol-3-yl)piperidine-1-sulfonyl]piperidine-2-(R)-carboxylic acid.

1-[4-(6-chloroindol-3-yl)piperidine-1-sulfonyl]piperidine-2-(R)-carboxylic acid.

1-[4-(4-chlorophenyl)piperidine-1-sulfonyl]-4-(N,N-dimethylaminocarbonyl)-piperazine-2-(R)-carboxylic acid.

4-(N,N-dimnethylaminocarbonyl)-1-[4-(4-fluorophenyl)piperidine-1-sulfonyl]-piperazine-2-(R)-carboxylic acid.

2-(R)-{[4-(4-chlorophenyl)piperazino-1-sulfonyl]amino}propionic acid.

2-(R)-{[4-(4-fluorophenyl)piperazino-1-sulfonyl]amino}acetic acid.

2-(R)-{[4-(4-chlorophenyl)piperazino-1-sulfonyl]amino}acetic acid.

2-(R)-{[4-(pyridin-4-ylmethyloxyphenyl)piperazino-1-sulfonyl]amino}-3-methylbutyric acid.

6-benzyloxycarbonylamino-2-(R)-{[4-(5-chlorophenyl)piperazino-1-sulfonyl]amino}-hexanoic acid.

2-(R)-{[4-(4-fluorophenyl)-1,2,3,6-tetrahydropyridine-1-sulfonyl]amino}-3-methyl-butyric acid.

1-[4-(4-fluoro-3-methylphenyl)-1,2,3,6-tetrahydropyridine-1-sulfonyl]piperidine-2-(R)-carboxylic acid.

1-[4-(3-chloro-4-fluorophenyl)-1,2,3,6-tetrahydropyridine-1-sulfonyl]piperidine-2-(R)-carboxylic acid.

1-[4-(4-fluorophenyl)-1,2,3,6-tetrahydropyridine-1-sulfonyl]-4-(N,N-dimethylaminocarbonyl)piperazine-2-(R)-carboxylic acid.

1-[4-(4-chlorophenyl)-1,2,3,6-tetrahydropyridine-1-sulfonyl]-4-(N,N-dimethylaminosulfonyl)piperazine-2-(R)-carboxylic acid.

N-hydroxy-1-[6-fluoro-1,2,3,4-tetrahydro-beta-carboline-2-sulfonyl]piperidine-2-(R)-carboxylic acid.

N-hydroxy-2-(R)-{[1,2,3,4-tetrahydro-beta-carboline-2-sulfonyl]amino}propionic acid.

N-hydroxy-2-(R)-{(pyridin-2-ylmethyl)-[1,2,3,4-tetrahydro-beta-carboline-2-sulfonyl]amino}propionic acid.

N-hydroxy-2-(R)-{[4-(4-fluorophenyl)-1,2,3,6-tetrahydropyridine-1-sulfonyl]amino}-4-methylvaleric acid.

GENERAL SYNTHETIC SCHEME

Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as *Fieser and Fieser's Reagents for Organic Synthesis*, Volumes 1–15 (John Wiley and Sons, 1991); *Rodd's Chemistry of Carbon Compounds*, Volumes 1–5 and Supplementals (Elsevier Science Publishers, 1989), *Organic Reactions*, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

In general, compounds of formula (I) can be prepared from alkyl 2-[(aminosulfonyl)amino]acetates of formula Ia.

Preparation of Compounds of Formula Ia

Schemes A, B, and C describe alternative methods to generate the compounds of formula Ia.

A compound of formula Ia where $R^3$ can optionally be hydrogen is prepared from an alpha-amino acetate 1 as shown in Scheme A.

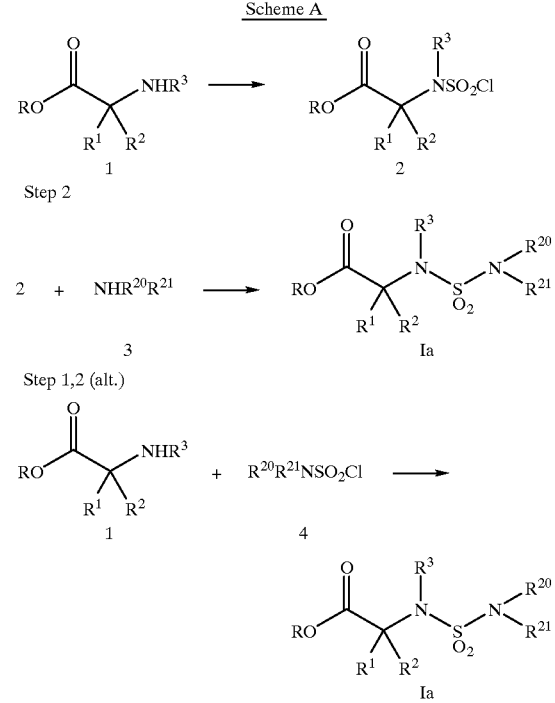

In Step 1, a 2-[(chlorosulfonyl)amino]acetate of formula 2 is prepared, either:

(a) by reacting an alpha-amino acetate 1 (where R is alkyl, preferably methyl, ethyl, or tert-butyl and $R^3$ is as defined in the Summary of the Invention) with sulfuryl chloride in an aprotic organic solvent (e.g., dichloromethane, tetrahydrofuran, dioxane, acetonitrile, and the like). The reaction may be carried out with or without the presence of an organic base (e.g., triethylamine or pyridine). If an organic base is used, the reaction is carried out at temperatures ranging from −78° C. to 25° C., otherwise it is carried out between 25° C. to 80° C.; or (b) by reacting chlorosulfonic acid with an excess amount of compound 1, or with an equimolar amount of compound 1 in the presence of a non-nucleophilic organic base to give a sulfamic acid intermediate. The reaction is carried out in chlorinated hydrocarbons (e.g., dichloromethane, chloroform, and the like) at 0° C. to 30° C. The sulfamic acid intermediate is then converted to a 2-[(chlorosulfonyl)amino]acetate of formula 2 by reacting it with a suitable chlorinating agent (e.g., phosphorus pentachloride, thionyl chloride, phosphorus oxychloride, preferably phosphorus pentachloride, and the like). The reaction proceeds upon heating at temperatures ranging from 70° C. to 110° C. Suitable solvents for the reaction are aromatic hydrocarbons such as benzene, toluene, and the like.

In general, compounds of formula 1 are commercially available or they can be prepared by methods well known in the field of organic chemistry. For example, esters of natural and unnatural amino acids such as alanine, valine, pipecolinic acid, etc., are readily available from Aldrich.

Compounds of formula 1 where $R^1$ and $R^3$ together form a morpholino ring can be prepared by following the procedures described in Brown, G. R., Foubister, A. J., Wright, B., *J. Chem. Soc. Perk. Trans. I*, 2577, (1985) and Kogami, Y., Okawa, K. *Bull. Chem. Soc. Jpn.*, 60, 2963, (1987). Alpha-thiomethyl amino acids can be prepared by following the procedures described in Arnold, L. D., Kalantar, T. H., Vederas, J. C. *J. Am. Chem. Soc.*, 107, 7108, (1985).

Compounds of formula 1 where $R^3$ is not hydrogen can be prepared under reductive amination reaction conditions by reacting a corresponding alpha-amino acetate 1 where $R^3$ is hydrogen with an aldehyde or ketone in the presence of a suitable reducing agent (e.g., sodium cyanoborohydride, sodium triacetoxyborohydride, and the like) and an organic acid (e.g., glacial acetic acid, trifluoroacetic acid, and the like) at ambient temperature. Suitable solvents for the reaction are halogenated hydrocarbons (e.g., 1,2-dichloroethane, chloroform, and the like).

In Step 2, a compound of formula Ia is prepared by reacting a compound of formula 2 either with an excess amount of an amine of formula 3 or with an equimolar amount of the amine 3 in the presence of a non-nucleophilic organic base (e.g., triethylamine or pyridine, preferably pyridine). The reaction is carried out at temperatures ranging from −78° C. to 30° C., preferably at 0° C. Suitable solvents for the reaction are dichloromethane, diethyl ether, tetrahydrofuran, and the like. Alternatively, a compound of formula Ia is prepared by reacting a compound of formula 2 with an excess of an amine of formula 3 or its corresponding ammonium salt in the presence of an excess of a water soluble base (e.g., sodium carbonate, sodium bicarbonate, or sodium hydroxide). Suitable solvents for the reaction are aqueous solvent mixture such as dioxane/water or tetrahydrofuran/water. The reaction is carried out at temperatures ranging from 0° C. to 100° C., preferably at RT.

Generally, amines of formula 3 are commercially available e.g., benzylamine, N-ethylmethylamine 4-chlorophenylpiperazine, 4-phenoxypiperidine, 4-(4-methylphenyl)piperazine, 4-(4-fluorophenyl)-1,2,3,6-tetrahydropyridine, etc., are commercially available. Others can be prepared from starting materials such as 1-tert-butoxycarbonyl-4-hydroxypiperidine, 1-tert-butoxycarbonylisonipecotic acid, 1-tert-butoxycarbonylpiperazine, 1-benzyloxycarbonyl-4-piperidone, piperazine etc., by following the literature procedures such as those listed below.

For general piperazine synthesis and arylation, see, Saari, W. S., Halczenko, W., King, S. W., Huff, J. R., Guare, J. P., Hunt, C. A., Randall, W. C., Anderson, P. S., Lott, V. J., Taylor, D. A., Clineschmidt, B. U. *J. Med. Chem.*, 26, 1696, (1983); Kuipers, W., Wijngaarden, I., Knose, C. G., Amstel, M., Tulp, M. I., Zerman, A. *J. Med. Chem.*, 38, 1942, (1995); Verderame, M. *J. Med. Chem.*, 15, 693, (1972); and Herrin, T. R.; Paullik, J. M., Schuber, E. V., Geiszler, A. O. *J. Med. Chem.*, 18, 1216, (1975).

For indole-substituted piperidine analogs, see, Guillaume, J., Dumont, C., Laurent, J., Nedelec, L. *Eur. J. Med. Chem.*, 22, 33, (1987); Perregaard, J., Amt, J., Bogeso, K. P., Hyttel, J., Sanchez, C. *J. Med. Chem.*, 35, 1092, (1992); Andersen, K., Perregaard, J., Arnt, J., Nielsen, J. B., Begtrup, M. *J. Med. Chem.* 35, 4823, (1992), Bergman, J., Venemalm, L. *Tetrahedron*, 46, 6061, (1990); and Sasakura, K., Adachi, M., Sugasawa, T. *Synth. Comm.*, 18(3), 265 (1988).

For benzotriazole and benzisoxazole-substituted piperidine analogs, see, Sato, M., Arimoto, M., Ueno, K. *J. Med. Chem.*, 21, 1116, (1978); 4-benzoxazole-2-ylpiperidines Nestor, J. J. Jr., Horner, B. L., Ho, T. L. Jones, G. H., McRae, G. I., Vickery, B. H. *J. Med. Chem.*, 27, 320 (1984); and Strupczewski, J. T., Allen, R. C., Gardner, B. A., Schmid, B. L., Stache, U., Glamkowski, E. J., Jones, M. C., Ellis, D. B., Huger, F. P., Dunn, R. W. *J. Med. Chem.*, 28, 761, (1985) respectively.

For 4-(benzisothiazol-3-yl)piperidines and 4-(indazol-3-yl)piperidines, see, Fink, D. M., Strupczewski, J. T. *Tetrahedron Lett.*, 6525, (1993) and Strupczewski, J. T. European Patent 0135781, 1989.

For benzimidazole-substituted and related piperidine and piperazine analogs, see, Henning, R., Lattrell, R., Gerhards, H. J., Leven, M. *J. Med. Chem.*, 30, 814–9, (1987); Nomoto, Y., Obase, H., Takai, H., Hirata, T., Teranishi, M., Nakamura, J., Kubo, K. *Chem. Pharm. Bull.*, 38(6), 1591, (1990); Nestor, J. J., Horner, B. L., Ho, T. L., Jones, G. H., McRae, G. I., Vickery, B. H. *J. Med. Chem.*, 27, 320, (1984); Chen, J. J., Zhang, Y., Hammond, S., Dewdney, N., Ho. T., Lin, X., Browner, M. F., Castelhano, A. *Tetrahedron Lett.*, 1601 (1996) and Von Geldern, T. W., Hutchins, C., Kester, J. A., Wu-Wong, J. R., Chiou, W., Dixon, D. B., Opgenorth, T. J., *J. Med. Chem.*, 39, 957, (1996).

For 1,2,3,4-tetrahydro γ- or β-carbolines, see, Harbert, C. A., Plattner, J. J., Welch, W. M. *J. Med. Chem.*, 23, 635 (1980) and Still, I. W. J., Strautmanis, J. R. *Can. J. Chem.*, 68, 1408, (1990) and Ho, B. T., Mclsaac, W. M., Tansey, L. W. *J. Pharm. Sci.*, 58, 998, (1969).

For 4-arylthiazol-2-ylpiperidines and 4-arylimidazol-2-ylpiperidines, see, Von Geldern, T. W., Hutchins, C., Kester, J. A., Wu-Wong, J. R., Chiou, W., Dixon, D. B., Opgenorth, T. J. *J. Med. Chem.*, 39, 957 (1996).

For hydroxy-substituted pipecolic acid, see, Gillard, J., Abraham, A., Anderson, P. C., Beaulieu, P. L., Bogri, T., Bousquet, Y., Grenier, L., Guse, I., Lavallee, P. *J. Org. Chem.*, 61, 2226, (1996).

For 4-substituted 1,2,3,6-tetrahydropyridine analogs, see, Wustrow, D. J., Wise, L. D. *Synthesis*, 993, (1991); Perregaard, J., Moltzen, E. K., Meier, E., Sanchez, C. *J. Med. Chem.*, 38, 1998, (1995); and Bolttcher, H., Barnickel, G., Hausbery, H., Hasse, A. F., Seyfied, C. A., Eiermann, V. *J. Med. Chem.*, 35, 4020 (1992).

Alternatively, compound Ia can be prepared in one step as shown in Step 1,2 (alt.) by reacting the alpha-amino acetate 1 with a sulfamoyl chloride 4, utilizing the reaction conditions described in Step 2 above.

The sulfamoyl chloride 4 can be prepared from the corresponding amine 3 by proceeding as described in Step 1 above. It should be understood that if 3 is a heterocycloamino group substituted with an electron rich heteroaromatic ring, then it may become necessary, in some cases, to deactivate the heteroaromatic ring with a deactivating protecting group before carrying out the sulfonylating reaction. This is done to prevent sulfonylation from occurring on the heteroaromatic ring. For example, where 3 is a 4-(indol-3-yl)piperidino group, the indole nitrogen has to be protected by a deactivating protecting group (such as trimethylsilylethane-sulfonyl, acetyl, and the like) prior to converting it to the sulfamoyl chloride.

It will be recognized by one skilled in the art that a compound of formula Ia can be converted to a new compound of formula Ia using methods that do not affect the ester and sulfamide groups. For example, a compound of formula Ia where $R^3$ is hydrogen, can be converted to a corresponding compound of formula Ia where $R^3$ is not hydrogen, if required, either:

(a) by reacting compound Ia where $R^3$ is hydrogen with an alkylating agent $R^3X$, (where X is a leaving group such as chloro, bromo, mesylate, triflate, and the like under alkylating conditions) in the presence of a base (e.g., sodium carbonate, potassium carbonate, sodium hydride and the like) and at reaction temperatures ranging from 0° C. to 30° C. Suitable solvents for the reaction are THF, dioxane, N,N-dimethylformamide and the like; or (b) by reacting compound Ia with a hydroxy compound of formula $R^3OH$ in the presence of a trialkylphosphine or a triaryl phosphine, preferably triphenylphosphine, and a dialkyl azodicarboxylate such as diethyl or diisopropyl azodicarboxylate.

Additionally, a compound of formula Ia where $R^{20}$ and $R^{21}$ along with the nitrogen atom to which they are attached form a 4-piperidone ring can be reacted with trimethylsilyl trifluoromethanesulfonate and a nucleophile, such as a 3-unsubstituted pyrrole or indole, to give a compound of formula Ia where $R^{20}$ and $R^{21}$ along with the nitrogen atom to which they are attached is a 4-substituted-1,2,3,6-tetrahydropyridine ring, a 4,4-disubstituted-piperidino ring, or a 4-hydroxy-4-substituted piperidino ring depending on the reactivity of the nucleophile used. The reaction is carried out in a non-hydroxylic solvent, preferably methylene chloride or acetonitrile, at reaction temperatures ranging from −30° C. to 30° C.

A compound of formula Ia where $R^3$ is not hydrogen and $R^{21}$ may optionally be hydrogen, is prepared from an alpha-amino acetate 1 as shown in Scheme B.

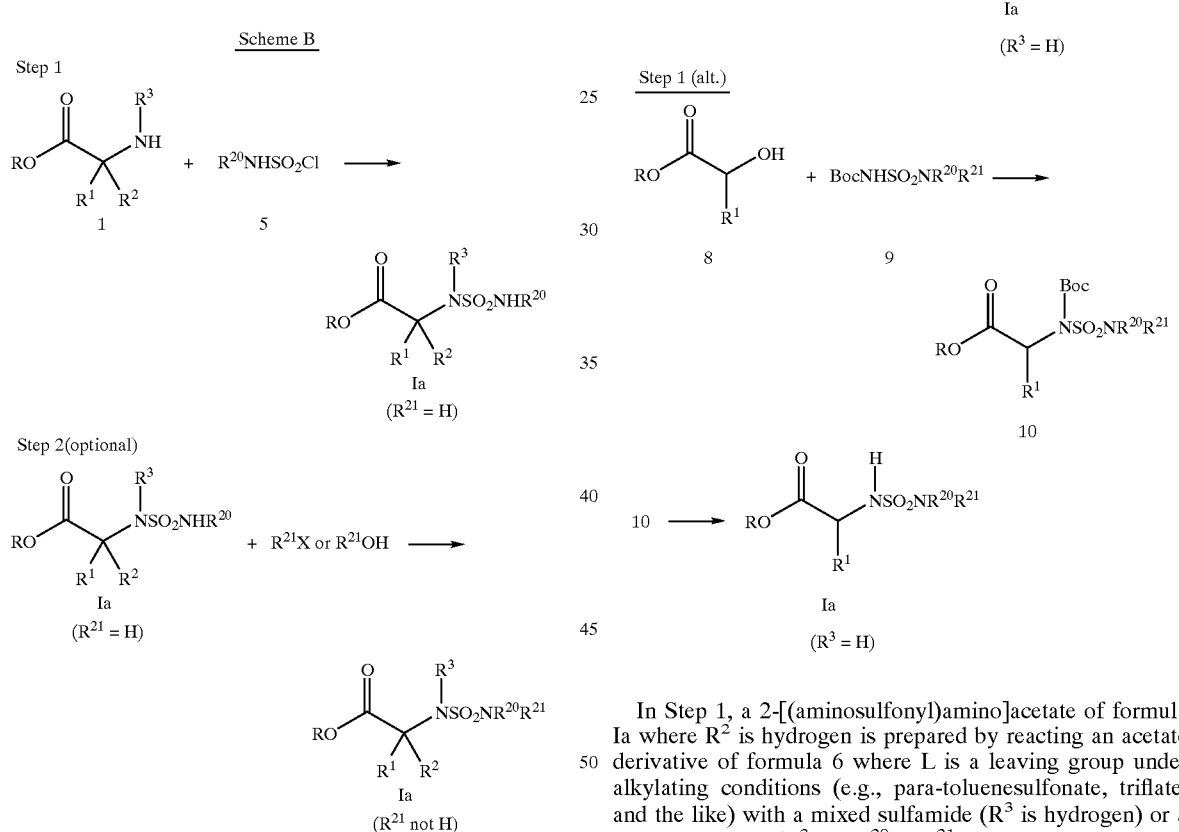

In Step 1, a compound of formula Ia where $R^3$ is not hydrogen and $R^{21}$ is hydrogen is prepared by proceeding as described in Step 1,2 (alt.) of Scheme A, but substituting a sulfamoyl chloride of formula 5 for a compound of formula 4.

The sulfamoyl chloride of formula 5 is prepared from a corresponding isocyanate, utilizing the reaction conditions such as those described in Kloek, J. A. and Leschinsky, K. L., *J. Org. Chem*, 46, 4028, (1976). The required isocyanate is commercially available or can be prepared by methods known to one skilled in the art.

In Step 2 (optional), a compound Ia where $R^{21}$ is hydrogen can be converted to a corresponding compound of formula Ia where $R^{21}$ is not hydrogen, by proceeding as described in Step 3 (optional) of Scheme A.

A compound of formula Ia where $R^2$ is hydrogen and $R^3$ may optionally be hydrogen is prepared from an alpha-hydroxyacetate 8 or its derivative 6 as shown in Scheme C.

In Step 1, a 2-[(aminosulfonyl)amino]acetate of formula Ia where $R^2$ is hydrogen is prepared by reacting an acetate derivative of formula 6 where L is a leaving group under alkylating conditions (e.g., para-toluenesulfonate, triflate, and the like) with a mixed sulfamide ($R^3$ is hydrogen) or a cyclic sulfamide ($R^3$ and $R^{20}$ or $R^{21}$ form an alkylene chain) of formula 7 at reaction temperatures ranging from −78° C. to −30° C. The reaction is carried out in the presence of a base (e.g., sodium hydride, potassium tert-butoxide, and the like) in a suitable polar aprotic organic solvent such as diethyl ether, tetrahydrofuran, and the like.

The mixed sulfamide 7 is prepared by heating the commercially available sulfamide ($NH_2SO_2NH_2$) with an amine of formula 3 (where $R^{20}$ and $R^{21}$ are as defined in the Summary of the Invention except hydrogen) in an aqueous medium. The cyclic sulfamide is prepared by reacting an alkylene diamine with sulfuryl chloride in aprotic organic solvent such as tetrahydrofuran.

Alternatively, compound Ia can be prepared in two steps as shown in Step 1 (alternative), by first preparing an N-tert-butoxycarbonyl-2-[(aminosulfonyl)amino]acetate of formula 10 which is then converted to a compound of formula Ia by removal of the N-protecting group. If compound 10 is the tert-butyl ester (i.e. R=tert-butyl), it is hydrolyzed under the reaction conditions utilized for the removal of the tert-butoxycarbonyl group thereby giving compound of formula (I) (where $R^{10}$=—OH) instead of compound of formula Ia. Compound 10 is prepared by reacting a 2-hydroxyacetate of formula 8 with an N-Boc protected sulfamide of formula 9 under reaction conditions such as those described in Step 3, method (b) of Scheme A.

Compound 9 is prepared by protecting the amino group in a corresponding sulfamide of formula 7 with di-tert-butyl dicarbonate.

The compound Ia where $R^3$ is hydrogen can be converted to a corresponding compound of formula Ia where $R^3$ is not hydrogen, by proceeding as described in Step 3 (optional) of Scheme A.

Preparation of Compounds of Formula (I)

Schemes D and E describe methods to prepare compounds of formula (I) from compounds of formula Ia.

Compounds of formula (I) where $R^{10}$ is hydroxy can be prepared by the methods shown in Scheme D.

hydrogen, the hydrolysis is carried out with aqueous lithium hydroxide in order to prevent racemization from occurring at this chiral center. The hydrolysis reaction proceeds either at ambient temperature or upon heating. Furthermore, if compound Ia is an acid labile ester, such as a tert-butyl ester, then the hydrolysis can be carried out in the presence of an acid (e.g., para-toluenesulfonic acid, trifluoroacetic acid, dry hydrochloric acid, and the like) and in an inert organic solvent such as methylene chloride, benzene, and the like.

Alternatively, compound (I) where $R^{10}$ is hydroxy may be prepared directly from the alpha-amino acid 11 (Z=hydrogen) or its corresponding salt (Z=sodium, ammonium, and the like) as shown in Step 1 (alt.). The acid 11 or its salt is first solubilized with a suitable solubilizing agent such as trimethylsilylcyanide and then reacted with a sulfamoyl chloride of formula 4.

Compounds of formula (I) where $R^{10}$ is an —$NR^{11}OR^{12}$ group where $R^{11}$ and $R^{12}$ are as defined in the Summary of the Invention are prepared by the methods shown in Scheme E.

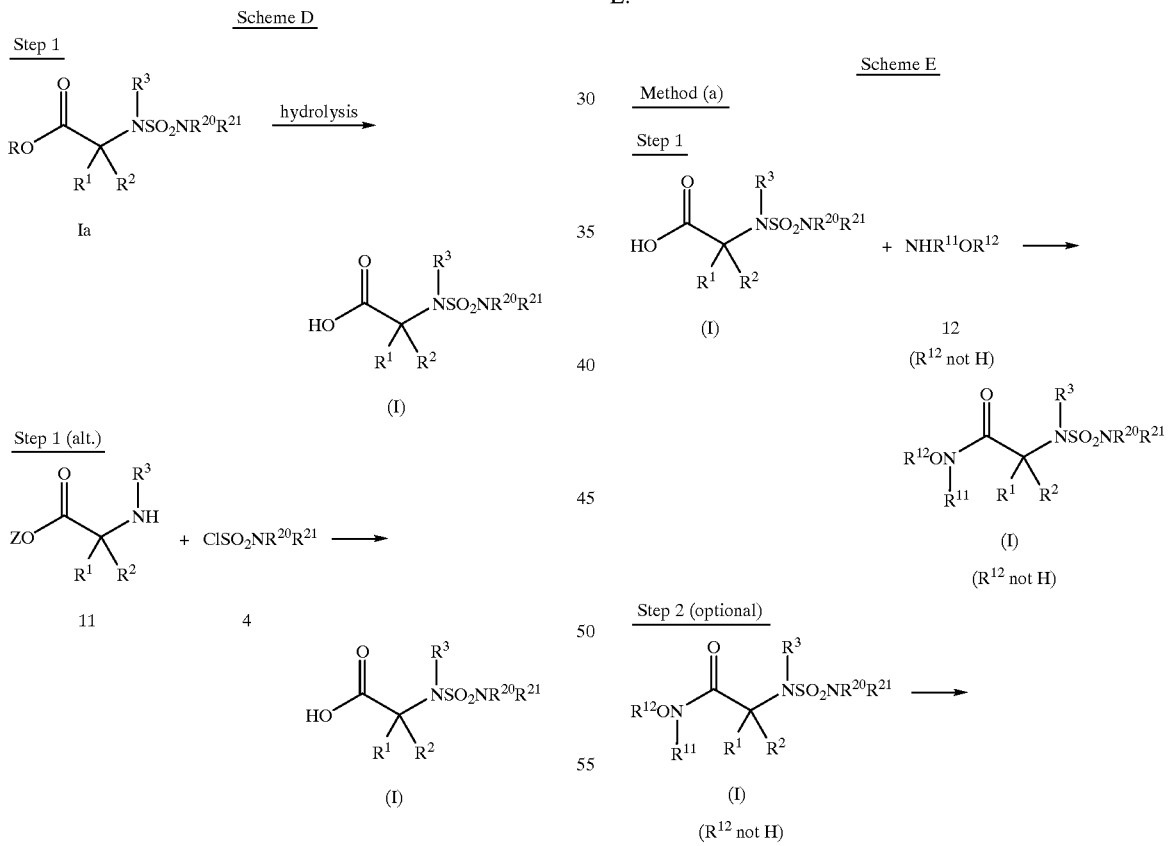

In Step 1, a compound of formula (I) where $R^{10}$ is hydroxy is prepared from a corresponding compound of formula Ia by hydrolysis of the ester group —OR. In general, the 10 hydrolysis is carried out in the presence of an aqueous base (e.g., sodium hydroxide, lithium hydroxide, and the like) in an alcoholic organic solvent such as methanol, ethanol, and the like. However, when compound Ia is optically active and the carbon atom to which $R^1$ and $R^2$ are attached is a chiral center and either $R^1$ or $R^2$ is

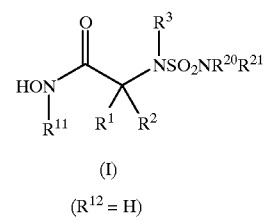

Method (b)

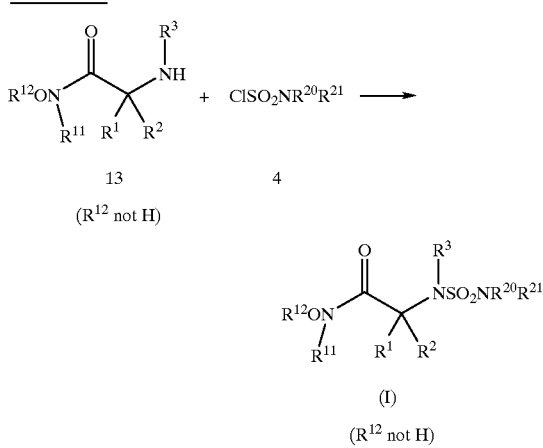

Method (c)

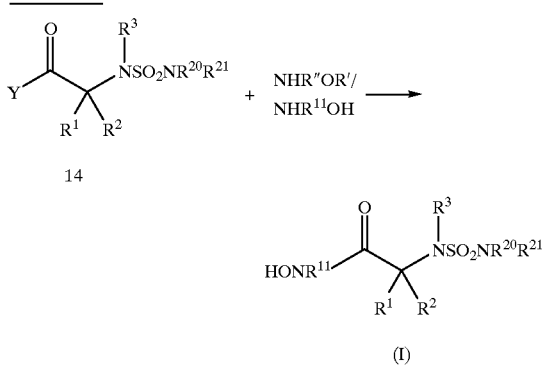

Method (d)

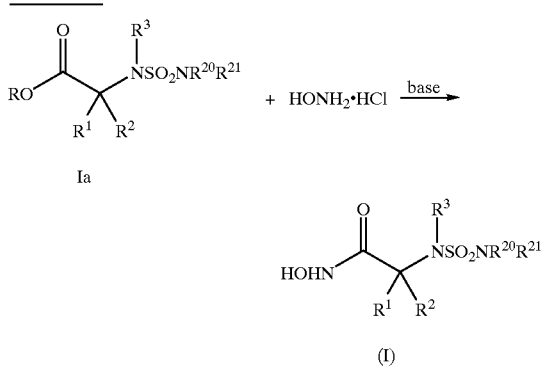

Method (a)

In Step 1, a compound of formula (I) where $R^{11}$ and $R^{12}$ are as defined in the Summary of the Invention except $R^{12}$ is not hydrogen is prepared by reacting a corresponding acid compound of formula (I) (where $R^{10}$=—OH) with an N,O-disubstituted hydroxylamine (e.g., N,O-dimethylhydroxylamine, and the like) or an O-substituted hydroxylamine (e.g., O-benzylhydroxylamine, O-tert-butylhydroxylamine, and the like). The reaction is carried out in the presence of a coupling agent (e.g., N,N-dicyclohexylcarbodiimide, N-ethyl-N'-(3-dimethylamino-propyl)-carbodiimide, and the like), an organic base (e.g., dimethylamino-pyridine, triethylamine, pyridine, N-methylmorpholine, and the like) and optionally hydroxy-benzotriazole. The reaction is carried out at temperatures ranging from 0° C. to 40° C., preferably ambient temperature. Suitable solvents for the reaction are methylene chloride, dichloroethane, DMF, and the like.

In Step 2, (optional), a compound of formula (I) where $R^{12}$ is hydrogen is prepared from the corresponding compound of formula (I) where $R^{12}$ is not hydrogen by removal of the $R^{12}$ group. The reaction conditions utilized depend on the nature of the $R^{12}$ group e.g., if $R^{12}$ is tert-butyl, then the reaction is carried out in an inert solvent such as dichloromethane, in the presence of an acid (e.g., dry hydrogen chloride, trifluoroacetic acid, and the like) at 0° C. to 25° C. If $R^{12}$ is benzyl, then hydrogenolysis conditions utilizing a metal catalyst such as palladium in an inert solvent such as ethyl acetate or tetrahydrofuran are required.

Alternatively, a compound of formula (I) where $R^{11}$ and $R^{12}$ are both hydrogen can be prepared by reacting a corresponding acid compound of formula (I) (where $R^{10}$=—OH) with an O-substituted hydroxylamine such as O-tert-butyldimethylsilylhydroxylamine, followed by treatment with an acid as described above. It will be recognized by one of ordinary skill in the art that compounds of formula (I) where either $R^{11}$ or $R^{12}$ is not hydrogen can be prepared by other procedures well known in the art. For example, a compound of formula (I) where $R^{11}$ is not hydrogen can be prepared by alkylating the corresponding compound of formula (I) where $R^{11}$ is hydrogen under the reaction conditions described in Scheme A above.

Method (b)

A compound of formula (I) where $R^{11}$ is as defined in the Summary of the Invention and $R^{12}$ is not hydrogen can be prepared by reacting an O-substituted or an N,O-disubstituted-N-hydroxy-2-amino acetamide of formula 13 with a sulfamoyl chloride 4 under the reaction conditions described in Step 1, 2 (alt.) of Scheme A. Compound 13 is prepared by proceeding as described in method (a) (above) but substituting a suitable orthogonally N-protected amino acid (e.g., N-CBZ-glycine or N-BOC-alpha amino isobutyric acid) for an acid of formula (I), followed by removal of the alpha amino protecting group.

Method (c)

A compound of formula (I) where $R^{10}$ is —$NR^{11}OH$ (where $R^{11}$ is as defined in the Summary of the Invention) can also be prepared by reacting an acyl derivative of formula 14 where Y is a leaving group under acylating conditions (e.g., chloro, succinimido, and the like) with a suitably protected hydroxylamine (e.g., N,O-bis-trimethylsilylhydroxylamine, N-methylhydroxylamine), or an aqueous solution of hydroxylamine. The reaction is carried out at reaction temperatures ranging from −30° C. to 25° C. and in a suitable organic solvent such as methylene chloride, tetrahydrofuran, tert-butanol, and the like. When N,O-bis(trimethylsilyl)hydroxylamine is used, compound (I) where $R^{10}$ is —NHOH is obtained directly since the trimethylsilyl group is cleaved during the acidic workup or upon the addition of methanol to the reaction mixture.

The acyl derivative 14 can be prepared from a corresponding compound of formula (I) where $R^{10}$ is hydroxy by methods known to those of ordinary skill in the art. For example, compound 14 where Y is chloro can be prepared by reacting compound (I) where $R^{10}$ is hydroxy with a chlorinating agent such as oxalyl chloride in a suitable organic solvent such as methylene chloride.

Method (d)

A compound of formula (I) where $R^{10}$ is —NHOH can be prepared directly by reacting a methyl 2-[(aminosulfonyl)amino]acetate of formula Ia where at least one of $R^1$ and $R^2$ is hydrogen with hydroxylamine by the method described in Naruse et. al., *J.Org. Chem.*, 59, 1358, (1994).

Utility, Testing, and Administration

Utility

The hydroyamic acids and the carboxylic acids of formula (I) inhibit mammalian matrix metalloproteases (MMP's), such as the stromelysins, gelatinases, matrilysin, collagenases and human metalloelastase. The compounds and compositions containing them are therefore useful in the treatment of diseases associated with the MMP-induced excessive degradation of matrix and connective tissue within the mammal, such as arthritis (rheumatoid arthritis and osteoarthritis), multiple sclerosis, bone resorptive diseases (such as osteoporosis), the enhanced collagen destruction associated with diabetes, chronic obstructive pulmonary disease, cerebral hemorrhaging associated with stroke, periodontal disease, corneal and gastric ulceration, ulceration of the skin, tumor invasion and metastasis, aneurysmal disease, and aberrant angiogenesis.

The compounds of formula (I) substantially inhibit the release of tumor necrosis factor (TNF) from cells, and are therefore useful for the treatment of conditions mediated by TNF, for example inflammation, fever, cardiovascular effects, hemorrhage, coagulation and acute phase response, cachexia and anorexia, acute infections, shock states, restenosis, graft versus host reactions and autoimmune disease. The compounds of the present invention may also inhibit the release of TNF without significant inhibition of the MMP's.

The compounds of this invention are therefore useful for treating a number of disease states, for example rheumatoid arthritis, multiple sclerosis, vascular disease, Type II diabetes, HIV, cachexia, psoriasis, allergy, hepatitis, inflammatory bowel disease, and cancer.

Testing

The ability of the compounds of formula (I) to inhibit matrix metalloprotease activity, such as the activity of collagenase-1, -2 and 3, stromelysin-1, gelatinases A and B, matrilysin and human metalloelastase may be demonstrated by a variety of in vitro assays known to those of ordinary skill in the art, such as the assay described in the MMP Enzymatic Assay described in FEBS, 296, 263, (1992) or modifications thereof as described in more detail in Example 32. It may also be assayed by the interleukin-1 stimulated cartilage explant assay and cartilage plug implantation assay as described in more detail in Examples 33 and 34.

The ability of the compounds of Formula (I) to inhibit the release of TNF may be assayed by an in vitro assay such as the TNF Monomac 6 assay and by in vivo assays such as the LPS induced TNF release assay and the TNF Receptor Shedding Immunoassay as described in more detail in Examples 35, 36, and 37.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of formula I may range from approximately 0.05–35 mg per kilogram body weight of the recipient per day; preferably about 0.3–20 mg/kg/day. Thus, for administration to a 70 kg person, the dosage range would most preferably be about 21 mg to 1.4 g per day.

In general. compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of formula (I) in combination with at least one pharmaceutically acceptable excipient. Acceptable excipients are non-toxic, aide administration, and do not adversely affect the therapeutic benefit of the compound of formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01–99.99 wt % of a compound of formula I based on the total formulation, with the balance being one or more suitable pharmaceutical excipients. Preferably, the compound is present at a level of about 1–80 wt %. Representative pharmaceutical formulations containing a compound of formula I are described in Example 30.

EXAMPLES

The following preparations and examples are given to enable those skilled in the art to more clearly understand and to practice the present invention. They should not be considered as limiting the scope of the invention, but merely as being illustrative and representative thereof.

Abbreviations used in the examples are defined as follows: "HCl" for hydrochloric acid, "DMF" for dimethylformamide, "NaOH" for sodium hydroxide, "DMSO" for dimethylsulfoxide, "MgSO$_4$" for magnesium sulfate, "RT" for room temperature, "PTLC" for preparatory thin layer chromatography, "SiO$_2$" for silica gel, "EtOAc" for ethyl acetate, "APMA" for aminophenyl-mercuric acetate, "IL-1" for interleukin-1, and "RPMI" for Roswell Park Memorial Institute.

SYNTHETIC EXAMPLES

Example 1

Synthesis of ethyl 2-[benzyl-(morpholine-4-sulfonyl) amino]acetate

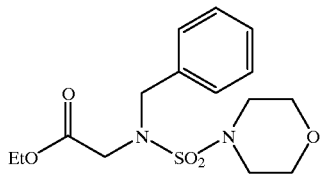

Step 1

A solution of triethylamine (2.0 ml, 14.4 mmol) and N-benzylglycine ethyl ester (2.25 ml, 12.0 mmol) in methylene chloride (5 ml) was added to a solution of sulfuryl chloride (0.96 ml, 12.0 mmol) in methylene chloride (30 ml) at −78° C. The reaction mixture was stirred at −78° C. for 4 h and then concentrated. Ether (75 ml) was added and the resulting precipitate was filtered. The organic layer was washed with 1M HCl and brine, dried over MgSO$_4$ and concentrated in vacuo to give ethyl 2-[benzyl-(chlorosulfonyl)amino]acetate as a colorless oil (69%).

Step 2

A solution of morpholine (1.05 ml, 12 mmol) and triethylamine (1.84 ml, 12 mmol) in methylene chloride (10 ml) was added to a solution of ethyl 2-[benzyl-(chlorosulfonyl) amino]acetate (2.3 g, 8.3 mmol), [prepared as described in Step 1 above], in methylene chloride (30 ml) at 0° C. The reaction mixture was slowly allowed to warm to RT and after 6h 1M HCl was added. The product was extracted into methylene chloride, washed with brine, and dried over MgSO$_4$. The organics were removed in vacuo and the crude product was chromatographed (PTLC, SiO$_2$, 25% ethyl acetate/hexane) to give ethyl 2-[benzyl-(morpholine-4-sulfonyl)amino]acetate as a colorless oil (6%).

Proceeding as described in Example 1 above, but substituting morpholine with:

4-methoxypiperidine;
benzylmethylamine; and
4-phenoxypiperidine, gave respectively,
ethyl 2-[benzyl-(4-methoxypiperidine-1-sulfonyl)amino] acetate (via methylation of the corresponding 4-hydroxypiperidine analog);
ethyl 2-[benzyl-(benzylmethylaminosulfonyl)amino] acetate;
ethyl 2-{[benzyl-(4-phenoxy)piperidine-1-sulfonyl] amino}acetate.

Example 2

Synthesis of methyl 2-(R)-{[4-(5-chloropyridin-2-yloxy) piperidine-1-sulfonyl]amino}-3-methylbutyrate

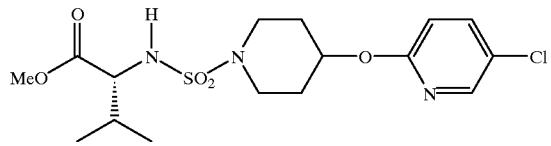

Step 1

Chlorosulfonic acid (0.23 ml, 3.46 mmol) was added to a solution of (D)-valine methyl ester (1.36 g, 10.37 mmol) in methylene chloride (9 ml) at 0° C. and the reaction mixture was allowed to warm to RT. After 1.5 h, the solvent was removed in vacuo and the resulting solid was slurried in benzene (10 ml). Phosphorus pentachloride (0.72 g, 3.46 mmol) was added and the reaction mixture was heated at reflux. After 45 min., the solvent was evaporated and ether (75 ml) was added to the crude product. The solid was filtered and the filtrate was concentrated to give (D)-valinesulfamoyl chloride methyl ester as a colorless oil (87%).

Step 2:

(D)-valinesulfamoyl chloride methyl ester (1.3 g, 5.6 mmol) [prepared as described in Step 1 above] was added to a solution of 4-(5-chloropyridin-2-yloxy)piperidine (1.2 g, 5.6 mmol) and triethylamine (3.21 ml, 22.5 mmol) in tetrahydrofuran (50 ml) at −78° C. After 2 h, the reaction mixture was diluted with ethyl acetate and then quenched with 0.5 M ammonium chloride. The organic layer was washed with brine, dried over MgSO$_4$, and concentrated in vacuo to give methyl 2-(R)-{[4-(5-chloropyridin-2-yloxy) piperidine-1-sulfonyl]amino}-3-methylbutyrate as a pale yellow oil (75%).

Proceeding as described above but substituting 4-(5-chloropyridin-2-yloxy)piperidine with:

4-(4-chlorophenoxy)piperidine;
4-(4-fluorophenoxy)piperidine;
4-(4-chlorophenyl)piperazine;
4-[(4-benzyloxy)phenyl]piperazine;
4-(5-chloropyridin-2-yl)piperazine;
4-[(2-phenylbenzoxazol-5-yl)piperazine;
4-[(4-chloyobenzylaminocarbonyl)methyl ]piperidine, and
4-(4-phenylimidazol-2-yl)piperidine gave, respectively,
methyl 2-(R)-{[4-(4-chlorophenoxy)piperidine-1-sulfonyl]amino}-3-methylbutyrate;
methyl 2-(R)-{[4-(4-fluorophenoxy)piperidine-1-sulfonyl]amino}-3-methylbutyrate;
methyl 2-(R)-{[4-(4-chlorophenyl)piperazine-1-sulfonyl] amino}-3-methylbutyrate;
methyl 2-(R)-{[4-(4-benzyloxyphenyl]piperazine-1-sulfonyl]amino}-3-methylbutyrate;
methyl 2-(R)-{[4-(5-chloropyridin-2-yl)piperazine-1-sulfonyl]amino}-3-methylbutyrate;
methyl 2-(R)-{4-[(2-phenylbenzoxazol-5-yl)piperazine-1-sulfonyl]amino}-3-methylbutyrate;

methyl 2-(R)-{[4-[(4-chlorobenzylaminocarbonyl) methyl]piperidine-1-sulfonyl]amino}-3-methylbutyrate; and methyl 2-(R)-{[4-(4-phenylimidazol-2-yl)piperidine-1-sulfonyl]amino}-3-methylbutyrate.

Example 3

Synthesis of methyl 1-[4-(4-chlorophenyl)piperazine-1-sulfonyl]-piperidine-2-(RS)-carboxylate

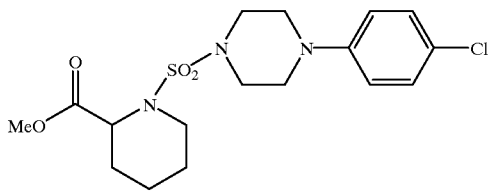

Step 1

Chlorosulfonic acid (3.0 ml, 44.0 mmol) was added dropwise to a solution of 4-(4chlorophenyl)piperazine (7.12 g, 44.0 mmol) and triethylamine (12.26 ml, 88.0 mmol) in methylene chloride (50 ml) at 0° C. The reaction mixture was stirred overnight at RT and then concentrated in vacuo. The residue was washed with ether, dried under high vacuum for 10 min., and then redissolved in benzene (80 ml). Phosphorus pentachloride (9.24 g, 44.0 mmol) was added and the reaction mixture was heated at reflux for 1 h. The reaction mixture was diluted with ethyl acetate (250 ml) and the organic layer was washed with 5% citric acid, sat. sodium bicarbonate, and brine, and dried over $MgSO_4$. The solvent was evaporated in vacuo and the residue was boiled in ether for 5 min. Filtration of the solid material gave 4-(4chlorophenyl)piperazinesulfamoyl chloride as a tan solid (40%), mp 170.5–172.0° C.

Step 2

Triethylamine (0.59 ml, 4.22 mmol) was added dropwise to a mixture of 4-(4chlorophenyl)piperazinesulfamoyl chloride (0.56 g, 1.9 mmol), [prepared as described in Step 1 above] and methyl piperidine-2-(RS)-carboxylate HCl salt (0.38 g, 2.11 mmol) in tetrahydrofuran (15 ml) and the reaction mixture was heated at reflux. After 19 h, additional amounts of methyl piperidine-2-carboxylate HCl salt (189 mg) and triethylamine (0.15 ml) were added and the heating was continued. After 5 h, the reaction mixture was cooled, diluted with methylene chloride (40 ml), and washed with 10% citric acid, water, and brine, and dried over $MgSO_4$. The organics were removed in vacuo and the residue was chromatographed ($SiO_2$, 10–35% ethyl acetate/hexane) to yield methyl 1-[4-(4-chlorophenyl)piperazine-1-sulfonyl] piperidine-2-(RS)-carboxylate as a colorless glass (21%).

1. Proceeding as described in Step 2 above, but substituting 4-(4-chlorophenyl)piperazine with:
   4-phenoxypiperidine; and
   4-phenylthiopiperidine, gave respectively,
   methyl 1-[4-phenoxypiperidine-1-sulfonyl]piperidine-2-(RS)-carboxylate;
   methyl 1-[4-phenylthiopiperidine-1-sulfonyl]piperidine-2-(RS)-carboxylate;
2. Proceeding as described in Example 3 above, but substituting 4-(4-chlorophenyl)piperazine with:
   4-(pyridin-4-ylthio)piperidine; and
   4-(4-chlorobenzoyl)piperidine; and
   methyl piperidine-2-(RS)-carboxylate HCl salt with methyl piperidine-2-(R)-carboxylate HCl salt, gave respectively,
   methyl 1-[4-(pyridin-4-ylthio)piperidine-1-sulfonyl] piperidine-2-(R)-carboxylate; and
   methyl 1-[4-(4-chlorobenzoyl)piperidine-1-sulfonyl] piperidine-2-(R)-carboxylate.
3. Proceeding as described in Example 3 above, but substituting 4-(4-chlorophenyl)piperazine with 4-(5-chloropyridin-2-yl)piperazine and methyl piperidine-2-(RS)-carboxylate HCl salt with methyl 2-(RS)-amino-4-phenylbutyrate HCl salt, gave methyl 2-(RS)-{[4-(5-chloropyridin-2-yl)piperazine-1-sulfonyl]amino}-4-phenylbutyrate.

Example 4

Synthesis of tert-butyl 2-(R)-{methyl-[4-(4-chlorobenzoyl) piperidine-1-sulfonyl]amino}-3-methylbutyrate

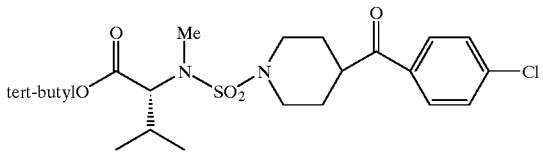

Step 1

N,N-dimethylformamide di-tert-butyl acetal (134 mg, 0.66 mmol) was added to a solution of 2-(R)-{[4-(4-chlorobenzoyl)piperidine-1-sulfonyl]amino}-3-methylbutyric acid (90 mg, 0.22 mmol) in toluene (2.5 ml) at 90° C. The reaction was stirred for 3 h and concentrated to give tert-butyl 2-(R)-{[4-(4-chlorobenzoyl)piperidine-1-sulfonyl]amino}-3-methylbutyric acid that was used in the next step with no further purification.

Step 2

Anhydrous potassium carbonate (152 mg, 1.1 mmol) and iodomethane (0.034 ml, 0.5 mmol) were added to a solution of tert-butyl 2-(R)-{[4-(4-chlorobenzoyl)piperidine-1-sulfonyl]amino}-3-methylbutyrate (100 mg, 0.22 mmol) in DMF (1.5 Ml) at RT. After 3 h, the reaction mixture was diluted with ethyl acetate (30 ml) and then washed with 0.1M HCl and brine, and dried over $MgSO_4$. The solvent was removed in vacuo and the residue was chromatographed (PTLC, $SiO_2$, 25% ethyl acetate/hexane) to give tert-butyl 2-(R)-{methyl-[4-(4-chlorobenzoyl)piperidine-1-sulfnyl] amino}-3-methylbutyrate as a colorless oil (63%).

Proceeding as described in Example, Step 2 above, but substituting tert-butyl 2-(R)-{[4-(4-chlorobenzoyl) piperdine-1-sulfonyl]amino}-3-methylbutyrate with methyl 2-(RS)-{[4-(5-chloropyridin-2-yl)piperazine-1-sulfonyl] amino}-4-phenylbutyrate (prepared as described in Example 3 above) gave methyl 2-(RS)-{methyl-[4-(5-chloropyridin-2-yl)piperazine-1-sulfonyl]amino}-4-phenylbutyrate.

Example 5

Synthesis of methyl 2-(R)-{(pyridin-3-ylmethyl)-[4-(4-bromophenyl)piperidine-1-sulfonyl]amino}-3-methylbutyrate

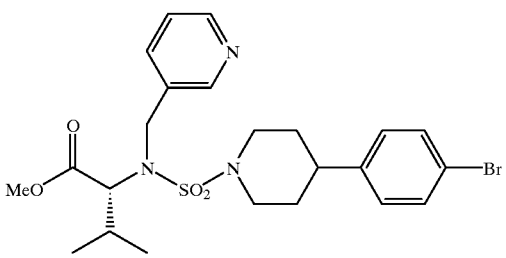

Tri-n-butylphosphine (0.37 ml, 1.5 mmol) was added to a solution of methyl 2-(R)-{[4-(4-bromophenyl)piperidine-1-sulfonyl]amino}-3-methylbutyrate (560 mg, 1.25 mmol), 3-pyridylcarbinol (0.15 ml, 1.5 mmol), and 1,1'-(azodicarbonyl)piperidine (377 mg, 1.5 mmol) in benzene (30 ml). After stirring at RT for 48 h, the reaction mixture was concentrated and the residue was triturated with ether (60 ml). After filtering off the solids, the ether layer was concentrated in vacuo and the residue was chromatographed (SiO$_2$, 40% ethyl acetate/hexane) to give methyl 2-(R)-{(pyridin-3-ylmethyl)-[4-(4-bromophenyl)piperidine-1-sulfonyl]amino}-3-methylbutyrate as a colorless oil (41%).

Proceeding as described in Example 5 above, but substituting, 3-pyridylcarbinol with 3-(3-pyridyl)propanol gave methyl 2-(R)-{3-(pyridin-3-yl)propyl-[4-(4-bromophenyl)-piperidine-1-sulfonyl]amino}-3-methylbutyrate.

Example 6
Synthesis of methyl 2-(R)-[benzyl-(benzylmethylaminosulfonyl)-amino]-3-methylbutyrate

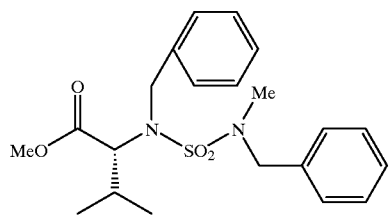

Step 1
A solution of (D)-N-benzylvaline methyl ester (1.5 g, 6.78 mmol) and triethylamine (1.13 ml, 8.14 mmol) in ether (25 ml) was added to a solution of methylaminosulfonylchloride (0.97 g, 7.5 mmol) [prepared as described in Kloek, J. A. and Leschinsky, K. L., *J. Org. Chem*, 46, 4028, (1976)] in ether (25 ml) at RT. After 6 h, the reaction was quenched with 1 M HCl and the product was extracted into ether. The combined organic layers were washed with brine, dried over MgSO$_4$, and concentrated in vacuo to give methyl 2-(R)-[benzyl-(methylamino-sulfonyl)amino]-3-methylbutyrate as a colorless oil (86%).

Step 2
Benzyl iodide (280 mg, 1.28 mmol) and anhydrous potassium carbonate (440 mg, 3.2 mmol) were added to a solution of methyl 2-(R)-([benzyl-(methylaminosulfonyl)amino]-3-methylbutyrate (200 mg, 0.64 mmol), [prepared as described in Step 1 above] in DMF (3 ml) at RT. After 96 h, 1 M HCl was added and the product was extracted into ethyl acetate. The organic layer was washed with dilute sodium thiosulfate and brine and dried over MgSO$_4$. The organics were removed in vacuo and the residue was chromatographed (PTLC, SiO$_2$, 20% ethyl acetate/hexane) to give methyl 2-(R)-[benzyl-(benzylmethylaminosulfonyl)amino]-3-methylbutyrate as a colorless oil (60%).

Example 7
Synthesis of methyl 2-(R)-{[4-(4-chlorophenyl)piperazine-1-sulfonyl]amino}propionate

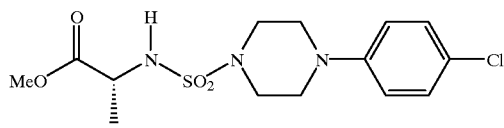

Step 1
A mixture of 4-(4-chlorophenyl)piperazine (6.63 g, 33.7 mmol) and sulfamide (3.89 g, 40.5 mmol) in water (10 ml) was heated at 120° C. After 96 h, the reaction mixture was cooled to RT, diluted with ethyl acetate (100 ml). Water (100 ml) was added and the reaction mixture was stirred vigorously for several minutes. The solid was filtered to give [4-(4-chlorophenyl)-piperazine-1-sulfonyl]amine as a white powder (59%), mp 218.0–220.0° C.

Step 2
A solution of potassium tert-butoxide (0.87 ml, 1M in tetrahydrofuran) was added to a solution of [4-(4-chlorophenyl)piperazine-1-sulfonyl]amine (200 mg, 0.73 mmol), [prepared as described in Step 1 above], in tetrahydrofuran (10 ml) at −60° C. After 10 min., a solution of the triflate derivative of methyl (S)-lactate (604 mg, 2.56 mmol) in tetrahydrofuran (3 ml) was added and the reaction mixture was allowed to warm to −30° C. over 30 min. The reaction mixture was quenched with saturated ammonium chloride and the product was extracted into ethyl acetate. The solvent was removed in vacuo and the residue was chromatographed (SiO$_2$, 30% ethyl acetate/hexane) to give methyl 2-(R)-{[4-(4-chlorophenyl)piperazine-1-sulfonyl]-amino}propionate as a colorless oil (66%).

Proceeding as described in Example 7, Step 2 above, but substituting potassium tert-butoxide and [4-(4-chlorophenyl)piperazine-1-sulfonyl]amine with tert-butyl chloroacetate and 5-(biphenyl-4-ylmethyl)-1,1-dioxo-1,2,5-thiadiazolidine gave tert-butyl 5-(biphenyl-4-ylmethyl)-1,1-dioxo-1,2,5-thiadiazolidine-2-acetate.

Example 8
Synthesis of 2-(R)-{[4-(4-chlorophenyl)piperazine-1-sulfonyl]amino}-3-phenylpropionic acid

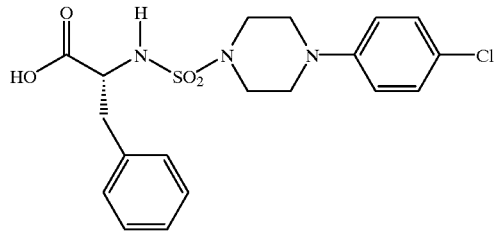

Step 1
Di-tert-butyl dicarbonate (2.85 g, 13 mmol) and 4-dimethylaminopyridine (90 mg, 0.7 mmol) were added to a solution of [4-(4-chlorophenyl)piperazine-1-sulfonyl]amine (3.0 g, 15.2 mmol) in tetrahydrofuran (60 ml) at RT. After 12 h, the reaction mixture was concentrated and the residue was chromatographed (SiO$_2$, 25% ethyl acetate/hexane) to give N-tert-butoxycarbonyl-[4-(4-chlorophenyl)piperazine-1-sulfonyl]amine as a white powder (55%).

Step 2
Diethyl azodicarboxylate (0.35 ml, 2.24 mmol) was added to a solution of triphenylphosphine (586 mg, 2.24 mmol) in tetrahydrofuran (20 ml) at −78° C. and the reaction mixture was stirred for 5 min. Tert-butyl 3-(L)-phenyl lactate (800 mg, 2.13 mmol) was added and the stirring was continued for an additional 5 min. A solution of N-tert-butoxycarbonyl-[4-(4chlorophenyl)piperazine-1-sulfonyl] amine (757 mg, 3.41 mmol), [prepared as described in Step 1 above] in tetrahydrofuran (5 ml) was added via syringe. The reaction mixture was stirred overnight at RT and then concentrated in vacuo. The residue was chromatographed (SiO$_2$, 14% ethyl acetate/hexane) to give tert-butyl 2-(R)-{tert-butoxycarbonyl-[4-(4-chlorophenyl)piperazine-1-sulfonyl]amino}-3-phenylpropionate as a pale yellow oil (88%).

Step 3

A solution of tert-butyl 2-(R)-{tert-butoxycarbonyl-[4-(4-chlorophenyl)piperazine-1sulfonyl]amino}-3-phenylpropionate (579 mg, 1.15 mmol), [prepared as described in Step 2 above], in methylene chloride (20 ml) was saturated with dry hydrogen chloride gas at 0° C. The reaction vessel was sealed and the reaction mixture was stirred at RT. After 72 h, the reaction mixture was vented with nitrogen and then concentrated in vacuo. The residue was treated with methylene chloride and the product was filtered to give 2-(R)-{[4-(4-chlorophenyl)piperazine-1-sulfonyl]amino}-3-phenylpropionic acid as a white solid (74%), mp 176.0–178.0 ° C.

Proceeding as described in Example 8, Step 3 above, but substituting tert-butyl 5-(biphenyl-4-ylmethyl)-1,1-dioxo-1,2,5-thiadiazolidine-2-acetate (prepared as described in Example 7, Step 2 above) gave 5-(biphenyl-4-ylmethyl)-1,1-dioxo-1,2,5-thiadiazolidine-2-acetate.

Example 9

Synthesis of 2-(R)-{[4-(4-chlorophenoxy)piperidine-1-sulfonyl]amino}-3-methylbutyric acid

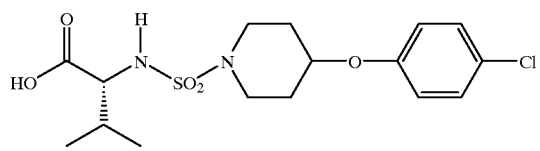

Trimethylsilyl cyanide (1.6 ml, 12.6 mmol) was added to a suspension of (D)-valine (0.89 g, 7.6 mmol) in acetonitrile and the reaction mixture was treated at reflux. After 20 min., the reaction mixture turned homogeneous. 4-(4-chlorophenoxy)piperidinesulfamoyl chloride (1.4 g, 4.5 mmol) [prepared as described in Example 3, Step 1, substituting 4-(4chlorophenyl)piperazine with 4-(4-chlorophenoxy)piperidine]was added and the reaction mixture was stirred at reflux overnight. After concentration, methanol (25 ml) was added and the reaction mixture was stirred for 30 min. The organic layer was evaporated and the residue was chromatographed (SiO$_2$, 1.5% methanol/methylene chloride) to give 2-(R)-{[4-(4-chlorophenoxy)piperidine-1-sulfonyl]amino}-3-methylbutyric acid as a colorless oil (78%).

1. Proceeding as described above but substituting (D)-valine and 4-(4-chlorophenoxy)-piperidinesulfamoyl chloride with H-(D)-lysine-Cbz-OH and 4-(4-chlorophenyl)piperazinesulfamoyl chloride [prepared as described in Example 3, Step 1] respectively, gave 6-(benzyloxycarbonyl)amino-2-(R)-{[4-(4-chlorophenyl)piperazine-1-sulfonyl]amino}hexanoic acid.

2. Proceeding as described above but substituting D)-valine and 4-(4-chlorophenoxy)piperidinesulfamoyl chloride with 4-aminopiperidine-4-carboxylic acid bis-HCl salt and 4-(4-chlorobenzoyl)piperidinesulfamoyl chloride respectively, using 5 equiv. of trimethylsilyl cyanide and then quenching the crude reaction mixture with Boc anhydride in the presence of sodium hydroxide gave 1-tert-butoxycarbonyl-4-{[4-(4-chlorobenzoyl)piperidine-1-sulfonyl]amino}piperidine-4-carboxylic acid.

Example 10

Synthesis of N-hydroxy-1-[4-(4-chlorobenzoyl)piperidine-1-sulfonyl]piperidine-2-(R)-carboxamide

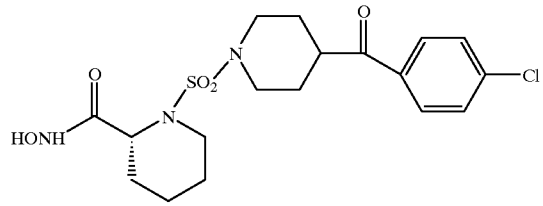

Step 1

O-tert-butylhydroxylamine hydrochloride (127 mg, 1.01 mmol), 1-(3-dimethylaminopropyl)-3-ethylcaibodiimide hydrochloride (129 mg, 0.67 mmol), N,N-dimethylaminopyridine (41 mg, 0.34 mmol), and N-methylmorpholine (0.15 ml, 1.3 mmol) were added to a solution of 1-[4-(4-chlorobenzoyl)piperidine-1-sulfonyl]piperidine-2-(R)-carboxylic acid (140 mg, 0.34 mmol), [prepared by proceeding as described in Example 9, but replacing D-valine and 4-(4chlorophenoxy)piperidinesulfamoyl chloride with D-pipecolinic acid and 4-(4-chlorobenzoylpiperidinesulfamoyl chloride, respectively], in methylene chloride (2 ml). After stirring overnight, the reaction mixture was diluted with ethyl acetate, washed with 1M HCl, and brine, and dried over MgSO$_4$. The organics were evaporated in vacuo and the residue was chromatographed (PTLC, SiO$_2$, 40% ethyl acetate/hexane) to give N-tert-butoxy-1-[4-(4-chlorobenzoyl)piperidine-1-sulfonyl]piperidine-2-(R)-carboxamide as a white solid (65%).

Step 2

A solution of N-tert-butoxy-1-[4-(4-chlorobenzoyl)piperidine-1-sulfonyl]piperidine-2-(R)-carboxamide (100 mg, 0.22 mmol), [prepared as described in Step 1 above], in 1,2-dichloroethane (10 ml) was cooled to −30° C. and HCl gas was bubbled through it for 10 min. The reaction vessel was then sealed and stirred at RT. After 2 days, the reaction mixture was vented with nitrogen and then concentrated in vacuo. The residue was chromatographed (PTLC, SiO$_2$, 10% methanol/methylene chloride) to give N-hydroxy-1-[4-(4-chlorobenzoyl)piperidine-1-sulfonyl]piperidine-2-(R)-carboxamide as a white solid (51%), mp 84.4–86.4° C.

Proceeding as described in Example 10 Step 1 above but substituting 1-[4-(4-chlorobenzoyl)piperidine-1-sulfonyl]piperidine-2-(R)-carboxylic acid with 1-tert-butoxycarbonyl-4-{[4-(4-chlorobenzoyl)piperidine-1-sulfonyl]amino}piperidine-4-carboxylic acid [prepared as described in Example 9 above] gave N-tert-butoxy-1-tert-butoxycarbonyl-4-{[4-(4-chlorobenzoyl)piperidine-1-sulfonyl]amino}piperidine-4-carboxamide.

Example 11

Synthesis of N-hydroxy-2-(R)-{[4-(5-chloropyridin-2-yloxy)piperidine-1-sulfonyl]amino}-3-methylbutyramide

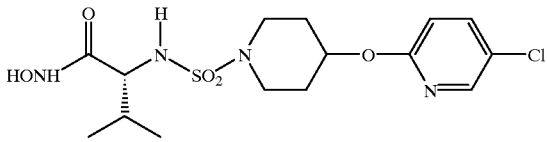

Step 1

A solution of lithium hydroxide monohydrate (0.35 g, 8.3 mmol) in water (5 ml) was added to a solution of methyl (R)-2-{[4-(5-chloropyridin-2-yloxy)piperidine-1-sulfonyl]amino}-3-methylbutyrate (1.7 g, 4.2 mmol), [prepared as described in Example 2], in methanol/tetrahydrofuran (1:1, 25 ml) and the reaction mixture was warmed to 45° C. After stirring overnight, reaction mixture was adjusted to pH 6 using 1M HCl and the product was extracted into ethyl acetate. The organic layer was washed with brine, dried over MgSO$_4$, and concentrated in vacuo. The residue was chromatographed (SiO$_2$, 2% methanol/methylene chloride) to give 2-(R)-{[4-(5-chloropyridin-2-yloxy)piperidine-1-sulfonyl]amino}-3-methylbutyric acid as a white gummy solid (66%).

Step 2

Oxalyl chloride (0.58 ml, 6.7 mmol) and DMF (few drops) were added to a solution of (R)-2-{[4-(5-chloropyridin-2-yloxy)piperidine-1sulfonyl)amino}-3-methylbutyric acid (1.05 g, 2.7 mmol), [prepared as described in Step 1 above], in methylene chloride (85 ml) and the reaction mixture was stirred overnight at RT. After removal of the organics, the residue was redissolved in methylene chloride (40 ml) and N,O-bis-trimethylsilylhydroxylamine (1.7 g, 9.4 mmol) was added. After 3 h, the reaction was concentrated, methanol (20 ml) was added and after stirring for an additional 30 min., the solvent was removed in vacuo. The residue was dissolved in ethyl acetate and washed with water and brine, dried over MgSO$_4$, and concentrated. Chromatography (SiO$_2$, 1–2% methanol/methylene chloride) gave N-hydroxy-2-(R)-{[4-(5-chloropyridin-2-yl-oxy)piperidine-1-sulfonyl]amino}-3-methylbutyramide as a white solid (35%), mp 97.0–98.4° C.

1. Proceeding as described in Example 11 above, but substituting methyl (R)-2-{[4-(5-chloropyridin-2-yloxy)piperidine-1-sulfonyl]amino}-3-methylbutyrate with:

methyl 2-(R)-{[4-(4-chlorophenoxy)piperidine-1-sulfonyl]amino}-3-methylbutyrate (see Example 2);

methyl 2-(R)-{[4-(4-fluorophenoxy)piperidine-1-sulfonyl]amino}-3-methylbutyrate (see Example 2);

methyl 2-(R)-{[4-(4-chlorophenyl)piperazine-1-sulfonyl]amino}-3-methylbutyrate;

methyl 2-(R)-{[4-[(4-benzyloxy)phenyl]piperazine-1-sulfonyl]amino}-3-methylbutyrate (see Example 2);

methyl 2-(R)-{[4-(5-chloropyridin-2-yl)piperazine-1-sulfonyl]amino -3-methylbutyrate (see Example 2);

methyl 2-(R)-{[4-(2-phenylbenzoxazol-5-yl)piperazine-1-sulfonyl]amino}-3-methylbutyrate (see Example 2);

methyl 2-(R)-{[4-(4-phenylimidazol-2-yl)piperidine-1-sulfonyl]amino}-3-methylbutyrate (see Example 2);

methyl 1-[4-phenoxypiperidine-1-sulfonyl]piperidine-2-(RS)-carboxylate (see Example 3 above);

methyl 2-(RS)-{methyl-[4-(5-chloropyridin-2-yl)piperazine-1-sulfonyl]amino}-4-phenylbutyrate (see Example 4 above);

methyl 2-(R)-{3-(pyridin-3-yl)propyl-[4-(4-bromophenyl)piperidine-1-sulfonyl]amino}-3-methybutyrate (see Example 5 above); and methyl 2-(R)-{(pyridin-3-ylmethyl)-[4-(4-bromophenyl)piperidine-1-sulfonyl]amino}-3-methybutyrate (see Example 5 above), gave respectively, N-hydroxy-2-(R)-{[4-(4-chlorophenoxy)piperidine-1-sulfonyl]amino}-3-methylbutyramide;

N-hydroxy-2-(R)-{[4-(4-fluorophenoxy)piperidine-1-sulfonyl]amino}-3-methylbutyramide N-hydroxy-2-(R)-{[4-(4-chlorophenyl)piperazine-1-sulfonyl]amino}-3-methylbutyramide;

N-hydroxy-2-(R)-{[4-(4-benzyloxy)phenyl]piperazine-1-sulfonyl]amino}-3-methylbutyramide;

N-hydroxy-2-(R)-{[4-(5-chloropyridin-2-yl)piperazine-1-sulfonyl]amino}-3-methylbutyramide;

N-hydroxy-2-(R)-{[4-(2-phenylbenzoxazol-5-yl)piperazine-1-sulfonyl]amino}-3-methylbutyramide;

N-hydroxy-2-(R)-{[4-(4-phenylimidazol-2-yl)piperidine-1-sulfonyl]amino}-3-methylbutyramide;

N-hydroxy-1-[4-phenoxypiperidine-1-sulfonyl]piperidine-2-(RS)-carboxamide;

N-hydroxy-2-(RS)-{methyl-[4-(5-chloropyridin-2-yl)piperazine-1-sulfonyl]amino}-4-phenylbutyramide;

N-hydroxy-2-(R)-{3-(pyridin-3-yl)propyl-[4-(4-bromophenyl)piperidine-1-sulfonyl]amino}-3-methylbutyramide; and N-hydroxy-2-(R)-{(pyridin-3-ylmethyl)-[4-(4-bromophenyl)piperidine-1-sulfonyl]amino}-3-methylbutyramide.

2. Proceeding as described in Example 11, Step 1 above, but substituting methyl (R)-2-{[4-(5-chloropyridin-2-yloxy)piperidine-1sulfonyl]amino}-3-methylbutyrate with methyl 1-[4-(pyridin-4-ylthio)piperidine-1-sulfonyl]piperidine-2-(R)-carboxylate [prepared as described in Example 3 above] gave 1-[4-(pyridin-4-ylthio)piperidine-1-sulfonyl]piperidine-2-(R)-carboxylic acid.

Example 12

Synthesis of N-hydroxy-1-[4-(4-chlorophenyl)piperazine-1-sulfonyl]piperidine-2-(RS)-carboxamide

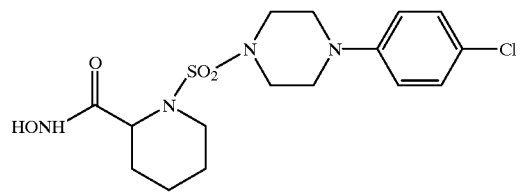

Step 1

A solution of methyl 1-[4-(4-chlorophenyl)piperazine-1-sulfonyl]piperidine-2-(RS)-carboxylate (164 mg, 0.41 mmol), [prepared as described in Example 3] and NaOH (33 mg, 0.82 mmol) in methanol/water (5 ml of 9:1 ratio) was heated at reflux. After 2 h, the reaction mixture was concentrated in vacuo, diluted with water (5 ml) and extracted with diethyl ether. The aqueous phase was acidified to pH 3 with 5% potassium bisulfate solution and the product was extracted into ethyl acetate. The organic phase was washed with brine, dried over MgSO$_4$, and concentrated to yield 1-[4-(4-chlorophenyl)piperazine-1-sulfonyl]piperidine-2-(RS)-carboxylic acid as a foam (125 mg, 79%).

Step 2

O-(tert-butyldimethylsilyl)hydroxylamine (57 mg, 0.39 mmol) and 1-(3-dimethylaminopropyl)-3-ethylcarbodiimide hydrochloride (59 mg, 0.31 mmol) were added to a solution of 1-[4-(4-chlorophenyl)piperazine-1-sulfonyl]piperidine-2-(RS)-carboxylic acid (100 mg, 0.26 mmol), [prepared as described above] in methylene chloride (4 ml). The reaction mixture was stirred overnight at RT and then diluted with methylene chloride. The solution was washed with water, 10% citric acid, and brine, and dried over MgSO$_4$. After the organics were removed the residue was chromatographed (SiO$_2$, 20–30% ethyl acetate/hexane) to give N-tert-butyldimethylsiloxy-1-[4-(4-chlorophenyl)piperazine-1-sulfonyl]piperidine-2-(RS)-carboxamide as a colorless foam (56%).

Step 3

Trifluoroacetic acid (few drops) was added to a solution of N-tert-butyldimethylsiloxy-1-[4-(4-chlorophenyl)piperazine-1-sulfonyl]pipeidine-2-(RS)-carboxamide (63 mg, 0.12 mmol), [prepared as described in Step 2 above], in methylene chloride (2 ml) and the reaction mixture was stirred at RT for 45 min. The organics were removed in vacuo and the residue was dissolved in methylene chloride (25 ml) and the washed with sat. sodium bicarbonate, brine, and dried over MgSO$_4$. The solvent was removed in vacuo to give a foam which was redissolved in a minimum amount of methylene chloride. Diethyl ether was added and the resulting white precipitates were filtered to give N-hydroxy-1-[4-(4-chlorophenyl)-piperazine-1-sulfonyl]-piperidine-2-(RS)-carboxamide (67%).

1. Proceeding as described in Example 12 above, but substituting methyl 1-[4-(4-chlorophenyl)piperazine-1-sulfonyl]piperidine-2-(RS)-carboxylate with methyl 1-[4-phenylthiopiperidine-1-sulfonyl]piperidine-2-(RS)-carboxylate [prepared as described in Example 3 above] gave N-hydroxy-1-[4-phenylthiopiperidine-1-sulfonyl]piperidine-2-(RS)-carboxamide.
2. Proceeding as described in Example 12, Steps 2 and 3 above, but substituting 1-[4-(4-chlorophenyl)piperazine-1-sulfonyl]piperidine-2-(RS)-carboxylic acid with 1-[4-(pyridin-4-ylthio)piperidine-1-sulfonyl]piperidine-2-(R)-carboxylic acid [prepared as described in Example 11 above) gave N-hydroxy-1-[4-(pyridin-4-ylthio)piperidine-1-sulfonyl]piperidine-2-(R)-carboxamide.

Example 13
Synthesis of N-hydroxy-2-(R)-{benzyl-[4-(4-chlorophenyl)piperazine-1-sulfonyl]amino}propionamide

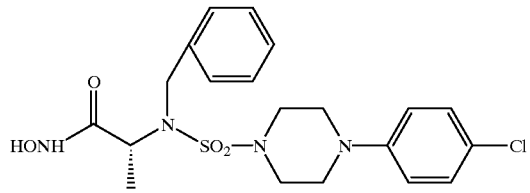

A solution of potassium hydroxide (1.6 g, 29.2 mmol) in methanol (9.8 ml) was added to a solution of hydroxylamine hydrochloride (1.02 g, 14.6 mmol) in methanol (9.8 ml) at 0° C. After 5 min., a solution of methyl 2-(R)-{benzyl-[4-(4-chlorophenyl)piperazine-1-sulfonyl]amino}-propionate (1.101 g, 2.44 mmol) in methanol (9.8 ml), [prepared as described in Example 2, Step, 2, but replacing D-valinesulfamoyl chloride methyl ester and 4-(5-chloropyridin-2-yloxy)piperidine with D-alaninesulfamoyl chloride methyl ester and 4-(4-chlorophenyl)piperazine respectively, followed by benzylation as described in Example 4] was added and the reaction temperature was allowed to rise to RT. After 5 h, the reaction mixture was diluted with methylene chloride (147 ml) and neutralized with 10% aqueous HCl. The solvent was removed in vacuo and the residue was dissolved in methanol. The insoluble salts were filtered off and N-hydroxy-2-(R)-{benzyl-[4-(4-chlorophenyl)piperazine-1-sulfonyl]amino}-propionamide was isolated using reverse phase preparative HPLC (20–70% acetonitrile/0.1% aqueous trifluoroacetic acid) as a crystalline solid (23%).

Proceeding as described in Example 13 above, but substituting methyl 2-(R)-{benzyl[4-(4-chlorophenyl)piperazine-1-sulfonyl]amino}propionate with methyl 2-(R)-{[4-[(4-chlorobenzylaminocarbonyl)methyl]piperidine-1-sulfonyl]amino}propionate [prepared as described in Example 2, above] gave N-hydroxy-2-(R)-{[4-[(4-chlorobenzylaminocarbonyl)methyl]-piperidine-1-sulfonyl]amino}propionamide.

Example 14
Synthesis of N-hydroxy-4-benzyloxycarbonyl-1-[4-(5-fluoroindol-3-yl)piperidine-1-sulfonyl]piperazine-2-(RS)-carboxamide

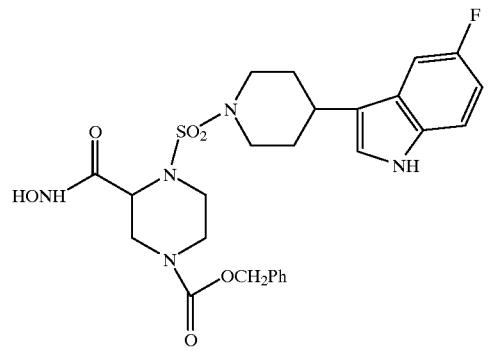

Step 1

To a solution of 4-(5-fluoroindol-3-yl)-1,2,3,6-tetrahydropyridine (3.68 g, 17.0 mmol) [prepared as described in Guillaume, J., Dumont, C., Laurent, J., Nedelec, L., *Eur. J. Med. Chem.*, 22, 33, (1987)] in argon deoxygenated methanol (80 ml) was added 10% Pd-C (740 mg) and the resulting mixture was stirred under an atmosphere of hydrogen (1 atm.). After 3 h, the reaction mixture was degassed under argon, di-tert-butyl dicarbonate (5.03 g, 23.0 mmol) was added, and the hydrogenation was continued for an additional 21 h. The argon degassed slurry was filtered through Celite, washed with methylene chloride, and the filtrate was concentrated in vacuo. Recrystallization of the residue from methylene chloride/hexanes gave N-tert-butoxycarbonyl-4-(5-fluoroindol-3-yl)piperidine (65%)as a white solid. The mother liquor (2 g) was chromatographed (SiO$_2$, 15% ethyl acetate/hexanes) to give an additional 0.9 g of product (12%).

Step 2

Sodium hydride (96 mg, 4.07 mmol) was added to a solution of N-tert-butoxycarbonyl-4-(5-fluoroindol-3-yl)piperidine (1.28 g, 4.07 mmol), [prepared as described in Step 1, above] in DMF (6 ml) at 0° C. and the reaction mixture was stirred for 30 min. 2-Trimethylsilylethanesulfonyl chloride (820 mg, 4.07 mmol) was added and the reaction mixture was slowly warmed to RT over 30 min. After 2.5 h, the reaction mixture was quenched with water (10 ml) and the product was extracted into methylene chloride. The combined organic layers were dried over MgSO$_4$ and concentrated in vacuo. Due to incomplete reaction the above steps were repeated on the isolated crude reaction mixture. The final residue was chromatographed (PTLC, SiO$_2$, 20% ethyl acetate/hexanes) to afford N-tert-butoxycarbonyl-4-[5-fluoro-1-(2-trimethylsilylethanesulfonyl)indol-3-yl]piperidine (84%) as a clear oil.

Step 3

To a solution of N-tert-butoxycarbonyl-4-[5-fluoro-1-(2-trimethylsilylethanesulfonyl)indol-3-yl]piperidine (1.33 g, 2.73 mmol), [prepared as described in Step 2, above] in methylene chloride (3 ml), was added trifluoroacetic acid (4 ml). After 2 h, the reaction mixture was concentrated in vacuo and the residue was partitioned between methylene chloride (50 ml) and of 1M NaOH (10 ml). The organic layers were dried over MgSO$_4$ and concentrated in vacuo to afford 4-[5-fluoro-1-(2-trimethylsilylethanesulfonyl)indol-3-yl]piperidine (100%). This material was used in the next step without further purification.

Step 4

To a solution of 4-[5-fluoro-1-(2-trimethylsilylethanesulfonyl)indol-3-yl]piperidine (1.05 g, 2.73 mmol), [prepared as described in Step 3, above] and triethylamine (0.837 ml, 6.01 mmol) in methylene chloride (14.4 ml) at 0° C., was added chlorosulfonic acid (0.191 ml, 2.87 mmol) over 5 min. The reaction mixture was stirred overnight at RT and then concentrated in vacuo. The residue was diluted with benzene (14.4 ml), phosphorous pentachloride (568 mg, 2.73 mmol) was added and the resulting mixture was heated at reflux for 2 h. The heterogeneous reaction mixture was cooled to RT and filtered through a plug of silica gel (20 g) using 30% ethyl acetate/hexanes (250 ml). The eluent was washed with 2.4 N aqueous HCl, dried over MgSO$_4$, and concentrated in vacuo to afford 4-[5-fluoro-1-(2trimethylsilylethane-sulfonyl)-3-yl] piperidinesulfamoyl chloride (83%) as a pale yellow foam.

Step 5

To a solution of piperazic acid ammonium salt (7.5 g, 57 mmol) and triethylamine (17 ml, 122 mmol) in of water (22 ml) at 0° C., was added a solution of O-carbobenzyloxysuccinimide (14.4 g, 57.8 mmol) in dioxane (22 ml) over a 1.25 h period. The reaction mixture was allowed to warm to RT over 2 h and the stirring was continued. After 20 h, the reaction mixture was concentrated in vacuo and the residue was triturated with warm ethanol, filtered, and washed with ether to afford 4-benzyloxycarbonylpiperazine-2-(RS)-carboxylic acid ammonium salt (63%) as a light tan solid. This material was used without further purification.

Step 6

To a slurry of 4-benzyloxycarbonylpiperazine-2-(RS)-carboxylic acid ammonium salt (503 mg, 1.90 mmol), [prepared as described in Step 5 above]in acetonitrile (3 ml) at 0° C., was added trimethylsilylcyanide (0.476 ml, 3.80 mmol) and the reaction mixture warmed to RT over 10 min. 4-[5-Fluoro-1-(2-trimethylsilylethanesulfonyl)indol-3-yl] piperidinesulfamoyl chloride (300 mg, 0.62 mmol) [prepared as described in Step 4 above] was added in one portion, and the mixture was heated at reflux for 14 h. The solution was cooled to RT, methanol (2 ml) was added, and the resulting heterogeneous mixture was stirred for 10 min. The slurry was filtered through a plug of silica gel (20 g) using 10% methylene chloride-hexanes (250 ml), the filtrate was concentrated, and the residue was chromatographed (PTLC, SiO$_2$, 10% methanol/methylene chloride) to afford 4-benzyloxycarbonyl-1-{4-[5-fluoro-1-(2-trimethylsilylethanesulfonyl)indol-3-yl]piperidine-1-sulfonyl}piperazine-2-(RS)-carboxylic acid (63%) as a yellow foam.

Step 7

To a solution of 4-benzyloxycarbonyl-1-{4-[5-fluoro-1-(2-trimethylsilylethanesulfonyl)indol-3-yl]piperidine-1-sulfonyl}piperazine-2-(RS)-carboxylic acid (288 mg, 0.40 mmol), [prepared as described in Step 6 above] in methylene chloride (5 ml) at 0° C. were added a few drops of DMF and oxalyl chloride (89 ml, 1.0 mmol). The reaction mixture was warmed to RT over 1 h, and stirring was continued for an additional 14 h. The reaction mixture was concentrated in vacuo, redissolved in methylene chloride (5 ml) and cooled to 0° C. N,O-bis-trimethylsilyl hydroxylamine (0.304 ml, 1.42 mmol) added, the reaction was warmed to RT, stirred for 3 h, and then recooled to 0° C. After adding methanol (3 ml), the mixture was stirred for an additional 30 min., and then concentrated in vacuo. The residue was partitioned between methylene chloride (50 ml) and aqueous 2.4 M HCl (10 ml), the organic layer was separated and washed with saturated aqueous sodium bicarbonate, dried over MgSO$_4$, and concentrated in vacuo to afford N-hydroxy-4-benzyloxycarbonyl-1-{4-[5-fluoro-1-(2-trimethylsilylethanesulfonyl)-indol-3-yl]-piperidine-1-sulfonyl}piperazine-2-(RS)-carboxamide as a yellow foam (250 mg, 86%). The residue was used without further purification.

Step 8

Tetrabutylammonium fluoride (0.194 ml, 1M solution in tetrahydrofuran) was added to a solution of N-hydroxy-4-benzyloxycarbonyl-1-{4-[5-fluoro-1-(2-trimethylsilylethanesulfonyl)-indol-3-yl]-piperidine-1-sulfonyl}piperazine-2-(RS)-carboxamide (0.067 mg, 0.093 mmol), [prepared as described in Step 7 above] in tetrahydrofuran (1.6 ml). The reaction mixture was heated at 45° C. for approx. 20 min., and then quenched with glacial acetic acid (0.011 ml, 0.194 mmol). The reaction mixture was concentrated and the residue was chromatographed by preparatory TLC (10% methanol/methylene chloride) to give N-hydroxy-4-benzyloxycarbonyl-1-{4-[5-fluoroindol-3-yl] piperidine-1-sulfonyl}piperazine-2-(RS)-carboxamide (71%), mp 85.7–89.7° C.

Example 15

Synthesis of N-hydroxy-4-(N,N-dimethylaminocarbonyl)-1-[4-(4,5,6,7-tetrafluoroindol-3-yl)piperidine-1-sulfonyl] piperazine-2-(R)-carboxamide

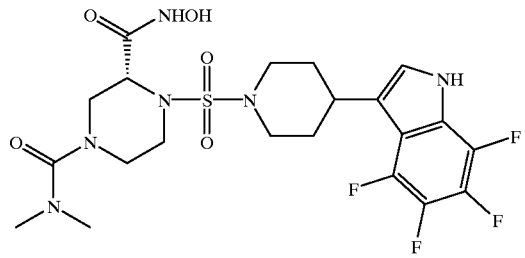

Step 1

To a solution of N-benzyloxycarbonyl-4-piperidone (20.2 g, 90.6 mmol) in methylene chloride (600 ml) at 0° C. was added trimethylsilyl trifluoromethanesulfonate (35.1 ml, 181.2 mmol) followed by the slow dropwise addition of a solution of 4,5,6,7-tetrafluoroindole (17.1 g, 90.6 mmol) in methylene chloride (300 ml) over 2.5 h. After 1.5 h, triethylsilane (57.9 ml, 362.4 mmol) was added and the reaction was allowed to warm to RT over 30 min. The reaction mixture was quenched with sat. sodium bicarbonate and the separated organic layer was dried over MgSO$_4$ and concentrated in vacuo. The residue was partitioned between 50% acetonitrile/hexanes (1400 ml) and the separated acetonitrile layer was concentrated in vacuo. The solid residue was recrystallized from absolute EtOH to afford N-benzyloxycarbonyl-4-(4,5,6,7-tetrafluoroindol-3-yl) piperidine (66%) as a white solid.

Step 2

To a solution of N-benzyloxycarbonyl-4-(4,5,6,7-tetrafluoroindol-3-yl)piperidine (20.0 g, 49.21 mmol) [prepared as described in Step 1 above] in argon deoxygenated 80% ethanol/tetrahydrofuran (800 ml) was added 10%

Pd-C (5 g), and the resulting mixture was stirred under a hydrogen atmosphere (1 atm) for 3 h. The mixture was degassed under argon, filtered through Celite, and concentrated in vacuo. The solid residue was recrystallized from methylene chloride/hexane to afford 4-(4,5,6,7-tetrafluoroindol-3-yl)piperidine (90%) as a white solid.

Step 3

Chlorosulfonic acid (2.9 ml, 44.10 mmol) was added dropwise over 5 min., to a solution of 4-(4,5.6,7-tetrafluoroindol-3-yl)piperidine (12.0 g, 44.10 mmol) [prepared as described in Step 2 above] and triethylamine (12.9 ml, 92.61 mmol) in methylene chloride (220 ml) at 0° C. The reaction was allowed to warm to RT overnight with stirring and then concentrated in vacuo. The residue was diluted with benzene (220 ml), phosphorous pentachloride (9.74 g, 46.78 mmol) was added and the resulting mixture was heated to reflux for 2 h. The heterogeneous reaction mixture was cooled to RT and filtered through a pad of silica gel using 30% ethyl acetate-hexanes as the eluant. The resulting filtrate was washed with 2.4 M aqueous hydrochloric acid, dried over $MgSO_4$ and concentrated in vacuo to give 4-(4,5,6,7-tetrafluoro-indol-3-yl)piperidinesulfamoyl chloride (99%) as an orange oil.

Step 4

To a slurry of 4-(N)-tert-butoxycarbonylpiperazine-2-(R)-carboxylic acid (34 g, 148 mmol) [prepared as described in Bigge, C. F.; Hays, S. J.; Novak, P. M.; Drummond, J. T.; Johnson, G.; Bobovski, T. P. *Tet. Lett.* 5193, (1989)] in acetonitrile (500 ml) was added trimethylsilylcyanide (47.7 ml, 381 mmol) at 0° C. The reaction mixture warmed to RT over 50 min., and 4-(4,5,6,7-tetrafluoroindol-3-yl) piperidinesulfamoyl chloride (16.38 g, 44.1 mmol) [prepared as described in Step 3 above] was added in one portion. The reaction mixture was heated at reflux for 36 h and then cooled to RT. Methanol (10 ml) was added, and the resulting heterogeneous mixture was stirred for 10 min. The slurry was filtered through a pad of silica gel using 10% methylene chloride/hexanes as the eluant. The filtrate was concentrated in vacuo and the residue was chromatographed ($SiO_2$, 10% methanol/methylene chloride) to afford 25.0 g of 4-tert-butoxycarbonyl-1-[4-(4,5,6,7-tetrafluoroindol-3-yl)-piperidine-1-sulfonyl]piperazine-2-(R)-carboxylic acid which was immediately dissolved in methylene chloride (400 ml) and cooled to 0° C. To this solution was added O-benzylhydroxylamine (15.92 g, 129.5 mmol), 4-dimethylaminopyridine (5.27 g, 43.15 mmol) and 4-methylmorpholine (14.2 ml, 129.5 mmol), followed by the slow addition of 1-ethyl-3-(3-dimethylaminopropyl) carbodiimide (17.37 g, 90.62 mmol) over 15 min. The reaction mixture was allowed to warm to RT overnight and 2 M aqueous HCl solution was added. The separated methylene chloride layer was dried over $MgSO_4$, and concentrated in vacuo. The residue was chronmatographed ($SiO_2$, 1% methanol/methylene chloride) to afford N-benzyloxy4-tert-butoxycarbonyl-1-[4-(4,5,6,7-tetrafluoroindol-3-yl) piperidine-1-sulfonyl]piperazine-2-(R)-carboxamide (78%) as a yellow foam.

Step 5

To a solution of N-benzyloxy-4-tert-butoxycarbonyl-1-[4-(4,5,6,7-tetrafluoroindol-3-yl)piperidine-1-sulfonyl] piperazine-2-(R)-carboxamide (24.40 g, 36.40 mmol) [prepared as described in Step 4 above] in methylene chloride (90 ml) was added trifluoroacetic acid (60 ml). The reaction mixture was stirred for 2 h, concentrated in vacuo, and partitioned between ethyl acetate (500 ml) and sat. sodium bicarbonate (200 ml). The aqueous layer was washed with ethyl acetate and the combined organic layers were dried over $MgSO_4$ and concentrated in vacuo. The residue was dissolved in ethyl acetate (40 ml) and slowly added to hexane (200 ml) with vigorous stirring. The resulting slurry was filtered to afford 20.65 g of N-benzyloxy-1-[4-(4,5,6,7-tetrafluoroindol-3-yl)piperidine-1-sulfonyl] piperazine-2-(R)-carboxamide as a white solid.

Step 6

A solution of N-benzyloxy-1-[4-(4,5,6,7-tetrafluoroindol-3-yl)piperidine-1-sulfonyl]piperazine-2-(R)-carboxamide (12 g, 21.08 mmol) [prepared as described in Step 5 above] and 2,6-luitidine (4.0 ml, 33.73 mmol) in methylene chloride (100 ml) was treated with dimethylcarbamoyl chloride (3.10 ml, 33.73 mmol) and stirred for 14 h. The reaction mixture was washed with 3M aqueous HCl solution (20 ml), brine, dried over $MgSO_4$ and concentrated in vacuo. The residue was chromatographed ($SiO_2$, 30% ethyl acetate/hexane then 5% methanol/methylene chloride). The product was dissolved in ethyl acetate (25 ml) and added dropwise to hexane (200 ml) with vigorous stirring. The solid was filtered to give N-benzyloxy-4-(N,N-dimethylaminocarbonyl)-1-[4-(4,5,6,7-tetrafluoroindol-3-yl)piperidine-1sulfonyl]piperazine-2-(R)-carboxamide (67%) as a white solid.

Step 7

A solution of N-benzyloxy-4-(N,N-dimethylaminocarbonyl)-1-[4-(4,5,6,7-tetrafluoroindol-3-yl)piperidine-1-sulfonyl]piperazine-2-(R)-carboxamide (8.90 g, 13.97 mmol) [prepared as described in Step 6 above] in argon deoxygenated 80% ethanol/tetrahydrofuran (470 ml) was treated with 10% Pd/C (3.5 g) and stirred under a hydrogen atmosphere (1 atm) for 45 min. The reaction was degassed under argon, filtered through Celite, and the filtrate was concentrated in vacuo. Ethyl acetate (5 ml) was added and the solution was added dropwise to hexane (250 ml) with vigorous stirring. The solid was filtered to afford N-hydroxy-4-(N,N-dimethylaminocarbonyl)-1-[4-(4,5,6,7-tetrafluoroindol-3-yl)piperidine-1-sulfonyl]piperazine-2-(R)-carboxamide (96%) as a white solid.

1. Proceeding as described in Example 15, Step 5, but substituting N-benzyloxy-4-tert-butoxycarbonyl-1-[4-(4,5,6,7-tetrafluoroindol-3-yl)piperidine-1-sulfonyl] piperazine-2-(R)-carboxamide with N-tert-butoxy-1-tert-butoxycarbonyl-4-{[4-(4-chlorobenzoyl)piperidine-1-sulfonyl]amino}piperidine-4-carboxamide [prepared as described in Example 10, above] gave N-tert-butoxy-4-{[4-(4-chlorobenzoyl)piperidine-1-sulfonyl] amino}piperidine-4-carboxamide.

2. Proceeding as described in Example 15, Step 4, but substituting O-benzylhydroxylamine and 4-(4,5,6,7-tetrafluoroindol-3-yl)piperidine sulfamoyl chloride with O-tert-butylhydroxylamine and 4-(4-chlorobenzoyl) piperidinesulfamoyl chloride respectively, gave N-tert-butoxy-4-tert-butoxycarbonyl-1-[4-(4-chlorobenzoyl) piperidine-1-sulfonyl]piperazine-2-(R)-carboxamide. This material was converted to N-tert-butoxy-1-[4-(4-chlorobenzoyl)piperidine-1-sulfonyl]piperazine-2-(R)-carboxamide by carrying out the hydrolysis with 15–20% trifluoroacetic acid in methylene chloride and closely monitoring the reaction by TLC.

Example 16

Synthesis of N-hydroxy-N-methyl-1-[4-(5-fluoroindol-3-yl)piperidine-1-sulfonyl]piperidine-2-(R)-carboxamide

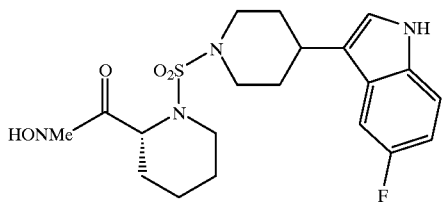

Step 1

Chlorosulfonic acid (14.25 ml, 214.5 mmol) was added dropwise to a 0° C. solution of 2-(R)-methoxycarbonylpiperidine HCl salt (35.0 g, 195 mmol) and triethylamine (86.96 ml, 624 mmol) in methylene chloride (550 ml). The reaction was stirred for 5 h, concentrated in vacuo, and dried under high vacuum overnight. The resulting yellow solid was suspended in benzene (500 ml) and phosphorus pentachloride (40.6 g, 195 mmol) was added. The reaction mixture was heated at reflux with vigorous stirring for 5 h and concentrated in vacuo. The resulting slurry was stirred with ether (300 ml) and filtered. The solid was washed with additional ether (300 ml) and the combined filtrate was washed with water, brine, dried over $MgSO_4$, and concentrated to give 2-(R)-methoxycarbonylpiperidine-1-sulfamoyl chloride (88%) as a dark yellow oil that was used without further purification.

Step 2

A solution of 4-(5-fluoroindol-3-yl)piperidine (0.40 g, 1.83 mmol) and triethylamine (1.02 ml, 7.33 mmol) in tetrahydrofuran (13 ml) was treated with 2-(R)-methoxycarbonylpiperidine-1-sulfamoyl chloride (0.66 g, 2.75 mmol) [prepared as described above in Step 1] and the reaction mixture was stirred at RT for 24 h. The reaction was quenched with sat. ammonium chloride solution and extracted with ethyl acetate. The organic layer was washed with brine, dried over $MgSO_4$, and concentrated. The residue was chromatographed (PTLC, $SiO_2$, 20%–35% ethyl acetate/hexanes) to give methyl 1-[4-(5-fluoroindol-3-yl)piperidine-1-sulfonyl]piperidine-2-(R)-carboxylate (61%) as a clear oil. This material was converted to 1-[4-(5-fluoroindol-3-yl)piperidine-1-sulfonyl]piperidine-2-(R)-carboxylic acid by proceeding as described in Example 11, Step 1 but substituting methyl (R)-2-{[4-(5-chloropyridin-2-yloxy)piperidine-1-sulfonyl]amino}-3-methylbutyrate with methyl 1-[4-(5-fluoroindol-3-yl)piperidine-1-sulfonyl]piperidine-2-(R)-carboxylate.

Step 3

To a solution of 1-[4-(5-fluoroindol-3-yl)piperidine-1-sulfonyl]piperidine-2-(R)-carboxylic acid (0.46 g, 1.12 mmol) [prepared as described Step 2 above] in methylene chloride (10 ml) was added O-benzylhydroxylamine hydrochloride salt (0.54 g, 3.36 mmol), followed by 4-dimethylaminopyridine (0.15 g, 1.23 mmol), 4-methylmorpholine (0.38 ml, 3.47 mmol), and 1-ethyl-3-(3-dimethylaminopropyl)-carbodiimide (0.43 g, 2.24 mmol). The reaction was stirred at RT for 2 h, diluted with methylene chloride (50 ml) and washed with 1M HCl. The organic layer was washed with brine, dried over $MgSO_4$, and concentrated to give N-benzyloxy.-1-[4-(5-fluoroindol-3-yl)piperidine-1-sulfonyl]piperidine-2-(R)-carboxamide (95%) as a clear oil. This material was used without further purification.

Step 4

Anhydrous potassium carbonate (736 mg, 5.33 mmol) and iodomethane (0.133 ml, 2.13 mmol) were added to a solution of N-benzyloxy-1-[4-(5-fluoroindol-3-yl)piperidine-1-sulfonyl]piperidine-2-(R)-carboxamide (549 mg, 1.07 mmol) [prepared as described in Step 3 above] in dimethylformamide (11 ml) at RT. After 2 h, the reaction mixture was diluted with ethyl acetate (50 ml) and then washed with 0.1 M HCl, brine and dried over $MgSO_4$. The solvent was removed in vacuo and the residue was chromatographed (PTLC, $SiO_2$, 40% ethyl acetate/hexanes) to give N-benzyloxy-N-methyl-1-[4-(5-fluoroindol-3-yl)piperidine-1-sulfonyl]piperidine-2-(R)-carboxamide (71%) as a white solid.

Step 5

A suspension of 10% Pd/C (0.20 g) and N-benzyloxy-N-methyl-1-[4-(5-fluoroindol-3-yl)piperidine-1-sulfonyl]piperdine-2-(R)-carboxamide (0.40 g, 0.75 mmol) [prepared as described in Step 4 above] in 80% ethanol/tetrahydrofuran (6 ml) was stirred under a hydrogen atmosphere (1 atm) for 70 min. The reaction was degassed with nitrogen, filtered through Celite and the filtrate was concentrated in vacuo. The residue was chromatographed (PTLC, $SiO_2$, 10% methanol/methylene chloride) to give N-hydroxy-N-methyl-1-[4-(5-fluoroindol-3-yl)piperidine-1-sulfonyl]piperidine-2-(R)-carboxamide (83%) as a white solid.

1. Proceeding as described in Example 16, Step 2 but substituting 2-(R)-methoxycarbonylpiperidine-1-sulfamoyl chloride and 4-(5-fluoroindol-3-yl)piperidine with 2-(RS)-ethoxycarbonylpiperidine-1-sulfamoyl chloride and 4-(6-fluorobenzisoxazol-3-yl)piperidine ((prepared as described in Strupczewski, J. T., Allen, R. C., Gardner, B. A., Schmid, B. L., Stache, U., Glamkowski, E. J., Jones, M. C., Ellis, D. B., Huger, F. P., Dunn, R. W., *J. Med. Chem.*, 28, 761, (1985)) respectively, gave ethyl 1-[4-(6-fluorobenzisoxazol-3-yl)piperidine-1-sulfonyl]piperidine-2-(RS)-1-carboxylate. This material was converted to N-hydroxy-1-[4-(6-fluorobenzisoxazol-3-yl)piperidine-1-sulfonyl]piperidine-2-(RS)-carboxamide by following procedure described in Example 11.

2. Proceeding as described in Example 16, Step 2 but substituting 4-(5-fluoroindol-3-yl)piperidine with 1,2,3,4-tetrahydro-beta-carboline gave methyl 1-[1,2,3,4-tetrahydro-beta-carboline-2-sulfonyl]piperidine-2-(R)-carboxylate which was converted to N-hydroxy-1-[1,2,3,4-tetrahydro-beta-carboline-2-sulfonyl]piperidine-2-(R)-carboxamide by following Example 16, Steps 3 and 5 above.

3. Proceeding as described in Example 16, Step 3 above, but substituting of 1-[4-(5-fluoroindol-3-yl)piperidine-1-sulfonyl]piperidine-2-(R)-carboxylic acid with 5-(biphenyl-4-ylmethyl)-1,1-dioxo-1,2,5-thiadiazolidine-2-acetate [prepared as described in Example 8 above] gave N-benzyloxy-5-(biphenyl-4-ylmethyl)-1,1-dioxo-1,2,5-thiadiazolidine-2-acetamide which was converted to N-hydroxy-5-(biphenyl-4-ylmethyl)-1,1-dioxo-1,2,5-thiadiazolidine-2-acetamide by following Example 16, Step 5.

Example 17
Synthesis of N-hydroxy-1-[4-(5-hydroxyindol-3-yl) piperidine-1-sulfonylpiperidine-2-(RS)-carboxamide

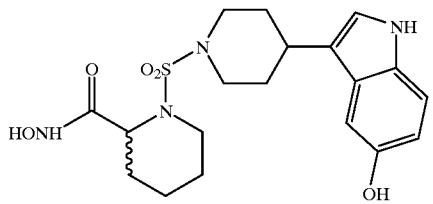

Step 1

Potassium tert-butoxide (2.81 g, 25.02 mmol) was added to a solution of 5-hydroxyindole (1.11 g, 8.34 mmol) in tert-butyl alcohol. 1-Benzyloxycarbonyl-4-piperidone (3.89 g, 16.67 mmol) was added to the purple reaction mixture at RT. After 16 h, the reaction mixture was diluted with ethyl acetate (100 ml) and washed with saturated sodium bicarbonate, brine, dried over MgSO$_4$ and concentrated in vacuo. The residue was chromatographed (SiO$_2$, 25–45% ethyl acetate/hexanes) to give 4-(5-hydroxyindol-3-yl)-1,2, 3,6-tetrahydropyridine as a white solid (92%).

Step 2

Tetrahydrofuran (96 ml) was added to an argon degassed flask containing 4-(5-hydroxyindol-3-yl)-1,2,3,6-tetrahydropyridine (2.67 g, 7.64 mmol), [prepared as described in Step 1, above] and 10% Palladium on carbon (2.67 g). The reaction mixture was hydrogenated for 15 h at 60 psi on a parr apparatus. The reaction mixture was degassed, filtered through Celite and concentrated in vacuo to give 4-(5-hydroxyindol-3-yl)piperidine as a white solid (95%). This material was converted to 1-[4-(5-hydroxyindol-3-yl)piperidine-1-sulfonyl]piperidine-2-(RS)-carboxylic acid (99%) by proceeding as described in Example 16, Step 2 above, by substituting 4-(5-fluoroindol-3-yl)piperidine and 2-(R)-methoxycarbonylpiperidine-1-sulfamoyl chloride with 4-(5-hydroxyindol-3-yl)piperidine and 2-(RS)-methoxycarbonylpiperidine-1-sulfamoyl chloride respectively.

Step 3

N-Hydroxysuccinimide (0.181 g, 1.57 mmol), 4-dimethylaminopyridine (96 mg, 0.78 mmol) and 1-(3-dimethylaminopropyl)-3-ethylcarbodiimide hydrochloride (0.33 g, 1.73 mmol) were added to a solution of 1-[4-(5-hydroxyindol-3-yl)piperidine-1-sulfonyl]piperidine-2-(RS)-carboxylic acid (0.32 g, 0.78 mmol) (prepared as described in Step 2 above] in 30% dimethylformamide/methylene chloride (5.5 ml). After stirring at RT for 2 h, the reaction was diluted with methylene chloride (50 ml) and washed with 1M HCl, brine and dried over MgSO$_4$. The organics were evaporated in vacuo and the residue was dissolved in 50% ethyl acetate/methanol (13.4 ml). This solution was added to a solution of 50% aqueous hydroxylamine (6.7 ml, 109 mmol) in methanol (6.7 ml) at –30° C. with vigorous stirring. After 10 min., the reaction mixture was quenched with 1M HCl (final pH=3) and then concentrated in vacuo. The residue was extracted with ethyl acetate and the organic layer was washed with brine and dried over MgSO$_4$. The organics were evaporated in vacuo and the residue was chromatographed (SiO$_2$, 10% methanol/methylene chloride) to give N-hydroxy-1-[4-(5-hydroxyindol-3-yl)piperdine-1-sulfonyl]piperidine-2-(RS)-carboxamide (22%) as a white solid.

Proceeding as described in Example 17, Step 3, but substituting 30% dimethylformamide/methylene chloride with 100% methylene chloride and 1-[4-(5-hydroxyindol-3-yl)-piperidine-1-sulfonyl]piperidine-2-(RS)-carboxylic acid with 6-(benzyloxycarbonyl)amino-2-(R){[4-(4-chlorophenyl)piperazine-1-sulfonyl]amino}hexanoic acid [prepared as described in Example 9 above] gave N-hydroxy-6-(benzyloxycarbonyl)-amino-2-(R)-{[4-(4-chlorophenyl)piperazine-1-sulfonyl]amino}hexanoamide.

Example 18
Synthesis of N-hydroxy-1-[4-(pyrrol-3-yl)piperidine-1-sulfonyl]piperidine-2-(R)-carboxamide

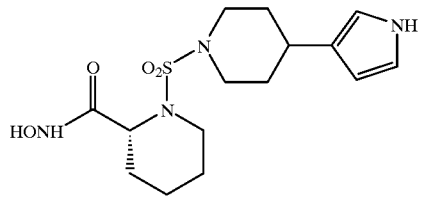

Step 1

To a solution of N-tert-butoxycarbonyl-4-piperidone (7.77 g, 39 mmol) in methylene chloride (200 ml) at 0° C. was added trifluoroacetic acid (70 ml) and the resulting solution was allowed to warm to RT over 1.5 h. The reaction mixture was concentrated in vacuo, dried under high vacuum for 3 h and 25% water/dioxane (70 ml) was added. To this solution was added sodium carbonate (8.3 g, 78 mmol) and 2-(R)-methoxycarbonylpiperidine-1-sulfamoyl chloride (3.5 g, 15.6 mmol) and the resulting suspension was rapidly stirred at RT. After 24 h, the reaction mixture was filtered and the filtrate was diluted with ethyl acetate (150 ml), water (200 ml) and acidified with 1 M HCl. The aqueous layer was extracted with ethyl acetate and the combined organics were washed with brine, dried over MgSO$_4$ and concentrated to give methyl 1-(4-piperidone-1-sulfonyl)piperidine-2-(R)-carboxylate (96%) as a pale yellow oil that was used without further purification.

Step 2

A solution of N-triisopropylsilylpyrrole (1.62 ml, 6.57 mmol) in methylene chloride (50 ml) was added to a solution of methyl 1-(4-piperidone-1-sulfonyl)piperidine-2-(R)-carboxylate [prepared as described in Step 1 above] and trimethylsilyl trifluoromethanesulfonate (2.54 ml, 13.14 mmol) in methylene chloride (110 ml) at –78° C. over 1.5 h. Triethylsilane (4.2 ml, 26.28 mmol) was added and after 2 h the reaction mixture was washed with saturated sodium bicarbonate, brine and dried over MgSO$_4$. The solvent was evaporated in vacuo, and the residue was chromatographed (SiO$_2$, 10–20% ethyl acetate/hexanes) to give methyl 1-[4-(1triisopropylsilylpyrrol-3-yl)-piperidine-1-sulfonyl) piperidine-2-(R)-carboxylate which was used in the next step without further purification.

Step 3

Tetrabutylammonium fluoride (2.45 ml, 2.45 mmol) was added to a solution of methyl 1-[4-(1-triisopropylsilylpyrrol-3-yl)piperidine-1-sulfonyl]piperidine-2-(R)-carboxylate (2.5 g, 4.89 mmol) [prepared as described in Step 2 above] in tetrahydrofuran (48 ml) at 0° C. After 30 min., the reaction mixture was diluted with ethyl acetate, washed with water, brine, dried over MgSO$_4$, and concentrated in vacuo. The residue was chromatographed (SiO$_2$, 15–40% ethyl acetate/hexanes) to yield methyl 1-[4-(pyrrol-3-yl)piperidine-1-sulfonyl]piperidine-2-(R)-carboxylate (31%) as a clear oil. This material was converted to 1-[4-(pyrrol-3-yl)piperidine-1-sulfonyl]piperidine-2-(R)-carboxylic acid (93%) by proceeding as described in Example 11, Step 1, but substituting methyl (R)-2-{[4-(5-chloropyridin-2-yloxy)piperidine-1-sulfonyl]amino}-3-methylbutyrate with methyl 1-[4-(pyrrol-3-yl)piperidine-1-sulfonyl]piperidine-2-(R)-carboxylate.

Step 4

Proceeding as described in Example 17, Step 4, but substituting 30% dimethylformamide/methylene chloride with 100% methylene chloride and 1-[4-(5-hydroxyindol-3-yl)piperidine-1-sulfonyl]piperidine-2-(RS)-carboxylic acid with 1-[4-(pyrrol-3-yl)piperidine-1-sulfonyl]piperidine-2-(R)-carboxylic acid [prepared as described in Step 3 above] gave N-hydroxy-1-[4-(pyrrol-3-yl)piperidine-1-sulfonyl]piperidine-2-(R)-carboxamide (21%) as a white solid.

Example 19
Synthesis of N-hydroxy-1-[4-(5-cyano-1-methanesulfonylindol-3-yl)piperidine-1-sulfonyl]piperidine-2-(R)-carboxamide

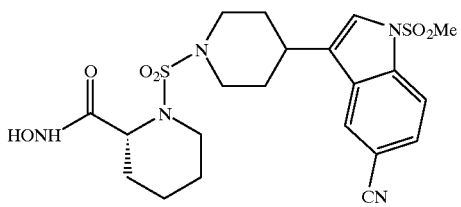

Step 1

A solution of 5-cyanoindole (10.00 g, 70.34 mmol) in acetonitrile (120 ml) was added to a solution of 1-benzyloxycarbonyl-4-piperidone (8.20g, 35.17 mmol) and trimethylsilyl trifluoromethanesulfonate (6.80 ml, 35.17 mmol) in acetonitrile (230 ml) via addition funnel at 0° C. over 1.5 h. Triethylsilane (4.2 ml, 26.28 mmol) was added at 0° C. and reaction mixture was allowed to gradually warm to RT over 2 h. The reaction mixture was diluted with ethyl acetate and washed with saturated sodium bicarbonate, brine, dried over MgSO$_4$, and concentrated in vacuo. The residue was diluted with acetonitrile (300 ml) and hexanes (200 ml) and stirred for 20 min. The organics were removed in vacuo and the residue was chromatographed (SiO$_2$, 20–40% ethyl acetate/hexanes) to give 1-benzyloxycarbonyl-4-(5-cyanoindol-3-yl)piperidine as a white crystalline solid (59%).

Step 2

Sodium hydride (115 mg, 4.8 mmol) was added to a solution of 1-benzyloxycarbonyl-4-(5-cyanoindol-3-yl)piperidine (1.5 g, 4.17 mmol) [prepared as described in Step 1 above] in dimethylformamide (12 ml) at 0° C. After 30 min., methanesulfonyl chloride (0.81 ml, 10.43 mmol) was added and after stirring for 2.5 h the reaction mixture was allowed to warm to RT over 1 h. The reaction mixture was diluted with ethyl acetate (100 ml) and washed with water, brine and dried over MgSO$_4$. The organics were evaporated in vacuo and the residue was chromatographed (PTLC, SiO$_2$, 40% ethyl acetate/hexanes) to give 1-benzyloxycarbonyl-4-(5-cyano-1-methanesulfonylindol-3-yl)piperidine (54%) as a pale yellow oil.

Step 3

10% Palladium on carbon (0.49 g) was added to a solution of 1-benzyloxycarbonyl-4-(5-cyano-1-methanesulfonylindol-3-yl)piperidine (0.98 g, 2.24 mmol) [prepared as described in Step 2 above] in 80% ethanol/tetrahydrofuran (10 ml) under an argon atmosphere. The reaction mixture was stirred under an atmosphere of hydrogen gas (1 atm) for 2 h. The reaction mixture was degassed, filtered through Celite and concentrated in vacuo to give 4-(5-cyano-1-methanesulfonylindol-3-yl)piperidine (97%) as a white solid. This material was converted to N-hydroxy-1-[4-(5-cyano-1-methanesulfonylindol-3-yl)piperidine-1-sulfonyl]piperidine-2-(R)-carboxamide by converting it to 4-(5-cyano-1-methanesulfonylindol-3-yl)piperidine-1-sulfonyl chloride by following Example 16, Step 1, coupling the sulfonyl chloride with (R)-pipecolinic acid (L)-tartrate salt to give 1-[4-(5-cyano-1-methanesulfonylindol-3-yl)piperidine-1-sulfonyl]piperidine-2-(R)-carboxylic acid (86%) by following Example 14, Step 6 and then converting the acid to the final compound by following Example 16, Steps 3 and 5; mp: 143.3–143.9° C.

Proceeding as described in Example 19, Step 3, but substituting 1-benzyloxycarbonyl-4-(5-cyano-1-methanesulfonylindol-3-yl)piperidine with 1-benzyloxycarbonyl-4-[5-cyano-1-(2-trimethylsilylethanesulfonyl)indol-3-yl]piperidine [prepared as described in Example 14, Step 2, by substituting 1-benzyloxycarbonyl-4-(5-cyanoindol-3-yl)piperidine for N-tert-butoxycarbonyl-4-(5-fluoroindol-3-yl)piperidine] gave 4-[5-cyano-1-(2-trimethylsilylethanesulfonyl)indol-3-yl]piperidine.

Example 20
Synthesis of N-hydroxy-1-[4-(5-cyanoindol-3-yl)piperidine-1-sulfonyl]-4-(N,N-dimethylaminosulfonyl)piperizine-2-(R)-carboxamide

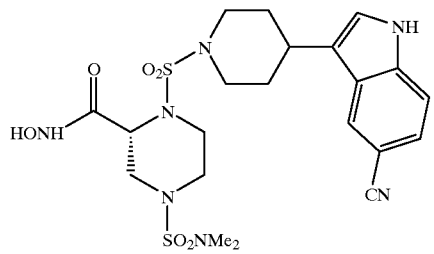

Step 1

N,N-Dimethylsulfamoyl chloride (0.14 ml, 1.31 mmol), sodium carbonate (0.46 g, 4.37 mmol) and water (3 ml) were added to a solution of N-benzyloxy-1-{4-[5-cyano-1-(2-trimethylsilylethanesulfonyl)indole-3-yl]piperidine-1-sulfonyl}-1,4-piperazine-2-(R)-carboxamide (0.6 g, 0.87 mmol) [prepared from 4-[5-cyano-1-(2-trimethylsilylethanesulfonyl)indol-3-yl]piperidine by following the procedures described in Example 19, Step 3, Example 14, step 4 and Example 15, Steps 4 and 5] in dioxane (6 ml) at RT. After 1 h, the reaction mixture was acidified with 1M HCl and concentrated in vacuo. The aqueous layer was diluted with ethyl acetate (75 ml) and water. The organics were washed with brine, dried over MgSO$_4$ and concentrated in vacuo. The residue was chromatographed (PTLC, SiO$_2$, 35% ethyl acetate/hexane) to give N-benzyloxy-1-{4-[5-cyano-1-(2-trimethylsilylethanesulfonyl)-indol-3-yl]piperidine-1-sulfonyl}-4-(N,N-dimethylarainosulfonyl)piperazine-2-(R)-carboxamide (71%) as a white solid.

Step 2

A solution of tetrabutylammonium fluoride in tetrahydrofuran (1.54 ml, 1.54 mmol) was added to a solution of N-benzyloxy-1-(4-[5-cyano-1-(2-trimethylsilylethanesulfonyl)-indole-3-yl]piperidine-1-sulfonyl}-4-(N,N-dimethylaminosulfonyl)piperazine-2-(R)- carboxamide (0.49 g, 0.62 mmol) and the reaction was placed in a 55° C. oil bath for 30 min. The reaction was diluted with 1 M HCl and concentrated in vacuo. The residue was extracted with ethyl acetate and the organic layer was washed with brine, dried over MgSO$_4$ and concentrated in vacuo to give N-benzyloxy-1-[4-(5-cyanoindol-3-yl) piperidine-1-sulfonyl]- 4-(N,N-dimethylamino-sulfonyl) piperazine-2-(R)-carboxamide (99%) as a tan solid. This material was converted to N-hydroxy-1-[4-(5-cyanoindol-3-yl)piperidine-1-sulfonyl]-4-(N,N-dimethylamino-sulfonyl) piperazine-2-(R)-carboxamide by following Example 16, Step 5.

Proceeding as described in Example 20, Step 1 but substituting N-benzyloxy-1-{4-[5-cyano-1-(2-trimethylsilylethanesulfonyl)indole-3-yl]piperidine-1-sulfonyl}-1,4-piperazine-2-(R)-carboxamide with N-tert-butoxy-4-{[4-(4-chlorobenzoyl)piperidine-1-sulfonyl] amino}piperidine-4-carboxamide [prepared as described in Example 15 above] gave N-tert-butoxy-4-{[4-(4-chlorobenzoyl)piperidine-1-sulfonyl]amino}-1-methanesulfonylpiperidine-4-carboxamide. This material was converted to N-hydroxy-4-{[4-(4-chlorobenzoyl) piperidine-1-sulfonyl]amino}-1-methanesulfonylpiperidine-4-carboxamide by following Example 10, Step 2.

Example 21

Synthesis of N-hydroxy-1-{4-[5-(4-chlorophenyl)pyrrol-2-yl]piperidine-1-sulfonyl}-piperidine-2-(R)-carboxamide

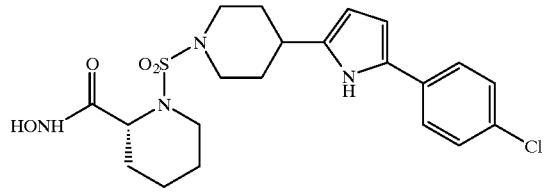

Step 1

A solution of 2-(4-chlorophenyl)pyrrole (409 mg, 2.3 mmol) in methylene chloride (15 ml) was added to a solution of trimethylsilyl trifluoromethanesulfonate (0.45 ml, 2.3 mmol) and methyl (R)-1-(4-piperidone-1-sulfonyl) piperidine-2-carboxylate (700 mg, 2.3 mmol) [prepared as described in Example 18, Step 1] in methylene chloride (20 ml) at 0° C. over a period of 15 min. Triethylsilane (0.71 ml, 9.2 mmol) was added and after stirring for 10 min., sat. sodium bicarbonate solution (35 ml) was added. The reaction mixture was extracted twice with methylene chloride and the combined organic extracts were washed with brine and dried over MgSO$_4$. The organic extracts were concentrated in vacuo and the residue was chromatographed (SiO$_2$, 25% ethyl acetate/hexane), to give methyl 1-{4-[5-(4-chlorophenyl)-pyrrole-2-yl]piperidine-1-sulfonyl}piperidine-2-(R)-carboxylate (47%) as a white solid. This material was converted to N-hydroxy-1-{4-[5-(4-chlorophenyl)pyrrole-2-yl]piperidine-1-sulfonyl}piperidine-2-(R)-carboxamide (47%) by following Example 11, Step 1 and Example 17, Step 4.

Example 22

Synthesis of N-hydroxy-6-amino-2-(R)-{[4-(4-chlorophenyl)piperazine-1-sulfonyl]amino}hexanoamide

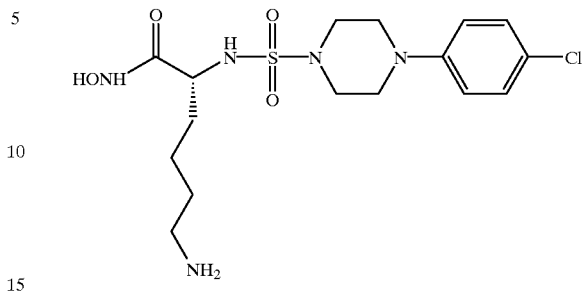

Step 1

Trimethylsilyl iodide (0.026 ml, 0.19 mmol) was added to a solution of N-hydroxy-6-(benzyloxycarbonyl)amino-2-(R)-{[4-(4-chlorophenyl)piperazine-1-sulfonyl] amino}hexanoamide (103 mg, 0.19 mmol) [prepared as described in Example 17, Step 3] in acetonitrile (2 ml) at 0° C. The reaction mixture was allowed to warm to RT, and additional trimethylsilyl iodide (0.47 mmol, 0.065 ml) was added in 0.5 equiv. portions over 2.5 h. Methanol (1.0 ml) was added and the reaction mixture was concentrated in vacuo. The residue was chromatographed (SiO$_2$, 2%–10% methanol/methylene chloride) to give N-hydroxy-6-amino-2-(R)-{[4-(4-chlorophenyl)piperazine-1-sulfonyl] amino}hexanoamide (43.5%) as a tan solid.

Example 23

Synthesis of N-hydroxy-1-[4-(5-fluoroindol-3-yl) piperidine-1-sulfonyl]-4-cyclopropylmethylpiperazine-2-(R)-carboxamide

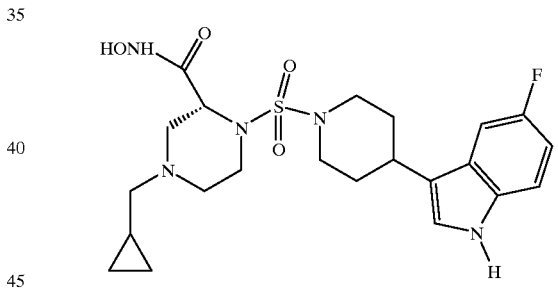

To a solution of N-benzyloxy-1-{4-[5-fluoro-1-(2-trimethylsilylethane-sulfonyl)indol-3-yl]piperidine-1-sulfonyl}piperizine-2-(R)-carboxamide (424 mg, 0.68 mmol) [prepared by proceeding as described in Example 15, Steps 4 and 5, but substituting 4-(4,5,6,7-tetrafluoroindol-3-yl)piperidinesulfamoyl chloride with 4-[5-fluoro-1-(2-trimethylsilylethanesulfonyl)indol-3-yl]piperidinesulfamoyl chloride] in DMF (3 ml) was added potassium carbonate (470 mg, 3.4 mmol) and cyclopropylmethyl bromide (101 mg, 0.75 mmol) and the suspension was vigorously stirred at RT for 24 h. Water was added and the reaction was extracted with ethyl acetate. The organic layer was washed with brine, dried over MgSO$_4$, and concentrated in vacuo. The residue was chromatographed (SiO$_2$, PTLC, 50% ethyl acetate/hexanes) to give N-benzyloxy-1-{4-[5-fluoro-1-(2-trimethylsilylethanesulfonyl)indol-3-yl]piperidine-1-sulfonyl}-4-cyclopropylmethylpiperazine-2-(R)-carboxamide as a pale yellow oil. This material was converted to N-hydroxy-1-[4-(5-fluoroindol-3-yl) piperidine-1-sulfonyl]-4-cyclopropylmethylpiperazine-2-(R)-carboxamide by proceeding as described in Example 20, Step 2.

Example 24
Synthesis of N-hydroxy-1-[4-(4-chlorobenzoyl)piperidine-1-sulfonyl]-4-aminocarbonylpiperazine-2-(R)-carboxamide

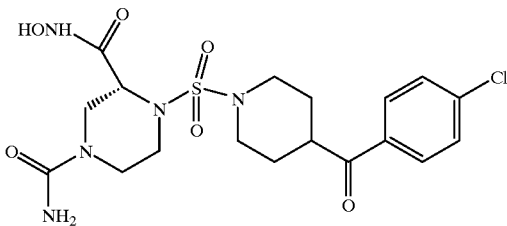

Step 1
To a solution of N-tert-butoxy-1-[4-(4-chlorobenzoyl)piperidine-1-sulfonyl]piperazine-2-(R)-carboxamide [prepared as described in Example 15, above] (600 mg, 1.23 mmol) in methylene chloride (8 ml) was added triethylamine (0.15 ml, 1.1 mmol) and tert-butyl-isocyanate (0.15 ml, 1.33 mmol). The reaction was stirred for 4 h, concentrated in vacuo, and the residue was chromatographed (SiO$_2$, PTLC, 50% ethyl acetate/hexanes) to give N-tertbutoxy-4-tert-butylaminocarbonyl-1-[4-(4-chlorobenzoyl)piperidine-1-sulfonyl]piperazine-2-(R)-carboxamide (75%) as a clear oil.

Step 2
Trifluoroacetic acid (15 ml) was added to N-tert-butoxy-4-tert-butylaminocarbonyl-1-[4-(4-chlorobenzoyl)piperadine-1-sulfonyl]piperazine-2-(R)-carboxamide (0.45 g, 0.92 mmol) [prepared as described in Step 2 above] and the reaction was stirred for 36 h. The reaction was concentrated in vacuo, and the residue was chromatographed (SiO$_2$, PTLC, 10% methanol/methylene chloride) to give N-hydroxy-1-[4-(4-chlorobenzoyl)piperidine-1-sulfonyl]-4-aminocarbonylpiperazine-2-(R)-carboxamide (55%) as a pale pink solid.

Example 25
Synthesis of N-hydroxy-2-(R)-{[4-(4-chlorophenylaminocarbonyl)piperazine-1-sulfonyl]amino}propionamide

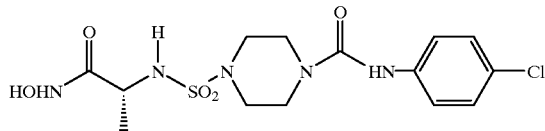

Step 1
Hydrogen chloride gas was bubbled through a solution of methyl 2-(R)-[(4-tert-butoxycarbonylpiperazine-1-sulfonyl)amino]propionate (3.6 g, 10.7 mmol) [prepared by proceeding as described in Example 2, but substituting 4-(5-chloropyridin-2-yloxy)piperidine and D-valine methyl ester with 1-tert-butoxycarbonyl-1,4-piperazine and D-alanine methyl ester, respectively] in 10% dioxane/methylene chloride (100 ml) for 10 min. The reaction was stirred at RT for 4 h and concentrated in vacuo to give methyl 2-(R)-[(piperazine-1-sulfonyl)amino]propionate (91%) as a white solid that was used without further purification.

Step 2
To a solution of 4-chlorophenylisocyanate (0.33 g, 2.14 mmol) in diethyl ether (30 ml) was added methyl 2-(R)-[(piperazine-1-sulfonyl)amino]propionate (0.42 g, 1.8 mmol) [prepared as described in Step 1 above]. The reaction was stirred at RT for 2 h and filtered. The solid was washed with additional ether and the solid was collected to give methyl 2-(R)-{[4-(4-chlorophenylamino-carbonyl)piperazine-1-sulfonyl]amino}propionate (55%). This material was converted to N-hydroxy-2-(R)-{[4-(4-chlorophenylaminocarbonyl)piperazine-1-sulfonyl]amino}propionamide by following Example 13.

Proceeding as described in Example 25, Step 2 but substituting 4-chlorophenylisocyanate with 4-chlorobenzylisocyanate gave N-hydroxy-2-(R)-{[4-(4-chlorobenzylaminocarbonyl)piperazine-1-sulfonyl]amino}propionamide.

Example 26
Synthesis of N-hydroxy-2-(R)-{[4-(5-chloropyridin-2-yl)piperazine-1-sulfonyl]amino}3-(phenylthio)propionamide

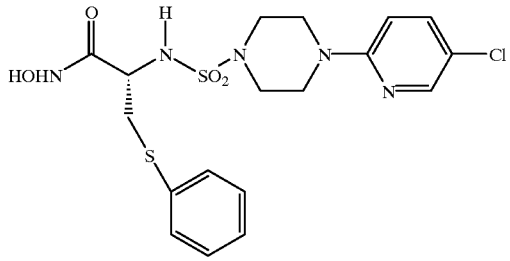

Step 1
Hydrogen chloride gas was bubbled through a solution N-tert-butoxy-2-(R)-tert-butoxycarbonylamino-3-(phenylthio)propionamide (3.45 g, 9.16 mmol) [prepared as described in Example 10, Step 1, by substituting 1-[4-(4-chlorobenzoyl)piperidine-1-sulfonyl]piperidine-2-(R)-carboxylic acid with 2-(R)-tert-butoxycarbonylamino-3-(phenylthio)propionic acid] in methylene chloride at RT for 20 min. After 2 h, the reaction mixture was concentrated in vacuo to give N-tert-butoxy-2-(R)-amino-3-(phenylthio)propionamide HCl salt (79%) as a white solid that was used without further purification.

Step 2
To a solution of N-tert-butoxy-2-(R)-amino-3-(phenylthio)propionamide HCl salt (0.40 g, 1.31 mmol) and triethylamine (0.3 ml, 2.6 mmol) in tetrahydrofuran (25 ml) was added 4-(5-chloropyridin-2-yl)piperazinesulfamoyl chloride (0.39 g, 1.31 mmol). The reaction was stirred overnight at reflux and concentrated in vacuo. The residue was diluted with ethyl acetate (70 ml) and washed with water, brine, and dried over MgSO$_4$. The organics were concentrated in vacuo and the residue was chromatographed (SiO$_2$, 30% ethyl acetate/hexane) to give N-tert-butoxy-2-(R)-{[4-(5-chloropyridin-2-yl)piperazine-1-sulfonyl]amino}-3-(phenylthio)-propionamide (23%) as a white solid. This material was converted to N-hydroxy-2-(R){[4-(5-chloropyridin-2-yl)piperazine-1-sulfonyl]amino}-3-(phenylthio)propionamide by following Example 24, Step 2.

Example 27
Synthesis of N-hydroxy-1-{[4-(4-chlorophenyl)piperazine-1-sulfonyl]amino}cyclohexane-1-carboxamide

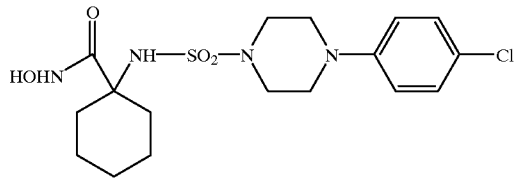

Step 1
To a suspension of methyl 1-aminocyclohexane-1-carboxylate HCl salt (4.06 g, 20.9 mmol) in acetonitrile (37 ml) was added sulfuryl chloride (26.2 ml, 326 mmol) and antimony pentachloride (0.17 ml, 2.4 mmol). The reaction was heated at 80° C. using a calcium sulfate drying tube overnight. The reaction was concentrated in vacuo to give methyl 1-(chlorosulfonylamino)cyclohexane-1-carboxylate (85%) as a yellow oil that was used without further purification. This material was converted to N-hydroxy-1-{[4-(4-chlorophenyl)piperazine-1-sulfonyl]amino}cyclohexane-1-carboxamide by following Examples 2 and Example 13 except that the reaction was heated at 45° C.

Example 28
Synthesis of N-hydroxy-4-(N,N-dimethylaminocarbonyl)-1-[4-(4-fluorophenyl)-1,2,3,6-tetrahydropyridine-1-sulfonyl]piperizine-2-(R)-carboxamide

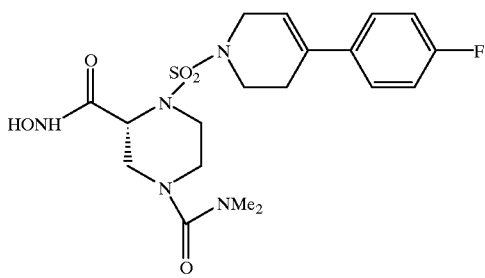

Step 1
Piperazine-2(R)-carboxylic acid dihydrochloride (5.0 g, 24.6 mmol) was suspended in hexamethyldisilazane (50 ml). The reaction mixture was heated at about 120° C. to achieve complete dissolution and then cooled to about 80° C. A solution of dimethylcarbamoyl chloride (3.18 g, 29.5 mmol) in acetonitrile (5 ml) was added and the reaction mixture is stirred overnight at about 80° C. A solution of 4-(4-fluorophenyl)-1,2,3,6-tetrahydropyridine sulfamoyl chloride (5.4 g, 19.58 mmol) in acetonitrile (10 ml) was added and the resulting reaction mixture was stirred at about 80° C. till the completion of the reaction (followed by HPLC). The reaction mixture was cooled and then quenched with methanol. The resulting slurry was concentrated and then replaced into water. The aqueous slurry was made alkaline with ammonium hydroxide and then washed with dichloromethane. The aqueous phase was acidified with dilute HCl and extracted with dichoromethane. The organic extracts were washed with water and then evaporated to dryness to yield 4-(N,N-dimethylaminocarbonyl)-1-[4-(4-fluoropheny)-1,2,3,6-tetrahydropyridinesulfonyl]piperazine-2(R)-carboxylic acid (6.1 g) as a beige colored solid.

Step 2

4-N,N-dimethylaminocarbonyl-1-[4-(4-fluorophenyl)-1,2,3,6-tetrahydropyridinesulfonyl]piperazine-2(R)-carboxylic acid (1.0 g, 2.27 mmol), [prepared as described in Step 1 above] was suspended in dichloromethane (8 ml) containing DMF (0.05 ml). The reaction mixture was cooled to −5° C. and oxalyl chloride (340 mg, 2.67 mmol) dissolved in dichloromethane (1 ml) was added. The reaction mixture was allowed to warm up slowly to about 15° C. and stirred for about 2 hours to achieve a clear solution. The reaction mixture was cooled to about −10° C. and a reagent mixture consisting of aqueous hydroxylamine (48%, 0.85 g, 12.35 mmol), THF (4.8 ml) and tert-butanol (1.9 g) was added slowly maintaining reaction temperature below 5° C. The reaction mixture was stirred at 5–15° C. for about 1 h and then replaced by vacuum distillation into acetonitrile (15 ml). Water (10 ml) was added to achieve a clear solution. Acetonitrile was slowly distilled off under reduced pressure to induce crystallization. After achieving a final volume of about 15 ml, distillation was discontinued and the resulting slurry was stirred at ambient temperature for 1 h. The precipitated product was isolated by filtration, washed successively with water, ethanol and isopropyl acetate and then dried under vacuum to yield N-hydroxy-4-(N,N-dimethylaminocarbonyl)-1-[4-(4-fluorophenyl)-1,2,3,6-tetrahydropyridine-1-sulfonyl]piperazine-2-(R)-carboxamide (850 mg) as a colorless crystalline solid.

1. Proceeding as described in Example 28, Step 4, but substituting 4-(4-fluoro-phenyl)-1,2,3,6-tetrahydropyridinesulfamoyl chloride with dimethylaminosulfamoyl chloride and using 3 equivalents of trimethylsilylcyanide gave 1-benzyloxycarbonyl-4-dimethylaminosulfonylpiperazine-2-(RS)-carboxylic acid. This material was converted to N-hydroxy-4-(N,N-dimethylaminosulfonyl)-1-[4-(4-fluorophenyl)-1,2,3,6-tetrahydropyridine-1-sulfonyl]piperazine-2-(RS)-carboxamide by proceeding as described in Example 28, Steps 3–5 above.

2. Proceeding as described in Example 28, Step 1 above, but substituting 1-benzyloxycarbonyl-4-tert-butoxycarbonyyl-2-(R)-carboxylic acid with benzyl 1-benzyloxycarbonyl-4-tert-butoxycarbonylpiperazine-2-(RS)-carboxylate [prepared from 1-benzyloxycarbonyl-4-tert-butoxycarbonylpiperazine-2-(RS)-carboxylic acid as described in Ono, N., et al. *Bull. Chem. Soc. Jpn.*, 51, 2401, (1978)] gave benzyl 1-benzyloxycarbonylpiperazine-2-(RS)-carboxylate. This material was first converted to benzyl 1-benzyloxycarbonyl-4-(2,2,2-trifluoroethyl)piperazine-2-(RS)-carboxylate by reacting it with 2,2,2-trifluoroethyl trichloromethanesulfonate as described in Gao, Y., et al. *J. Med. Chem.*, 33, 39, (1990) and then to N-hydroxy-1-[4-(4-fluorophenyl)-1,2,3,6-tetrahydropyridine-1-sulfonyl]-4-(2,2,2-trifouoroethyl)piperizine-2-(RS)-carboxamide by following Example 28, Steps 3–5 described above.

Example 29

Synthesis of N-hydroxy-4-(N,N-dimethylaminocarbonyl)-1-[4-(4-fluorophenyl)-piperidine-1-sulfonyl]piperazine-2-(R)-carboxamide

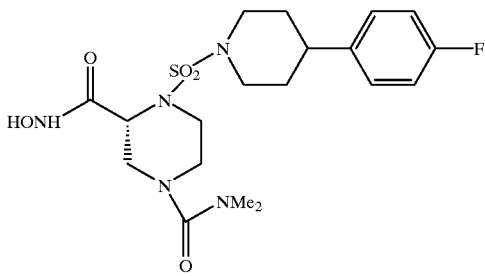

A mixture of 4-(N,N-dimethylaminocarbonyl)-1-[4-(4-fluorophenyl)-1,2,3,6-tetrahydropyridine-1-sulfonyl]piperazine-2-(R)-carboxylic acid (1.39 g, 3.16 mmol) [prepared as described in Example 28, Steps 1–4] and 10% Pd/C (0.7 g) in 10% tetrahydrofuran/ethanol (45 ml) was stirred under an atmosphere of hydrogen (1 atm) overnight. The reaction mixture was filtered through Celite with excess ethanol and the filtrate was concentrated in vacuo to give 4-(N,N-dimethylaminocarbonyl)-1-[4-(4-fluorophenyl)piperidine-1-sulfonyl]piperazine-2-(R)-carboxylic acid (88%) as a white solid. This material was converted to N-hydroxy-4-dimethylaminocarbonyl-1-[4-(4-fluorophenyl)piperidine-1-sulfonyl]piperazine-2-(R)-carboxamide by following the procedure described in Example 28, Step 5 above.

Example 30

Formulation Examples

The following are representative pharmaceutical formulations containing a compound of formula I.

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
| --- | --- |
| compound of this invention | 0.2 mg–20 mg |
| sodium acetate buffer solution, 0.4M | 2.0 ml |
| HCl (1N) or NaOH (1N) | q.s. to suitable pH |
| water (distilled, sterile) | q.s. to 20 ml |

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| | |
| --- | --- |
| compound of the invention | 500 mg |
| Witepsol ® H-15 | balance |

Example 31

Isolation of Matrix Metalloproteases

The catalytic domain of human collagenase-1 was expressed as a fusion protein with ubiquitin in *E. Coli* as described in Gehring, E. R. et al., *J. Biol. Chem.*, 270, 22507, (1995). After purification of the fusion protein, the collagenase-1 catalytic domain was released by treatment with 1 mM of aminophenylmercuric acetate (APMA) for 1 hour at 37° C. and then purified by zinc chelate chromatography.

Human collagenase-2 and gelatinase B were isolated in active form from buffy coats as described in Mookhtiar, K. A. et al., *Biochemistry*, 29, 10620, (1990).

The propeptide and catalytic domain portion of human collagenase-3 was expressed in *E. Coli* as an N-terminal fusion protein with ubiquitin. After purification, the catalytic domain was released by treatment with 1 mM APMA for 1 hour at 37° C., and then purified by zinc chelate chromatography.

Rat collagenase-3 was purified in active form from the culture media of uterine smooth muscle cells as described in Roswit, W. T. et al., *Arch. Biochem. Biophys.*, 225, 285–295 (1983).

The catalytic and fibronectin-like portion of human progelatinase A was expressed as a fusion protein with ubiquitin in *E. Coli*. The assays were carried out on autolytically activated material.

The rat progelatinase A was purified from the culture media of interleukin-1 stimulated keratinocytes, activated by treatment with 1 mM APMA for 1 hour at 37° C., and subsequently dialyzed to remove excess APMA.

Human prostromelysin-1 was purified from the culture medium of synovial fibroblasts by affinity chromatography using an immobilized monoclonal antibody. The zymogen was activated by treatment with trypsin (1.5 μg/ml) for 1 hour at 23° C. to give a mixture of 45 and 28 kD species. The catalytic domain of human stromelysin-1 was prepared by expression and purification of prostromelysin-1 from E. Coli and activated with 1 mM APMA for 1 hour at 37° C., followed by dialysis.

Rat prostromelysin-1 was expressed in Chinese Hamster Ovary cells and purified from the culture media. It was activated by 1 mM APMA for 1 hour at 37° C., followed by dialysis.

Human promatrilysin was expressed and purified from Chinese Hamster Ovary cells as described in Barnett, J. et al., *Prot. Express. Pur.*, 5, 27, (1994). The zymogen was activated by treatment with 1 mM APMA for 1 hour at 37° C., and then purified by zinc chelate chromatography.

Example 32
Inhibition of Matrix Metalloproteases in vitro

The matrix metalloprotease inhibitory activity of compounds of this invention in vitro was determined based on the hydrolysis of MCA-Pro-Leu-Gly-Leu-DPA-Ala-Arg-$NH_2$ (Bachem, Inc.) at 37° C. as described in Knight, C. G., et al., *FEBS Lett.*, 296, 263–266 (1992).

The matrix metalloprotease enzyme was diluted with assay buffer (50 mM Tricine pH 7.5, 200 mM NaCl, 10 mM $CaCl_2$, and 0.005% Brij-35) containing 10 μmole of above substrate dissolved in DMSO. Compounds of the invention dissolved in DMSO or only DMSO (control samples) were added such that the final DMSO concentration in all assays was 2.5%. The fluorescence changes were monitored with a Perkin-Elmer LS-50B flourimeter using an excitation wavelength of 328 nm and an emission wavelength of 393 nm.

Compounds of this invention were active in this assay.

MMP inhibitory activities (expressed as $IC_{50}$, the inhibitor concentration causing 50% inhibition of the activity in the control) of some compounds of the invention were:

| CPD # | Collagenase-I $IC_{50}$, nm | Collagenase-III $IC_{50}$, nm | CPD # | Collagenase-I $IC_{50}$, nm | Collagenase-III $IC_{50}$, nm |
|---|---|---|---|---|---|
| 1 | 550 | 660 | 262 | 88 | 0.13 |
| 16 | 22000 | 21 | 286 | 29 | 0.063 |
| 50 | 220 | 1.3 | 294 | >50000 | 340 |
| 51 | 490 | 2.6 | 298 | 130 | 0.2 |
| 59 | 110 | 0.18 | 299 | >50000 | 410 |
| 74 | 7600 | 0.73 | 309 | >50000 | 500 |
| 102 | 338 | 0.92 | 315 | NA | 0.1 |
| 105 | 129 | 0.59 | 342 | 170 | 2.1 |
| 106 | 223 | 0.52 | 345 | 530 | 6.6 |
| 133 | 20000 | 18 | 355 | 650 | 56 |
| 177 | 9300 | 1.6 | 401 | 250 | 0.19 |
| 179 | 23 | 0.073 | 413 | 9300 | 260 |
| 242 | 67 | 0.063 | 414 | >50000 | 3400 |
| 254 | >50000 | 181 | 430 | 2200 | 890 |
| 255 | 120 | 0.19 | 431 | >50000 | 6500 |
| 256 | 26000 | 33 | | | |

Example 33
Degradation of Cartilage Plug in vitro

The ability of the compounds of this invention to inhibit the degradation of the collagen matrix (as judged by release of hydroxyproline) was determined by the cartilage plug degradation assay in vitro by following a slight modification of the method described in Spirito, S.,Doughty, E., e t al., "Metalloproteinase inhibitors halt collagen breakdown in IL-1 induced bovine nasal cartilage cultures" *Inflamm. Res.*, 44, Supp. 2: S131–S132, (1995).

Cartilage explants prepared from freshly sacrificed bovine knee joints were added to the culture medium (Dubelco's modified eagle medium, Gibco # 21063-001, Gibco BRL Products, Gaithersburg, Md.), without phenol red, but with HEPES, and L-glutarnine and fungizone 2.5 μg/ml, gentamicin 50 μg/ml, penicillin 100 μ/ml, and streptomycin 100 ug/ml). The cultures were stimulated with IL-1-α at a final concentration of 20 ng/ml. Compounds of Formula (I), were added at concentrations between 10 and 300 nm in DMSO. The control samples contained only IL-1-α. The cultures were incubated at 37° C. in an atmosphere of air with 6% $CO_2$ for 21 days during which time the medium was changed twice/week. The cartilage plugs were removed, hydrolyzed and the hydroxyproline content was determined. The MMP inhibitory activity of test materials is the measure of the hydroxyproline content in the test group relative to the vehicle treated group (control group).

The MMP inhibitory activities of some compounds of this invention in this assay were:

| CPD# | % protection | CPD# | % protection |
|---|---|---|---|
| 50 | 71 | 60 | 89 |
| 51 | 35 | 100 | 68 |
| 59 | 54 | 242 | 27 |

Example 34
Cartilage Plug Degradation in vivo

The activity of compounds of this invention in inhibiting the destruction of the collagen matrix was determined by the cartilage plug implant assay, in rats, using a minor modification of the method described in Bishop, J., et al.,*J. Pharm. Tox. Methods*, 30, 19, (1993).

In this assay, bovine nasal cartilage plugs weighing approximately 20 mg were embedded in polyvinyl sponges impregnated with Mycobacterium tuberculosis and implanted subcutaneously in female Lewis rats. After a week, test materials, dissolved in DMSO (using a volume required for 5% final volume), were administered to female rats prepared as solutions or suspensions in an aqueous vehicle containing 0.9% sodium chloride, 0.5% sodium carboxymethyl-cellulose, 0.4% polysorbate 80, 0.9% benzyl alcohol (CMC vehicle). Control rats received vehicle alone. The experiment was terminated after 8 or 9 days. The plugs were removed, weighed, hydrolyzed, and the hydroxyproline content was measured. The MMP inhibitory activity of test materials is the measure of the hydroxyproline content in the test group relative to the vehicle treated group (control group).

The MMP inhibitory activities of some compounds of this invention in this assay were:

| CPD# | % protection | CPD# | % protection |
|---|---|---|---|
| 50 | 70 | 74 | 46 |
| 51 | 45 | 100 | 40 |
| 59 | 58 | 179 | 63 |

Example 35
Inhibition of TNF release in vitro Assay

The activity of compounds of this invention in inhibiting the TNF release was determined, using the a minor modification of the method described in Pradines-Figueres, A. and Raetz, C. R. H.,*J. Biol. Chem.*, 267 (32), 23261, (1992).

Human Monomac 6 cells (Ziegler-Heitbrock, H. W. L., et al., *Int. J. Cancer*, 41, 456, (1988)) were cultured at 37° C.

in RPMI 1640 medium containing 10% fetal calf serum to a density of 1×10⁵ cells/ml. 0.23 ml of these cells were placed in each well of a tissue culture plate and the cells were incubated for 15 min. The test compounds were dissolved in above mentioned medium and added and the incubation was continued for an additional 15 min. 10 µl of an lipopolysaccharide/phorbol-12-myristate-13-acetate (LPS/PMA) mixture was added such that the final concentration of lipopolysaccharide was 10 ng/ml and the final concentration of phorbol-12-myristate-13-acetate was 30 ng/ml. The cells were incubated for 2 h after which the plate was centrifuged and the medium was removed and analyzed for TNF content. The analysis was performed using a TNF Quantikine® Immunoassay (R & D Systems, Minneapolis, Minn. 55413) by following the manufacturer's protocol.

Compounds of this invention were active in this assay.

The TNF-α inhibitory activity of test materials, i.e., the measure of the TNF-α content in the test group relative to the vehicle treated group (control group) was:

| CPD # | Conc. µM | % inhibition | CPD # | Conc. µM | % inhibition |
|---|---|---|---|---|---|
| 1 | 10 | <15 | 298 | 2 | 70 |
| 16 | 10 | <15 | 299 | 2 | 90 |
| 50 | 10 | <15 | 309 | 2 | 94 |
| 74 | 10 | 17 | 313 | 2 | 73 |
| 102 | 10 | 56 | 314 | 2 | 72 |
| 105 | 10 | 20 | 315 | 2 | 86 |
| 106 | 10 | 41 | 319 | 2 | 81 |
| 133 | 10 | 32 | 321 | 2 | 93 |
| 177 | 10 | <15 | 355 | 10 | <15 |
| 179 | 10 | <15 | 375 | 2 | 85 |
| 242 | 10 | 85 | 381 | 2 | 10 |
| 254 | 10 | 94 | 384 | 10 | 96 |
| 255 | 10 | 97 | 401 | 10 | 97 |
| 256 | 10 | 79 | 402 | 10 | 93 |
| 262 | 2 | 90 | 409 | 10 | 86 |
| 294 | 2 | 97 | | | |

Example 36
inhibition of LPS induced TNF-α Production in Mice in vivo Assay

The activity of compounds of this invention in inhibiting the TNF-α release was determined, using minor modification of the methods described in Zanetti, G.; Heumann, D., et. al.,"Cytokine production after intravenous or peritoneal Gram-negative bacterial challenge in mice" *j. Immunol.*, 148, 1890, (1992) and Sekut, L., Menius, J. A., et. al., "Evaluation if the significande of elevated levels of systemic and localized tumor necrosis factor in different animal models of inflammation" *J. Lab. Clin. Med.*, 124, 813, (1994).

Female Balb/c mice were anesthetized and injected subcutaneously with the test compounds dissolved in CMC vehicle or hydroxypropylmethyl cellulose based vehicle. Control animals received only the vehicle. After 1 h, LPS (50 µg/mouse, Sigma #13129, Sigma Chemical Co., St. Louis, Mo.) was injected intraperitoneally. After 1.5 h, blood was collected from the retro-orbital plexus region of the animals in a microtainer serum separator tube (Becton Dickinson, Cat. No. #5960, Becton Dickinson & Co., Franklin Lakes, N.J.). The sera was separated and the amount of TNF-α was determined using the EM-TNFA® kit (Endogen, Woburn, Mass.) by following the manufacturer's protocol.

The TNF inhibitory activities of some compounds of the invention were:

| CPD # | % inhibition | CPD # | % inhibition |
|---|---|---|---|
| 134 | 42 | 294 | 90 |
| 216 | 41 | 299 | 52 |
| 232 | 73 | 309 | 46 |
| 233 | 46 | 319 | 50 |
| 234 | 46 | 321 | 50 |
| 262 | 50 | | |

Example 37
TNF Receptor Shedding Immunoassay

Human Monomac 6 cells are cultured to a density of 1×10⁶ cells/mL at 37° C. in RPMI 1640 medium supplemented with 10% fetal calf serum. All subsequent incubations are performed at 37° C. 230 µl of these cells are placed in each well of a 96-well tissue culture plate and the cells are incubated for 15 minutes. 10 µl of desired concentration of compounds of formula (I) in the above mentioned medium are added to the appropriate wells and incubated for an additional 15 minutes. To each well is added 10 µl of PMA at a final concentration of 30 ng/mL. The cells are then incubated for 16 hours after which the plate is centrifuged and the medium is removed and analyzed for TNF receptor content. The analysis is performed using an R & D Systems TNF receptor Quantikine® Immunoassay (Endogen, Woburn, Mass.) following the manufacturer's protocol. Measurements of each TNF receptor (receptor I and receptor II) are performed in this way. The IC₅₀ is calculated from the percent inhibition of TNF released into the medium.

The compounds of Formula (I), when tested in this assay, exhibited the ability to selectively inhibit TNF production.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:

1. A compound selected from the group of compounds represented by formula (I):

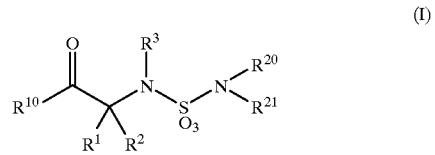

wherein:

R¹ and R² are independently selected from hydrogen, alkyl, alkenyl, haloalkyl, cycloalkyl, cycloalkylalkyl, aryl, aralkyl, heteroaryl, heteroaralkyl, heterocyclo, heterocycloalkyl, heteroalkyl, or -(alkylene)—C(O)—X where X is alkyl, haloalkyl, alkoxy, haloalkyloxy, amino, monosubstituted amino, disubstituted amino, aryl, aralkyl, aryloxy, heteroaryloxy, hydroxy, aralkyloxy, heteroaralkyloxy, or heteroaryl;

$R^3$ is hydrogen, alkyl, alkenyl, haloalkyl, cycloalkyl, cycloalkylalkyl, aryl, aralkyl, aralkenyl, heteroaryl, heteroaralkyl, heteroaralkenyl, heterocycloalkyl, heteroalkyl, (diphenylmethyl)alkyl, or -(alkylene)—C(O)—X where X is alkyl, haloalkyl, alkoxy, haloalkyloxy, amino, monosubstituted amino, disubstituted amino, aryl, aralkyl, aryloxy, heteroaryloxy, hydroxy, aralkyloxy, heteroaralkyloxy, or heteroaryl;

$R^{10}$ is —OH;

$R^{20}$ and $R^{21}$ together with the nitrogen atom to which they are attached form a heterocycloamino group that is fused to a cycloalkyl, aryl or heteroaryl ring; and their pharmaceutically acceptable salts, prodrugs, individual isomers, and mixtures of isomers, provided that:

$R^1$, $R^2$, and $R^3$ are not all hydrogen.

2. The compound of claim 1 wherein the heterocycloamino group is a monovalent cyclic group of 4 to 8 ring atoms, wherein:
  (i) at least one ring atom is nitrogen;
  (ii) optionally one or two additional ring heteroatoms may be selected from the group consisting of nitrogen, oxygen, or $S(O)_n$, where n is an integer from 0 to 2; and
  (iii) the remaining ring atoms are carbon, wherein one or two carbon atoms may optionally be replaced by a carbonyl group.

3. The compound of claim 2 wherein the heterocycloamino group, formed by $R^{20}$ and $R^{21}$, is pyrrolidino, piperidino, morpholino, piperazino, thiomorpholino, thiomorpholino-1-oxide, or thiomorpholino-1,1-dioxide, and derivatives thereof.

4. The compound of claim 1 wherein the cycloalkyl, to which the heterocycloamino group formed by $R^{20}$ and $R^{21}$ is fused, is a saturated monovalent cyclic hydrocarbon radical of three to six ring carbons.

5. The compound of claim 4 wherein the cycloalkyl is cyclopropyl, cyclopentyl, or cyclohexyl.

6. The compound of claim 1 wherein the aryl, to which the heterocycloamino group formed by $R^{20}$ and $R^{21}$ is fused, is a monovalent monocyclic or bicyclic aromatic hydrocarbon radical of 6 to 10 ring atoms that is optionally substituted independently with one or more substituents selected from:

alkyl; haloalkyl; halo; nitro; acyloxy; cyano; cycloalkyl; cycloalkylalkyl; optionally substituted phenyl; optionally substituted phenylalkyl; heteroaryl; heteroaralkyl;

—OR wherein R is hydrogen, alkyl, haloalkyl, alkenyl, cycloalkyl, cycloalkylalkyl, optionally substituted phenyl, heteroaryl, optionally substituted phenylalkyl, or heteroaralkyl;

—NRR' wherein R and R' are independently hydrogen, alkyl, alkenyl, haloalkyl, cycloalkyl, cycloalkylalkyl, optionally substituted phenyl, optionally substituted phenylalkyl, optionally substituted phenylalkenyl, heteroaryl, or heteroaralkyl;

—C(O)R wherein R is hydrogen, alkyl, alkenyl, cycloalkyl, cycloalkylalkyl, haloalkyl, optionally substituted phenyl, optionally substituted phenylalkyl, optionally substituted phenylalkenyl, heteroaryl, heteroaralkyl, or heteroaralkenyl;

—$S(O)_nR$ wherein n is an integer from 0 to 2 and R is hydrogen (provided that n is zero), alkyl, haloalkyl, alkenyl, cycloalkyl, cycloalkylalkyl, optionally substituted phenyl, heteroaryl, optionally substituted phenylalkyl, or heteroaralkyl;

—$SO_2NRR'$ wherein R and R' are independently hydrogen, alkyl, alkenyl, haloalkyl, cycloalkyl, cycloalkylalkyl, optionally substituted phenyl, optionally substituted phenylalkyl, optionally substituted phenylalkenyl, heteroaryl or heteroaralkyl;

—COOH; -(alkylene)—COOH; -(alkenylene)—COOH;

—COOR$^a$; -(alkenylene)—COOR$^a$; -(alkylene)—COOR$^a$ wherein R$^a$ is alkyl, optionally substituted phenylalkyl, or heteroaralkyl;

—CONR'R"; -(alkylene)—CONR'R" wherein R' and R" are independently selected from hydrogen, alkyl, cycloalkyl, cycloalkylalkyl, optionally substituted phenyl, optionally substituted phenylalkyl, heteroaryl, and heteroaralkyl;

—NRC(O)R' wherein R is hydrogen or alkyl and R' is hydrogen, alkyl, alkenyl, cycloalkyl, cycloalkylalkyl, haloalkyl, optionally substituted phenyl, optionally substituted phenylalkyl, optionally substituted phenylalkenyl, heteroaryl, heteroaralkenyl, or heteroaralkyl;

—$NRSO_2R'$ wherein R is hydrogen or alkyl and R' is alkyl, alkenyl, cycloalkyl, cycloalkylalkyl, haloalkyl, optionally substituted phenyl, optionally substituted phenylalkyl, optionally substituted phenylalkenyl, heteroaryl, heteroaralkenyl, or heteroaralkyl; or —$NRSO_2NR'R"$ wherein R is hydrogen or alkyl and R' and R" are independently hydrogen, alkyl, alkenyl, haloalkyl, cycloalkyl, cycloalkylalkyl, optionally substituted phenyl, optionally substituted phenylalkyl, or optionally substituted phenylalkenyl.

7. The compound of claim 6 wherein the aryl, to which the heterocycloamino group formed by $R^{20}$ and $R^{21}$ is fused, is phenyl, 1-napthyl, or derivatives thereof.

8. The compound of claim 1 wherein the heteroaryl, to which the heterocycloamino group formed by $R^{20}$ and $R^{21}$ is fused, is a monovalent monocyclic or bicyclic aromatic radical of 5 to 10 ring atoms wherein:
  (i) one, two or three ring heteroatoms are selected from nitrogen, oxygen, or sulfur; and
  (ii) the remaining ring atoms are carbon.

9. The compound of claim 8 wherein the heteroaryl, to which the heterocycloamino group formed by $R^{20}$ and $R^{21}$ is fused, is optionally substituted independently with one or more substituents, preferably one or two substituents, selected from:

alkyl; haloalkyl; halo; nitro; cyano; cycloalkyl; cycloalkylalkyl; optionally substituted phenyl; optionally substituted phenylalkyl;

—OR wherein R is hydrogen, alkyl, haloalkyl, alkenyl, cycloalkyl, cycloalkylalkyl, optionally substituted phenyl, or optionally substituted phenylalkyl;

—NRR' wherein R and R' are independently hydrogen, alkyl, alkenyl, haloalkyl, cycloalkyl, cycloalkylalkyl, optionally substituted phenyl, optionally substituted phenylalkyl, or optionally substituted phenylalkenyl;

—C(O)R wherein R is hydrogen, alkyl, alkenyl, cycloalkyl, cycloalkylalkyl, haloalkyl, optionally substituted phenyl, optionally substituted phenylalkyl, or optionally substituted phenylalkenyl;

—$S(O)_nR$ wherein n is an integer from 0 to 2 and R is hydrogen (provided that n is zero), alkyl, haloalkyl, alkenyl, cycloalkyl, cycloalkylalkyl, optionally substituted phenyl, optionally substituted phenylalkyl;

—$SO_2NRR'$ wherein R and R' are independently hydrogen, alkyl, alkenyl, haloalkyl, cycloalkyl, cycloalkylalkyl, optionally substituted phenyl, optionally substituted phenylalkyl, or optionally substituted phenylalkenyl);

—COOH; -(alkylene)—COOH; -(alkenylene)COOH;

—COOR$^a$; -(alkenylene)—COOR$^a$; -(alkylene)—COOR$^a$ wherein R$^a$ is alkyl, or optionally substituted phenylalkyl;

—CONR'R"; -(alkylene)—CONR'R" wherein R' and R" are independently selected from hydrogen, alkyl, cycloalkyl, cycloalkylalkyl, optionally substituted phenyl, or optionally substituted phenylalkyl;

—NRC(O)R' wherein R is hydrogen or alkyl and R' is hydrogen, alkyl, alkenyl, cycloalkyl, cycloalkylalkyl, haloalkyl, optionally substituted phenyl, optionally substituted phenylalkyl, or optionally substituted phenylalkenyl;

—NRSO$_2$R' wherein R is hydrogen or alkyl and R' is alkyl, alkenyl, cycloalkyl, cycloalkylalkyl, haloalkyl, optionally substituted phenyl, optionally substituted phenylalkyl, or optionally substituted phenylalkenyl;

—NRSO$_2$NR'R" wherein R is hydrogen or alkyl and R' and R" are independently hydrogen, alkyl, alkenyl, haloalkyl, cycloalkyl, cycloalkylalkyl, optionally substituted phenyl, optionally substituted phenylalkyl, or optionally substituted phenylalkenyl; or an amino protecting group.

10. The compound of claim 8 wherein the heteroaryl, to which the heterocycloamino group formed by R$^{20}$ and R$^{21}$ is fused, is pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl and benzodiazepin-2-one-5-yl, or derivatives thereof.

11. The compound of claim 1, wherein the heterocycloamino group, formed by R$^{20}$ and R$^{21}$, is fused to the cycloalkyl, aryl, or heteroaryl ring to form a fused ring system selected from the group consisting of indolino, 1,2,3,4-tetrahydro-α-carbolino, 1,2,3,4-tetrahydro-β-carbolino, 1,2,3,4-tetrahydro-γ-carbolino, tetrahydroisoquinolyl, and 1,3-dihydro-2H-1,4,-benzodiazepin-2-one-5-yl, and derivatives thereof.

12. The compound of claim 11 wherein:
 (i) the fused ring system is 1,2,3,4-tetrahydro-β-carbolino;
 (ii) R$^1$ is hydrogen, methyl, or 2-propyl; and
 (iii) R$^2$ and R$^3$ are hydrogen.

13. The compound of claim 1 wherein:
 (i) R$^1$ is alkyl, aryl, aralkyl, or heteroaralkyl;
 (ii) R$^2$ is hydrogen; and
 (iii) R$^3$ is hydrogen, alkyl, aralkyl, heteroaralkyl, or heteroalkyl.

14. A pharmaceutical composition comprising a therapeutically effective amount of a compound of claim 1 and a pharmaceutically acceptable excipient.

15. A method of treatment of a disease in a mammal treatable by administration of a metalloprotease inhibitor, comprising administration to the mammal of a therapeutically effective amount of a compound of claim 1.

* * * * *

UNITED STATES PATENT AND TRADEMARK OFFICE
CERTIFICATE OF CORRECTION

PATENT NO : 5,998,412

DATED : December 7, 1999

INVENTOR(S) : Broka, et al.

It is certified that error appears in the above-identified patent and that said Letters Patent is hereby corrected as shown below:

In the Abstract, front page, delete incorrect structure of formula (I)

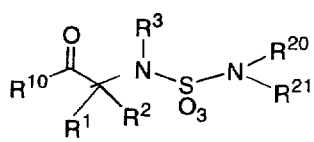

(I)

and replace with

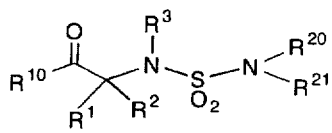

(I)

UNITED STATES PATENT AND TRADEMARK OFFICE
CERTIFICATE OF CORRECTION

PATENT NO : 5,998,412

DATED : December 7, 1999

INVENTOR(S) : Broka, et al.

It is certified that error appears in the above-identified patent and that said Letters Patent is hereby corrected as shown below:

Column 3, lines 32-40, delete incorrect structure of formula (I)

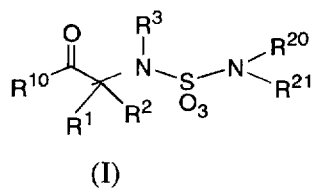

(I)

and replace with

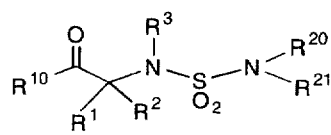

(I)

UNITED STATES PATENT AND TRADEMARK OFFICE
CERTIFICATE OF CORRECTION

PATENT NO :     5,998,412

DATED :         December 7, 1999

INVENTOR(S) :   Broka, et al.

It is certified that error appears in the above-identified patent and that said Letters Patent is hereby corrected as shown below:

Column 4, lines 17-25, delete incorrect structure of formula (I)

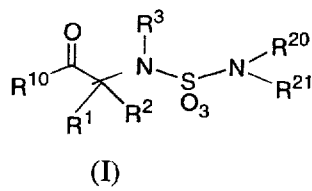

(I)

and replace with

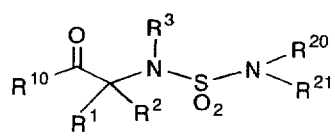

(I)

UNITED STATES PATENT AND TRADEMARK OFFICE
CERTIFICATE OF CORRECTION

PATENT NO : 5,998,412

DATED : December 7, 1999

INVENTOR(S) : Broka, et al.

It is certified that error appears in the above-identified patent and that said Letters Patent is hereby corrected as shown below:

Column 12, lines 15-22, delete incorrect structure of formula (I)

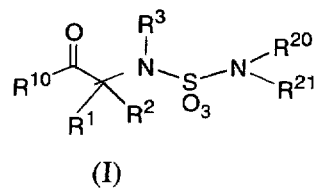

(I)

and replace with

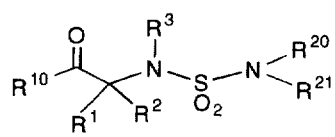

(I)

UNITED STATES PATENT AND TRADEMARK OFFICE
CERTIFICATE OF CORRECTION

PATENT NO : 5,998,412

DATED : December 7, 1999

INVENTOR(S) : Broka, et al.

It is certified that error appears in the above-identified patent and that said Letters Patent is hereby corrected as shown below:

Column 86, lines 53-60, delete incorrect structure of formula (I)

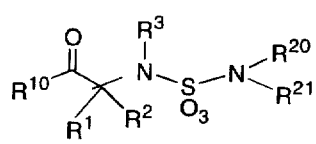

(I)

and replace with

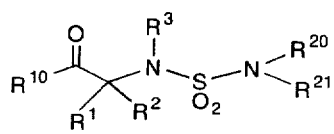

(I)

Signed and Sealed this

Twenty-third Day of January, 2001

Attest:

Attesting Officer

Q. TODD DICKINSON

*Commissioner of Patents and Trademarks*